(12) United States Patent
Gnamm et al.

(10) Patent No.: US 9,657,015 B2
(45) Date of Patent: May 23, 2017

(54) SUBSTITUTED BICYCLIC DIHYDROPYRIMIDINONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Christian Gnamm, Biberach an der Riss (DE); Ralf Anderskewitz, Laupheim (DE); Holger Hoesch, Biberach an der Riss (DE); Gerd Morschhaeuser, Biberach an der Riss (DE); Thorsten Oost, Biberach an der Riss (DE); Stefan Peters, Biberach an der Riss (DE); Uwe Joerg Ries, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/809,323

(22) Filed: Jul. 27, 2015

(65) Prior Publication Data

US 2016/0039812 A1    Feb. 11, 2016

(30) Foreign Application Priority Data

Jul. 31, 2014  (EP) .................................... 14179306

(51) Int. Cl.
*C07D 471/04* (2006.01)

(52) U.S. Cl.
CPC .................................. *C07D 471/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 8,580,800 B2 | 11/2013 | Von Nussbaum et al. | |
| 8,889,700 B2 | 11/2014 | Von Nussbaum et al. | |
| 9,040,516 B2 | 5/2015 | Shiro et al. | |
| 9,115,093 B2 * | 8/2015 | Gnamm ............... | C07D 403/12 |
| 2009/0093477 A1 | 4/2009 | Ray et al. | |
| 2010/0010024 A1 | 1/2010 | Von Nussbaum et al. | |
| 2011/0034433 A1 | 2/2011 | Von Nussbaum et al. | |
| 2012/0004203 A1 | 1/2012 | Von Nussbaum et al. | |
| 2012/0094968 A1 | 4/2012 | Von Nussbaum et al. | |
| 2013/0065913 A1 | 3/2013 | Blench et al. | |
| 2014/0171414 A1 | 6/2014 | Alcaraz et al. | |

FOREIGN PATENT DOCUMENTS

| | | |
|---|---|---|
| CA | 2656307 A1 | 1/2008 |
| DE | 102006031314 A1 | 1/2008 |
| DE | 102007061766 A1 | 6/2009 |
| DE | 102009004197 A1 | 7/2010 |
| EP | 2889291 A1 | 7/2015 |
| GB | 2392910 A | 3/2004 |
| WO | 03053930 | 7/2003 |
| WO | 2004020410 A2 | 3/2004 |
| WO | 2004020412 A1 | 3/2004 |
| WO | 2004024700 A1 | 3/2004 |
| WO | 2004024701 A1 | 3/2004 |
| WO | 2005082863 A2 | 9/2005 |
| WO | 2005082864 A1 | 9/2005 |
| WO | 2006082412 A2 | 8/2006 |
| WO | 2006136857 A1 | 12/2006 |
| WO | 2007129060 A1 | 11/2007 |
| WO | 2008135537 A1 | 11/2008 |

(Continued)

OTHER PUBLICATIONS

International Search Report and Written Opinion for corresponding application PCT/EP2015/067499, date of mailing Sep. 17, 2015.

(Continued)

*Primary Examiner* — Alexander R Pagano
*Assistant Examiner* — Ebenezer O Sackey
(74) *Attorney, Agent, or Firm* — Michael P. Morris; Philip I. Datlow

(57) ABSTRACT

Substituted bicyclic dihydropyrimidinones of formula 1

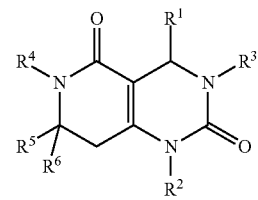

which are inhibitors of neutrophil elastase activity and useful as medicaments for the treatment of, inter alia, COPD. Exemplary is

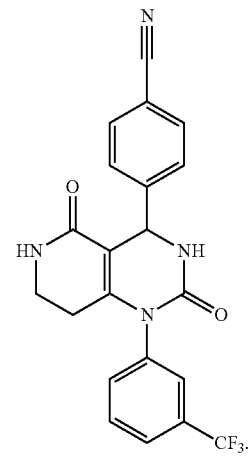

11 Claims, No Drawings

(56) References Cited

FOREIGN PATENT DOCUMENTS

| WO | 2009013444 A1 | 1/2009 |
| WO | 2009037413 A1 | 3/2009 |
| WO | 2009060158 A1 | 5/2009 |
| WO | 2009060203 A1 | 5/2009 |
| WO | 2009060206 A1 | 5/2009 |
| WO | 2009080199 A1 | 7/2009 |
| WO | 2009135599 A1 | 11/2009 |
| WO | 2010078953 A1 | 7/2010 |
| WO | 2010115548 A1 | 10/2010 |
| WO | 2011110858 A1 | 9/2011 |
| WO | 2011110859 A1 | 9/2011 |
| WO | 2012002502 A1 | 1/2012 |
| WO | 2013018804 A1 | 2/2013 |
| WO | 2014009425 A1 | 1/2014 |
| WO | 2014029830 A1 | 2/2014 |
| WO | 2014029831 A1 | 2/2014 |
| WO | 2014029832 A1 | 2/2014 |
| WO | 2014030743 A1 | 2/2014 |

OTHER PUBLICATIONS

Zhang et al., Iron-Catalyzed Vinylogous Aldol Condensation of Biginelli Products and Its Application toward Pyrido [4,3-d] pyrimidinones, The Journal of Organic Chemistry, Mar. 7, 2014, vol. 79, No. 5, pp. 2281-2288.
Abstract in English for DE102007061766, Jun. 25, 2009.
Abstract in English for WO2012002502, May 1, 2012.
Sjo et al., "Neutrophil elastase inhibitors: recent advances in the development of mechanism-based and nonelectrophilic inhibitors", Future Medicinal Chemistry, vol. 4, 2012, p. 651-660.

* cited by examiner

SUBSTITUTED BICYCLIC DIHYDROPYRIMIDINONES AND THEIR USE AS INHIBITORS OF NEUTROPHIL ELASTASE ACTIVITY

This invention relates to substituted bicyclic dihydropyrimidinones of formula 1

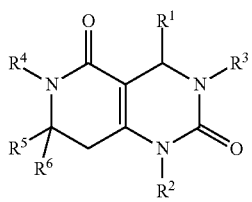

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other autoimmune and allergic disorders, allograft rejection, and oncological diseases.

BACKGROUND INFORMATION

The following references describe neutrophil elastase inhibitors with a monocyclic dihydro-pyrimidinone core: GB2392910, WO04024700, WO05082864, WO05082863, DE102006031314, U.S. Ser. No. 10/001,0024, WO10115548, WO09080199, DE102007061766, WO06136857, WO06082412, WO12002502.

The following references describe neutrophil elastase inhibitors with a bicyclic tetra-hydropyrrolopyrimidinedione core: WO07129060, WO08135537, U.S. Ser. No. 09/009,3477, WO09013444, WO09060206, WO09060203, WO09060158, U.S. Ser. No. 11/003, 4433.

The following references describe neutrophil elastase inhibitors with core structures other than those herein before mentioned: WO04020412, WO04020410, WO03053930, WO10078953, WO09135599, DE102009004197, WO11110858, WO11110859, WO09060158, WO09037413, WO04024701, U.S. Ser. No. 13/006,5913, WO13018804, WO12002502, U.S. Ser. No. 14/017,1414, WO14009425, WO2014029831, WO2014029832 and WO2014029830.

For a review on various inhibitors of neutrophil elastase see: P. Sjö (*Future Med. Chem.* 2012, 4, 651-660).

BRIEF SUMMARY OF THE INVENTION

Neutrophil elastase (NE) is a 29 kDa serine protease. It is expressed in bone marrow precursor cells, stored in the granula of peripheral blood granulocytes at high concentrations and it is released upon cellular activation. To the substrates of NE belong major elements of the extracellular matrix (ECM): elastin, fibronectin, laminin, collagen and proteoglycans. Neutrophil elastase activity leads to ECM degradation, increases migration and chemotaxis of monocytes and vascular smooth muscle cells and directly affects components of the coagulation and fibrinolytic pathways (plasminogen-activator inhibitor 1 (PAI-1) and tissue factor pathway inhibitor (TFPI)). Increased activity of neutrophil elastase is associated with chronic inflammatory and fibrotic diseases of several organs. The potential of neutrophil elastase inhibitors as anti-inflammatory therapies has been reviewed by P. A. Henriksen in *Current Opinion in Hematology* 2014, 21, 23-28. Inhibitors of neutrophil elastase will therefore have an important role for the treatment of different diseases like chronic obstructive pulmonary disease (COPD), idiopathic pulmonary fibrosis and other fibrotic diseases, cancer, acute lung injury, acute respiratory distress syndrome, bronchiectasis, cystic fibrosis, alpha1-antitrypsin deficiency and others.

For a review on the potential of neutrophil elastase inhibitors as anti-inflammatory therapies see: P. A. Henriksen (*Curr. Opin. Hematol.* 2014, 21, 23-28).

The problem of the present invention is to prepare new compounds which on the basis of their pharmaceutical effectiveness as inhibitors of neutrophil elastase activity, may be used therapeutically, that is for the treatment of pathophysiological processes caused by increased activity of neutrophil elastase.

It has surprisingly been found that the compounds of the present invention have the following properties which are advantageous in view of the indications of the current invention.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, are additionally effective as inhibitors of neutrophil serin protease proteinase 3 and exhibit favourable inhibitory potency, as determined by the half maximal inhibitory concentration ($IC_{50}$), in an enzymatic inhibition assay. This inhibitory activity on a second neutrophil serin protease may be beneficial for pharmacological efficacy.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose ($ED_{50}$), in models of human neutrophil elastase-induced lung injury in mouse or rat, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable metabolic stability in an in vitro microsomal assay for metabolic stability as described in E. Kerns & L. Di (*Drug-like properties: concepts, structure design and methods: from ADME to toxicity optimization*, Elsevier, 1st ed, 2008), chapter 29 and references therein.

Some compounds according to the present invention, including the physiologically acceptable salts, exhibit favourable metabolic stability in an in vitro hepatocytes assay for metabolic stability as described in E. Kerns & L. Di (*Drug-like properties: concepts, structure design and* methods: from ADME to toxicity optimization, Elsevier, 1st ed, 2008), chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}=Dose/AUC$ ($F_{oral}$: oral bioavailability, a) AUC: area under the curve), a reduced in vivo clearance is expected to lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di (*Drug-like properties: concepts, structure design and methods: from ADME to toxicity optimization*, Elsevier, 1st ed, 2008), chapter 26 and references therein. For an oral drug, improved permeability is expected to translate into a higher fraction of the drug absorbed in the intestinal tract, thus, resulting in higher dose-normalized systemic exposure (AUC).

Some compounds according to the present invention, including the physiologically acceptable salts, exhibit a favourable, that is low efflux ratio (permeability in the efflux direction divided by the permeability in the influx direction) in an in vitro Caco-2 or MDCK cell layer method as described in E. Kerns & L. Di (*Drug-like properties: concepts, structure design and methods: from ADME to toxicity optimization*, Elsevier, 1st ed, 2008), chapter 26 and 27 and references therein. For an oral drug, an improved, that is reduced efflux ratio is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di (*Drug-like properties: concepts, 15 structure design and methods: from ADME to toxicity optimization*, Elsevier, 1st ed, 2008), chapter 25 and references therein. For an oral drug, improved aqueous solubility is expected to translate into a higher fraction of the drug absorbed in the intestinal tract resulting in higher dose-normalized systemic exposure (AUC) and/or oral bioavailability ($F_{oral}$) and/or peak plasma concentration after administration ($C_{max}$). Furthermore, improved aqueous solubility is expected to reduce the risk of development challenges, such as expensive formulations, increased development time, high drug load.

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability, favourable permeability and favourable aqueous solubility. Accordingly, some compounds of the present invention are expected to exhibit favourable pharmacokinetic (PK) properties after oral dosing, in particular favourable systemic exposure (area under the curve, AUC), thus, leading to favourable efficacy in vivo.

Some compounds according to the present invention, including the physiologically acceptable salts, exhibit favourable pharmacokinetic (PK) properties. The PK properties can be determined in pre-clinical animal species, for example mouse, rat, hamster, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL) and bioavailability after oral administration ($F_{oral}$), peak plasma concentration after administration ($C_{max}$), time to reach Cmax ($T_{max}$).

The compounds of the invention and metabolites thereof are devoid of the hydrazine sub-structure that causes structural alerts for mutagenicity and carcinogenicity as described in Benigni et al. (*Chem. Rev.* 2011, 11, 2507-2536). Thus, compounds of the invention may bear the advantage of reduced genotoxic potential.

Some compounds according to the present invention, including the physiologically acceptable salts, exhibit favourable, that is low inhibition of cytochrome P450 (CYP) isozymes in corresponding in vitro assays for CYP isozyme inhibition as described in E. Kerns & L. Di (*Drug-like properties: concepts, structure design and methods: from ADME to toxicity optimization*, Elsevier, 1st ed, 2008), chapter 32 and references therein. Reduced inhibition of CYP isozymes is expected to translate into a reduced risk for undesirable drug-drug interactions which is the interference of one drug with the normal metabolic or pharmacokinetic behaviour of a co-administered drug.

Some compounds according to the present invention, including the physiologically acceptable salts, exhibit favourable, that is low, inhibition of the hERG channel in a patch clamp assay as described in E. Kerns & L. Di (*Drug-like properties: concepts, structure design and methods: from ADME to toxicity optimization*, Elsevier, 1st ed, 2008), chapter 34 and references cited therein.

Some compounds according to the present invention, including the physiologically acceptable salts, exhibit favourable, that is low CYP induction potential. Cytochrome P450 (CYP) induction can affect the pharmacokinetics of a drug molecule upon multiple dosing, which can result in pharmacokinetic drug-drug interactions with coadministered drugs. CYP induction can lead to decreased exposure of the inducing compound (e.g. autoinduction) or decreased exposure of a coadministered compound metabolized by the induced enzyme. CYP induction can also lead to an increase in the metabolism of a drug causing changes in pharmacological (active metabolite) and toxicological (toxic metabolite) outcomes.

DETAILED DESCRIPTION OF THE INVENTION

A compound of formula 1

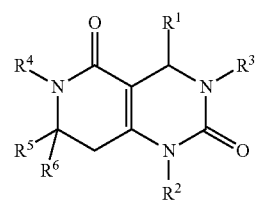

1 wherein $R^1$ is phenyl or pyridinyl; each ring optionally substituted with one or two substituents independently selected from the group consisting of halogen, NC—, $H_2N$—, $R^{1.1}$, $R^{1.1}O$—, $R^{1.2}$, $R^{1.3}$, $R^{1.4}(O)S$—, $R^{1.4}(O)_2S$— and $R^{1.5}R^{1.5}N(O)C$—;

$R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{1.2}$ is HO—$C_{1-6}$-alkyl- or $R^{1.1}$—O—$C_{1-6}$-alkyl-;

$R^{1.3}$ is phenyl or a five- or six-membered heterocyclic or heteroaryl ring, wherein one, two or three elements are replaced by an element independently selected from the group consisting of N, O, S, S(O) and $S(O)_2$; each ring optionally substituted with one, two or three substituents independently selected from the group consisting of halogen, NC—, $H_2N$—, HO—, O=, $R^{1.3.1}$, $R^{1.3.1}O$—, $R^{1.3.1}$—(O)C—, $R^{1.3.2}$, $R^{1.3.1}(O)_2S$— and $R^{1.3.3}$;

$R^{1.3.1}$ is independently selected from $R^{1.1}$;
$R^{1.3.2}$ is independently selected from $R^{1.2}$;
$R^{1.3.3}$ is independently selected from the group consisting of HO(O)C—, $H_2N(O)C$—, $R^{1.1}$—O—(O)C—, $R^{1.1}$—NH—(O)C— and $(R^{1.1})_2N$—(O)C—;

$R^{1.4}$ is independently selected from the group consisting of H, HO—, $R^{1.1}$ and $R^{1.2}$; preferably $R^{1.1}$;

$R^{1.5}$ is independently selected from the group consisting of H, $R^{1.1}$, $R^{1.2}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from $R^{1.5.1}$, $R^{1.5.2}$ and $R^{1.5.3}$;

$R^{1.5.1}$ is selected from the group consisting of HO—, halogen, NC—, $R^{1.1}O$—, $R^{1.5.4}$, $R^{1.5.5}$ and $R^{1.5.6}$; or $R^{1.5.2}$ denotes a four-membered heterocyclic ring containing one element independently selected from among N, O, S, S(O) and $S(O)_2$; or $R^{1.5.3}$ denotes a five- or six-membered heterocyclic or heteroaryl ring containing one, two or three elements independently selected from among N, O, S, S(O) and $S(O)_2$; each of the rings optionally substituted with one or two substituents independently selected from among HO—, O=, halogen, NC—, $R^{1.1}$, $R^{1.1}O$—, $R^{1.1}$—(O)C—, HO—$C_{1-6}$-alkyl-, $R^{1.1}$—O—$C_{1-6}$-alkyl-, $R^{1.5.4}$, $R^{1.5.5}$ and $R^{1.5.6}$; or two substituents are together $R^{1.5.7}$;

$R^{1.5.4}$ is independently selected from the group consisting of $H_2N$—, $R^{1.1}$—HN—, $(R^{1.1})_2N$—, $R^{1.1}$—(O)C—HN— and $R^{1.1}$—(O)C—$(R^{1.1})N$—;

$R^{1.5.5}$ is independently selected from the group consisting of $R^{1.1}$—(O)S—, $R^{1.1}$—(O)_2S—, $R^{1.1}(HN)S$—, $R^{1.1}(HN)(O)S$—, $R^{1.1}(R^{1.1}N)S$—, $R^{1.1}(R^{1.2}N)S$—, $R^{1.1}(R^{1.1}N)(O)S$—, $R^{1.1}(R^{1.2}N)(O)S$—, $R^{1.1}(NC$—$N)S$— and $R^{1.1}(NC$—$N)(O)S$—;

$R^{1.5.6}$ is independently selected from the group consisting of HO(O)C—, $H_2N(O)C$—, $R^{1.1}$—O—(O)C—, $R^{1.1}$—NH—(O)C— and $(R^{1.1})_2N$—(O)C—;

$R^{1.5.7}$ is independently selected from the group consisting of $C_{1-6}$-alkylene and $C_{1-6}$-haloalkylene, wherein optionally one or two $CH_2$-groups are replaced by —HN—, —$(R^{1.1})N$—, —$(R^{1.1}(O)C$—$)N$—, —O—, —S—, —S(O)— or —$S(O)_2$—;

or $R^{1.5}$ is phenyl or a five- or six-membered heterocyclic or heteroaryl ring containing one, two or three elements independently selected from N, O, S, S(O) and $S(O)_2$; each ring optionally substituted with one or two substituents independently selected from HO—, O=, NC—, halogen, $R^{1.1}$, $R^{1.1}O$—, $R^{1.1}$—(O)C—, $R^{1.2}$, $R^{1.5.4}$, $R^{1.5.5}$ and $R^{1.5.6}$; or two substituents are together $R^{1.5.7}$;

or two $R^{1.5}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and $S(O)_2$; optionally substituted with one or two substituents, independently selected from among HO—, F—, O=, NC—, $R^{1.1}$, $R^{1.1}O$—, $R^{1.1}$—(O)C—, $R^{1.2}$, $R^{1.5.4}$, $R^{1.5.5}$ and $R^{1.5.6}$, phenyl and a five- or six-membered heterocyclic or heteroaryl ring containing one, two or three elements independently selected from among N, O, S, S(O) and $S(O)_2$; or two substituents are together $R^{1.5.7}$;

$R^2$ is phenyl or pyridinyl; each ring optionally substituted with one or two substituents independently selected from halogen, $C_{1-4}$-alkyl- and $C_{1-4}$-haloalkyl-;

$R^3$ is a residue independently selected from the group consisting of
$R^{3.1}$—;
$R^{3.2}(O)C$—;
$R^{3.2}O(O)C$—;
$R^{3.2}O(O)C$-A-; preferably $R^{3.2}O(O)C$—$CH_2$—;
$R^{3.2}(O)_2S$—;
$(R^{3.2})_2N(O)C$ and
$(R^{3.2})_2N(O)C$-A-; preferably $(R^{3.2})_2N(O)C$—$CH_2$—;

$R^{3.1}$ is independently selected from the group consisting of H, $R^{3.3}$, $R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from $R^{3.1.1}$;

$R^{3.1.1}$ is selected from the group consisting of HO—, halogen, NC—, $R^{3.3}O$—, $R^{3.5}$, $R^{3.6}$ and $R^{3.7}$; or $R^{3.1.1}$ denotes a ring independently selected from phenyl and a four-membered heterocyclic ring containing one element independently selected from among N, O, S, S(O) and $S(O)_2$; or $R^{3.1.1}$ denotes a five- or six-membered heterocyclic or heteroaryl ring containing one, two or three elements independently selected from among N, O, S, S(O) and $S(O)_2$; each of the rings optionally substituted with one or two substituents independently selected from among HO—, O=, halogen, NC—, $R^{3.3}$, $R^{3.3}O$—, $R^{3.3}$—(O)C—, $R^{3.4}$, $R^{3.5}$, $R^{3.6}$ and $R^{3.7}$; or two substituents are together $R^{3.8}$;

$R^{3.2}$ is independently selected from $R^{3.1}$, phenyl or a five- or six-membered heterocyclic or heteroaryl ring containing one, two or three elements independently selected from N, O, S, S(O) and $S(O)_2$; each ring optionally substituted with one or two substituents independently selected from HO—, O=, NC—, halogen, $R^{3.3}$, $R^{3.3}O$—, $R^{3.3}$—(O)C—, $R^{3.4}$, $R^{3.5}$, $R^{3.6}$ and $R^{3.7}$; or two substituents are together $R^{3.8}$;

or two $R^{3.2}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and $S(O)_2$; optionally substituted with one or two substituents, independently selected from among HO—, F—, O=, NC—, $R^{3.3}$, $R^{3.3}O$—, $R^{3.3}$—(O)C—, $R^{3.4}$, $R^{3.5}$, $R^{3.6}$, $R^{3.7}$, phenyl and a five- or six-membered heterocyclic or heteroaryl ring containing one, two or three elements independently selected from among N, O, S, S(O) and S(O)$_2$; or two substituents are together R$^{3.8}$;

R$^{3.3}$ is independently selected from the group consisting of C$_{1-6}$-alkyl-, C$_{3-6}$-cycloalkyl-, C$_{1-6}$-haloalkyl- and C$_{3-6}$-halocycloalkyl;

R$^{3.4}$ is HO—C$_{1-6}$-alkyl- or R$^{3.3}$—O—C$_{1-6}$-alkyl-;

R$^{3.5}$ is independently selected from the group consisting of H$_2$N—, R$^{3.3}$—HN—, (R$^{3.3}$)$_2$N—, R$^{3.3}$—(O)C—HN— and R$^{3.3}$—(O)C—(R$^{3.3}$)N—;

R$^{3.6}$ is independently selected from the group consisting of R$^{3.3}$—(O)S—, R$^{3.3}$—(O)$_2$S—, R$^{3.3}$(HN)S—, R$^{3.3}$(HN)(O)S—, R$^{3.3}$(R$^{3.3}$N)S—, R$^{3.3}$(R$^{3.3}$N)(O)S—, R$^{3.3}$(R$^{3.4}$N)S—, R$^{3.3}$(R$^{3.4}$N)(O)S—R$^{3.3}$(NC—N)S— and R$^{3.3}$(NC—N)(O)S—;

R$^{3.7}$ is independently selected from the group consisting of HO(O)C—, H$_2$N(O)C—, R$^{3.3}$—O—(O)C—, R$^{3.3}$—NH—(O)C— and (R$^{3.3}$)$_2$N—(O)C—;

R$^{3.8}$ is independently selected from the group consisting of C$_{1-6}$-alkylene and C$_{1-6}$-haloalkylene, wherein optionally one or two CH$_2$-groups are replaced by —HN—, —(R$^{3.3}$)N—, —(R$^{3.4}$)N—, —(R$^{3.3}$(O)C—)N—, —(R$^{3.4}$(O)C—)N—, —O—, —S—, —S(O)— or —S(O)$_2$—;

A is —CH$_2$—, —CH$_2$—CH$_2$— or —CH$_2$—CH$_2$—CH$_2$—; preferably —CH$_2$—; optionally substituted with one or two substituents independently selected from the group consisting of halogen, R$^{3.3}$, R$^{3.3}$O— and R$^{3.4}$; or two substituents together are R$^{3.8}$;

R$^4$ is R$^3$, preferably H, R$^{3.3}$, R$^{3.4}$ or R$^{3.7}$; most preferably H or methyl;

R$^5$, R$^6$ is independently selected from H, C$_{1-6}$-alkyl-, C$_{3-6}$-cycloalkyl-, C$_{1-6}$-haloalkyl-, C$_{3-6}$-halocycloalkyl-, HO—C$_{1-6}$-alkyl- and C$_{1-6}$-alkyl-O—C$_{1-6}$-alkyl-; preferably methyl; or R$^5$ and R$^6$ are together C$_{1-6}$-alkylene or C$_{1-6}$-haloalkylene, wherein optionally one CH$_2$-group can be replaced by —O—, —S—, —S(O)— or —S(O)$_2$—;

or optical and geometrical isomers, solvates, hydrates or salts, preferably pharmaceutically acceptable salts, thereof.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, C$_{1-6}$-alkyl means an alkyl group or radical having 1 to 6 carbon atoms.

In general in single groups like HO, H$_2$N, S(O), S(O)$_2$, NC (cyano), HOOC, F$_3$C or the like, the skilled artisan can see the radical attachment point(s) to the molecule from the free valences of the group itself. For combined groups comprising two or more subgroups, the first or last named subgroup, where the free valence is indicated, is the radical attachment point, for example, the substituent "aryl-C$_{1-3}$-alkyl-" means an aryl group which is bound to a C$_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk or a broken line may be used in sub-formulas to indicate the bond which is connected to the core molecule as defined.

For example, the term "3-carboxypropyl-group" represents the following substituent:

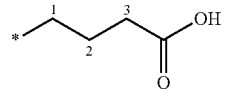

wherein the carboxy group is attached to the third carbon atom of the propyl group. The terms "1-methylpropyl-", "2,2-dimethylpropyl-" or "cyclopropylmethyl-" group represent the following groups:

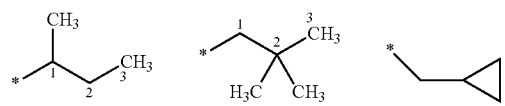

The asterisk or a broken line may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, that is more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (that is an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2''-nitrilotris-(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH_2$—$CH(CH_3)$—$CH_2$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine and bromine, preferably fluorine and chlorine, particularly preferred is fluorine. Examples include: $H_2FC$—, $HF_2C$—, $F_3C$—.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring system including aromatic ring system containing one or more elements selected from N, O, S, S(O) or S(O)$_2$, consisting of 3 to 14 ring atoms wherein none of the heteroatoms is part of the aromatic ring. The term "heterocyclyl" is intended to include all the possible isomeric forms; thus, the term "heterocyclyl" includes the following exemplary structures which are not depicted as radicals as each form may be attached through a covalent bond to any atom so long as appropriate valences are maintained:

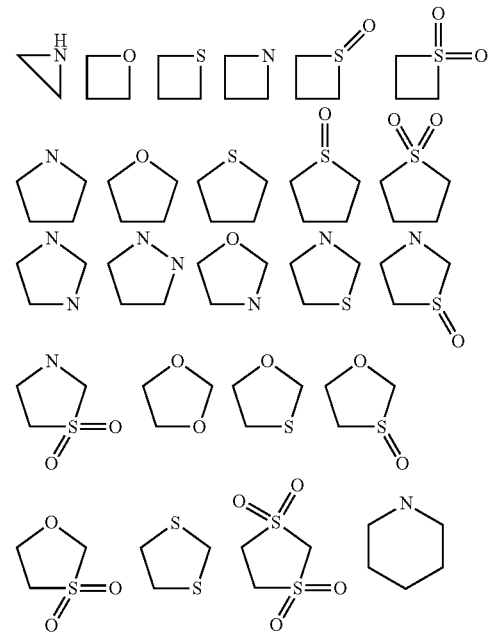

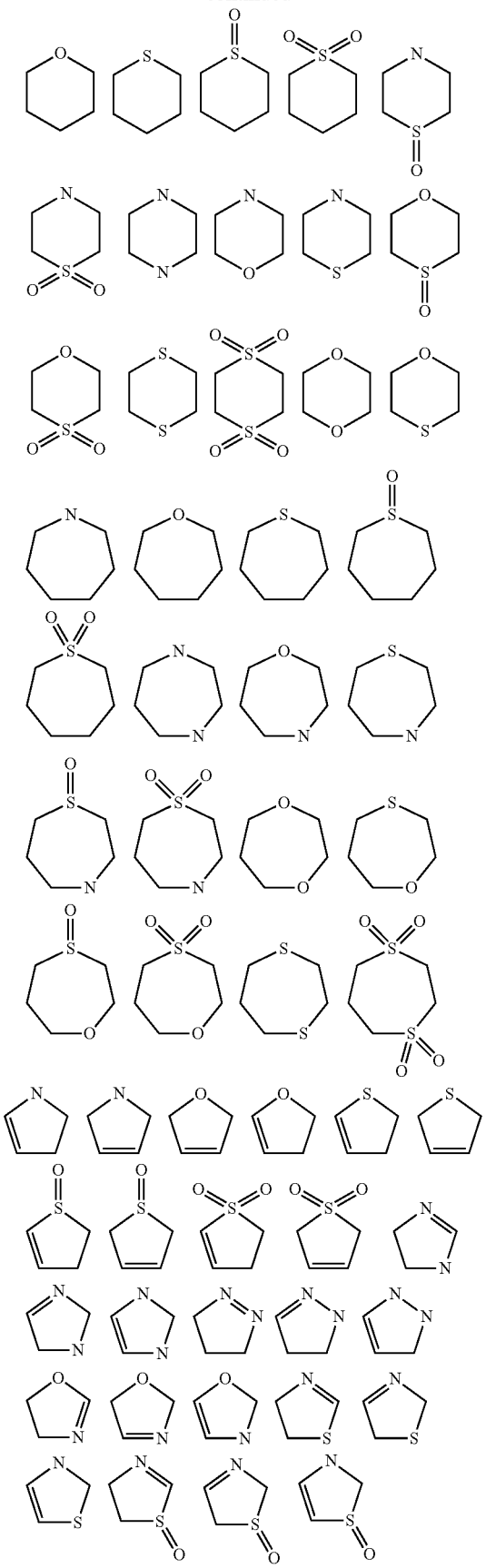
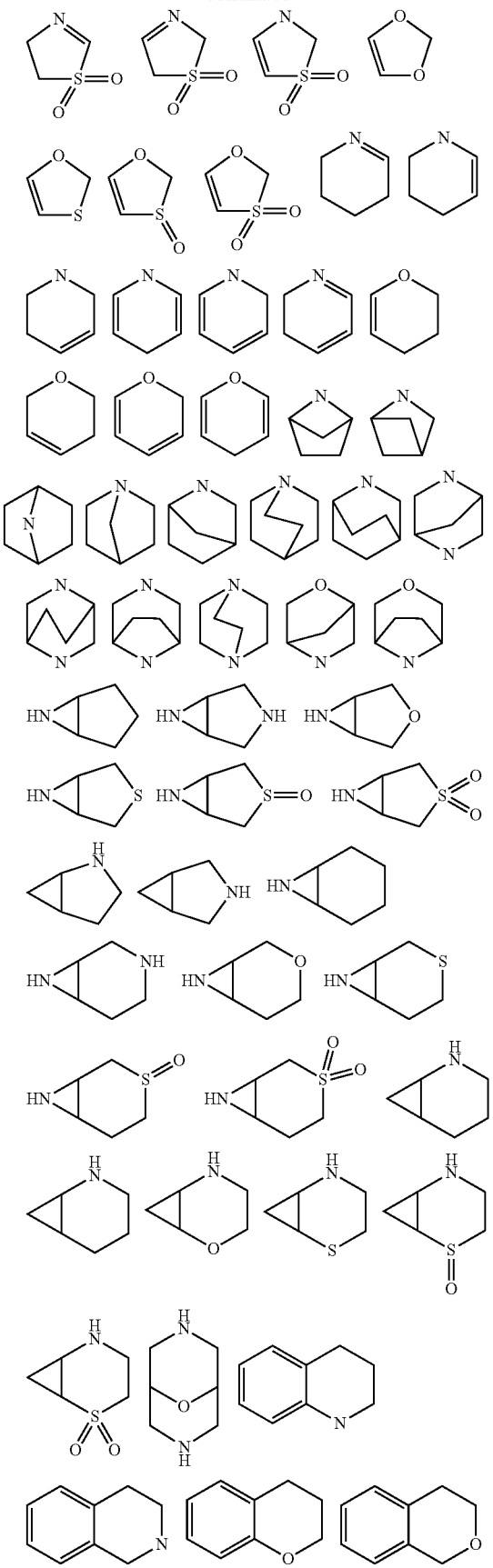

-continued

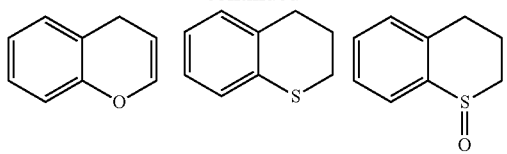
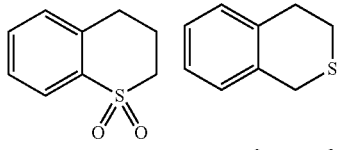
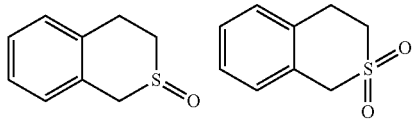
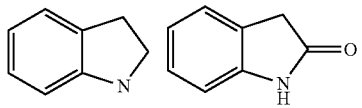
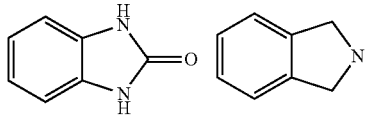
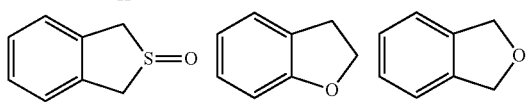
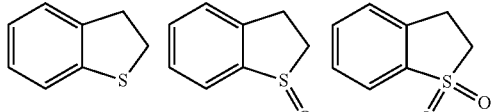
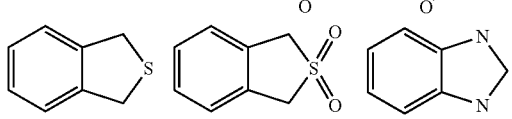
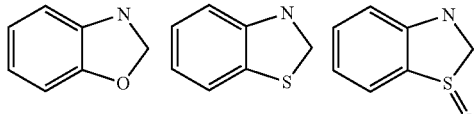
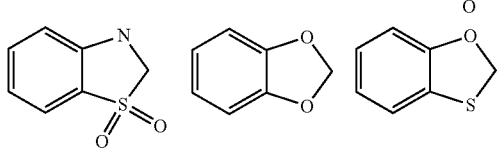
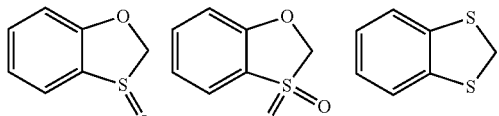
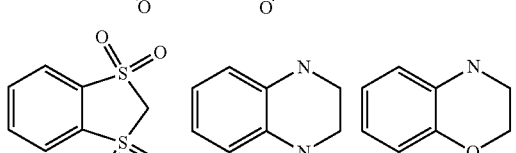
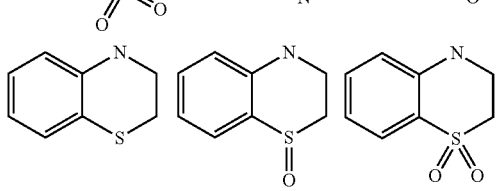

-continued

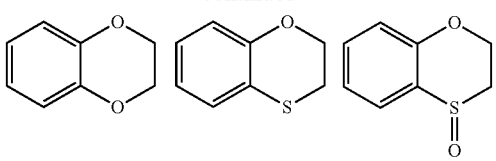
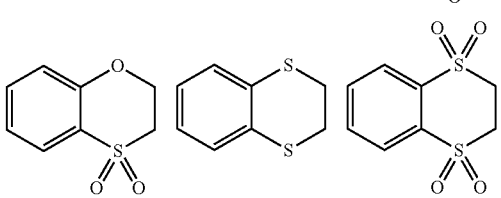

The term "heteroaryl" means a mono- or polycyclic-ring systems containing one or more elements selected from N, O, S, S(O) or S(O)$_2$, consisting of 5 to 14 ring atoms wherein at least one of the heteroatoms is part of aromatic ring. The term "heteroaryl" is intended to include all the possible isomeric forms; Thus, the term "heteroaryl" includes the following exemplary structures which are not depicted as radicals as each form may be attached through a covalent bond to any atom so long as appropriate valences are maintained:

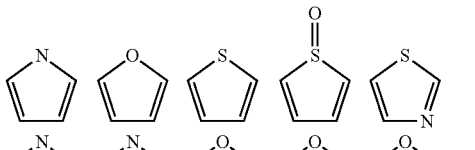
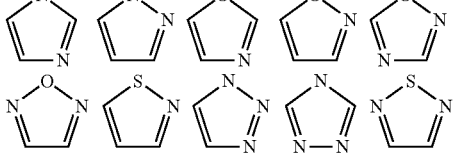
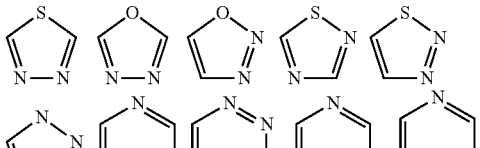
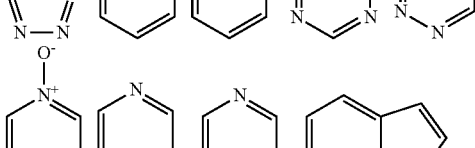
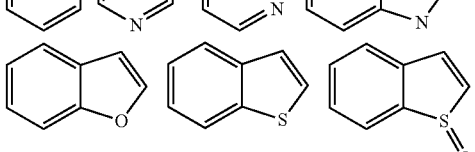
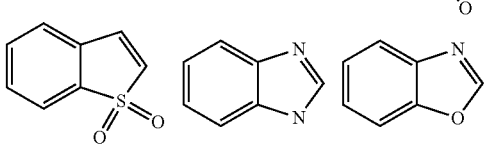
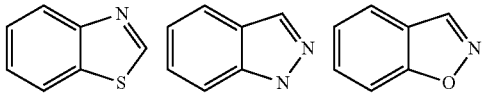

-continued

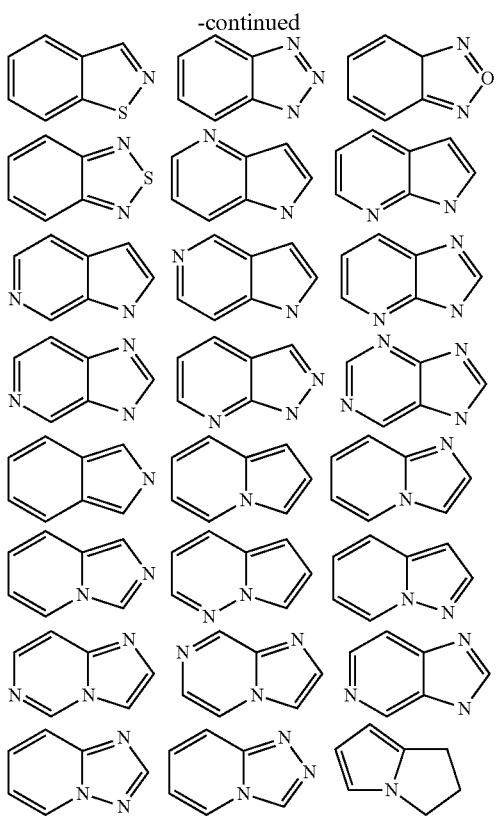

Further Embodiments

Embodied are the above compounds of formula 1, wherein
R¹ denotes -phenyl-CN
or a pharmaceutically acceptable salt thereof.

Embodied are the above compounds of formula 1, wherein
R² is selected from the group consisting of -phenyl-CF₃, -phenyl-CHF₂, -pyridyl-CF₃, and -pyridyl-CHF₂,
or a pharmaceutically acceptable salt thereof.

Embodied are the above compounds of formula 1, wherein
R³ is selected from the group consisting of H, $C_{1-3}$-alkyl, —CONH—$C_{1-3}$-alkyl, —CH₂—CO₂—$C_{1-3}$-alkyl, —CH₂—CO—N($C_{1-3}$-alkyl)₂ and —CH₂—CONH—$C_{1-3}$-alkyl
or a pharmaceutically acceptable salt thereof.

Embodied are the above compounds of formula 1, wherein
R⁴ is selected from the group consisting of H, $C_{1-3}$-alkyl and —CONH—$C_{1-4}$-alkyl-OH
or a pharmaceutically acceptable salt thereof.

Embodied are the above compounds of formula 1, wherein
R⁵ and R⁶ independently from each other denote H or $C_{1-3}$-alkyl
or a pharmaceutically acceptable salt thereof.

Embodied are the above compounds of formula 1, wherein
R¹ denotes a group of formula a.1

R² is selected from the group consisting of a group of formula a.2 or a.3

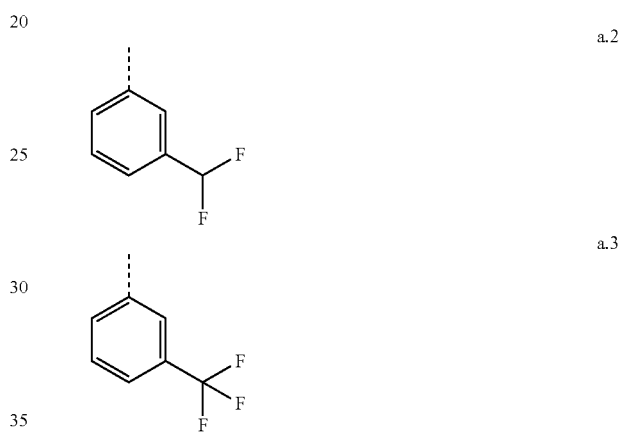

R³ is selected from the group consisting of H, CH₃, —CONH—CH₃, —CONH—CH₂CH₂OH, —CH₂—COO—CH₃, —CH₂—CO—N(CH₃)₂ and —CH₂—CO—NHCH₃;
R⁴ is selected from the group consisting of H, CH₃ and —CONH—CH₂CH₂CH₂—OH;
R⁵ and R⁶ independently from each other denote H or CH₃;
or a pharmaceutically acceptable salt thereof.

Embodied are the above compounds of formula 1 selected from the group consisting of compounds 1.a to 1.o

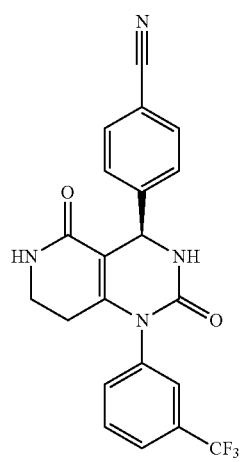

1.a

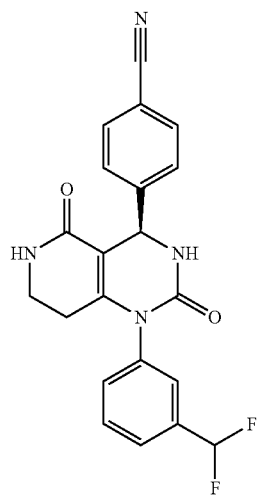 1.b
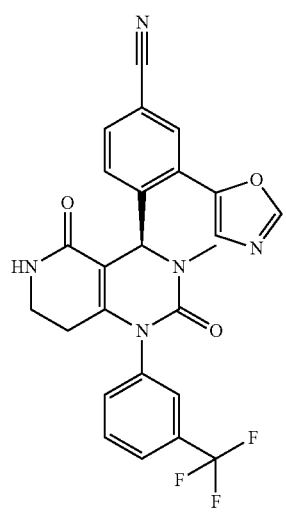 1.e
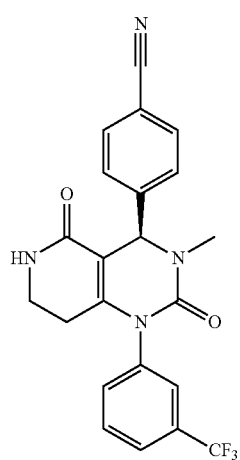 1.c
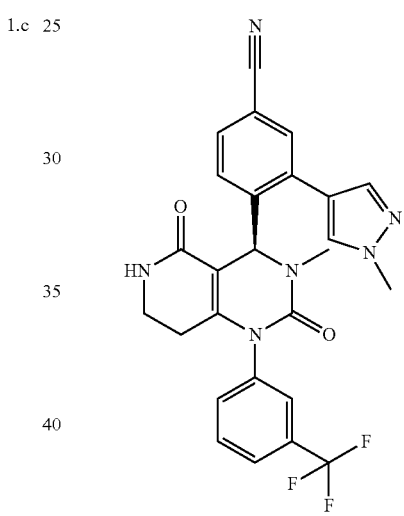 1.f
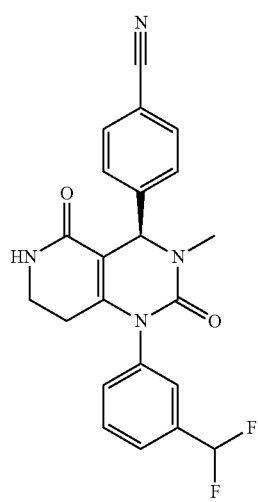 1.d
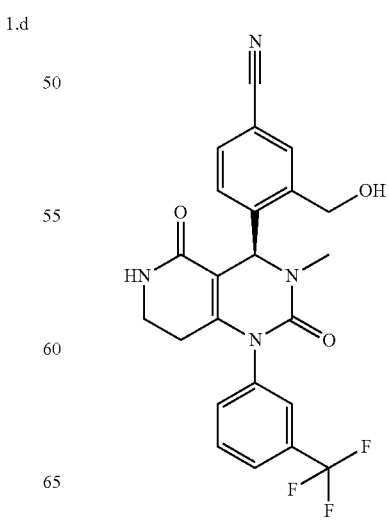 1.g -continued
1.h
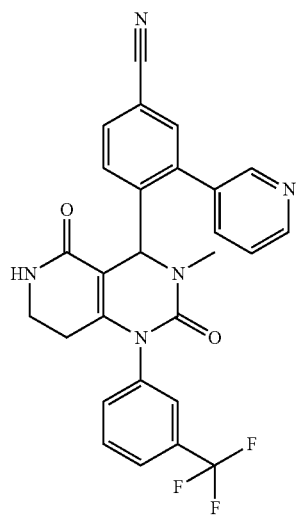
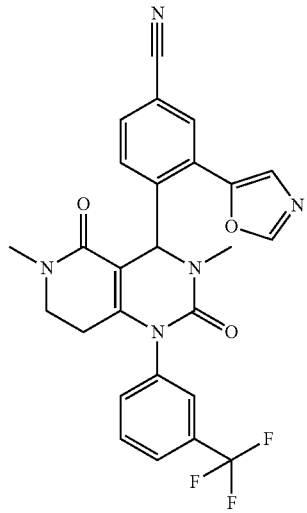
1.k
1.i
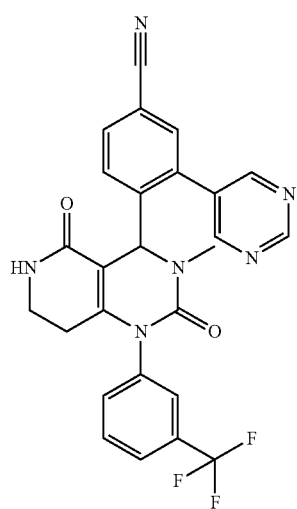
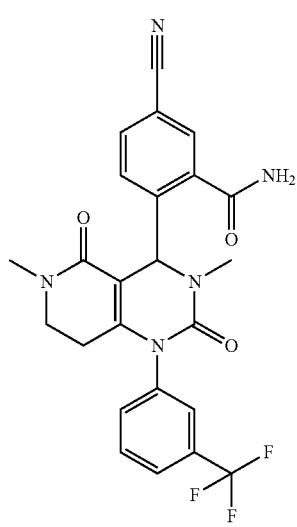
1.l
1.j
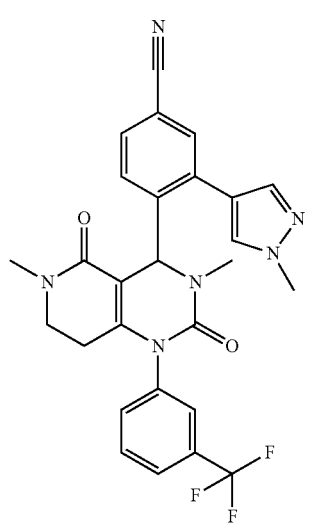
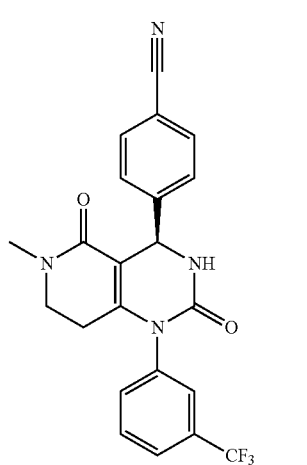
1.m -continued 1.n
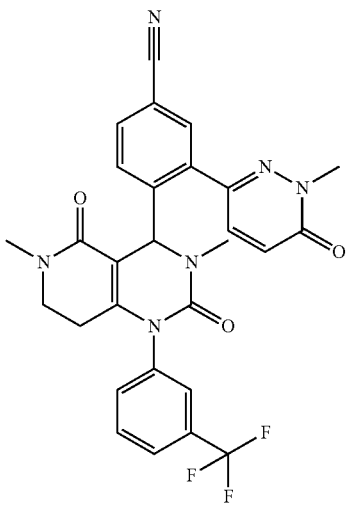

or a pharmaceutically acceptable salt thereof.

Embodied are the above compounds, wherein the configuration of formula 1 is according to formula 1.A, 1.o
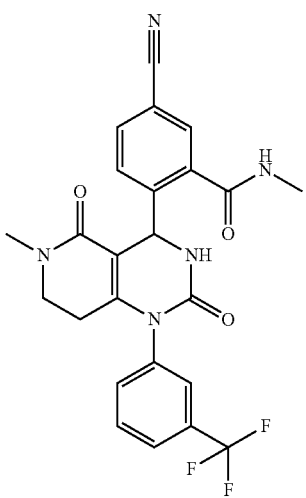

or a pharmaceutically acceptable salt thereof.

1.A
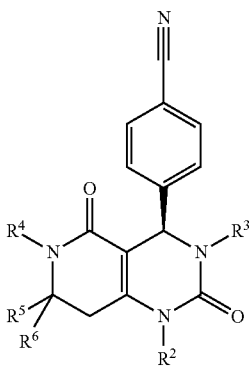

or a pharmaceutically acceptable salt thereof.

Embodied are the above compounds of formula 1, wherein
$R^1$ denotes -phenyl-CN, and
$R^2$ is selected from the group consisting of -phenyl-CF$_3$ and -phenyl-CHF$_2$
or a pharmaceutically acceptable salt thereof.

Embodied are the above compounds of formula 1.A, wherein
$R^2$ is selected from the group consisting of -phenyl-CF$_3$, -phenyl-CHF$_2$, -pyridyl-CF$_3$, and -pyridyl-CHF$_2$
$R^3$ is selected from the group consisting of H, $C_{1-3}$-alkyl, —CONH—$C_{1-3}$-alkyl, —CONH—$C_{1-3}$-alkyl-OH, —CH$_2$—COO—$C_{1-3}$-alkyl, —CH$_2$—CO—N($C_{1-3}$-alkyl)$_2$, and —CH$_2$—CO—NHC$_{1-3}$-alkyl,
$R^4$ is selected from the group consisting of H, $C_{1-3}$-alkyl and —CONH—$C_{1-4}$-alkyl-OH,
$R^5$ and $R^6$ independently from each other denote H or $C_{1-3}$-alkyl,
or a pharmaceutically acceptable salt thereof.

Another embodiment of the current invention are the above compounds of formula 1 for use as a medicament.

Embodied are the above compounds of formula 1 for use as a medicament for the treatment of asthma and allergic diseases, gastrointestinal inflammatory diseases, glomerulonephritis, eosinophilic diseases, chronic obstructive pulmonary disease, infection by pathogenic microbes, rheumatoid arthritis, neutrophilic diseases, cystic fibrosis (CF), non-cystic fibrosis, idiopathic pulmonary fibrosis, bronchiectasis, ANCA-associated vasculitis, lung cancer, non-cyctic fibrosis bronchiectasis, emphysema, chronic bronchitis, acute lung injury (ALI), acute respiratory distress syndrome (ARDS), pulmonary hypertension, pulmonary arterial hypertension (PAH) and Alpha-1-antitrypsin deficiency (AATD.), obesity and related inflammation, insulin resistance, diabetes, fatty liver and liver steatosis.

A further embodiment of the present invention is a compound of formula 1, for use as a medicament for the treatment of traumatic brain injury, abdominal aortic aneurism and Graft vs. Host Disease (GvHD).

Another embodiment of the current invention is a pharmaceutical composition, containing one or more compounds of formula 1 or a pharmaceutically active salt thereof.

Another embodiment of the current invention is a pharmaceutical composition comprising additionally to a compound of formula 1 a pharmaceutically active compound selected from the group consisting of betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, but also combinations of two or three active substances.

Embodied are above compounds of formula 1, wherein $R^1$ is $R^{1.a}$ and $R^{1.a}$ is phenyl or pyridinyl; each ring optionally substituted with one or two substituents independently selected from the group consisting of halogen, NC—, $R^{1.1}$, $R^{1.2}$, $R^{1.3}$, $R^{1.4}$(O)S—, $R^{1.4}$(O)$_2$S— or $R^{1.5}R^{1.5}$N(O)C—;

Embodied are above compounds of formula 1, wherein $R^1$ is $R^{1.a}$ and $R^{1.a}$ is phenyl; optionally substituted with one or two substituents independently selected from the group consisting of halogen, NC—, $R^{1.1}$, $R^{1.2}$, $R^{1.3}$, $R^{1.4}$(O)S—, $R^{1.4}$(O)$_2$S— or $R^{1.5}R^{1.5}$N(O)C—.

Embodied are above compounds of formula 1, wherein $R^{1.b}$ is $R^{1.b}$ and $R^{1.b}$ is phenyl; optionally substituted with one or two substituents independently selected from the group consisting of halogen, NC—, $R^{1.1}$, $R^{1.2}$, $R^{1.3}$, $R^{1.4}$(O)S— and $R^{1.4}$(O)$_2$S—; and $R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{1.2}$ is HO—$C_{1-6}$-alkyl- or $R^{1.1}$—O—$C_{1-6}$-alkyl-;

$R^{1.3}$ is a five-membered heterocyclic or heteroaryl ring, wherein one, two or three elements are replaced by an element independently selected from the group consisting of N, O, S, S(O) and S(O)$_2$; each ring optionally substituted with one, two or three substituents independently selected from the group consisting of halogen, NC—, H$_2$N—, HO—, O=, $R^{1.3.1}$, $R^{1.3.1}$O—, $R^{1.3.1}$(O)C—, $R^{1.3.2}$ and $R^{1.3.1}$(O)$_2$S— or $R^{1.3.3}$;

$R^{1.4}$ is independently selected from the group consisting of $R^{1.1}$.

Embodied are above compounds of formula 1, wherein $R^1$ is $R^{1.c}$ and $R^{1.c}$ is phenyl; optionally substituted with one or two substituents independently selected from the group consisting of halogen, NC— and $R^{1.5}R^{1.5}$N(O)C—; and $R^{1.5}$ is independently selected from the group consisting of H, $R^{1.1}$, $R^{1.2}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from among $R^{1.5.1}$—, $R^{1.5.2}$— and $R^{1.5.3}$—;

$R^{1.5.1}$ is selected from the group consisting of HO—, halogen, NC—, $R^{1.1}$O—, $R^{1.5.4}$, $R^{1.5.5}$ and $R^{1.5.6}$—; or $R^{1.5.2}$ denotes a four-membered heterocyclic ring containing one element independently selected from among N, O, S, S(O) and S(O)$_2$; or $R^{1.5.3}$ denotes a five- or six-membered heterocyclic or heteroaryl ring containing one, two or three elements independently selected from among N, O, S, S(O) and S(O)$_2$; each of the rings optionally substituted with one or two substituents independently selected from among HO—, O=, halogen, NC—, $R^{1.1}$, $R^{1.1}$O—, $R^{1.1}$—(O)C—, HO—$C_{1-6}$ alkyl, $R^{1.1}$—O—$C_{1-6}$-alkyl-, $R^{1.5.4}$, $R^{1.5.5}$ and $R^{1.5.6}$ or two substituents are together $R^{1.5.7}$;

$R^{1.5.4}$ is independently selected from the group consisting of H$_2$N—, $R^{1.1}$—HN—, $(R^{1.1})_2$N—, $R^{1.1}$—(O)C—HN— and $R^{1.1}$—(O)C—$(R^{1.1})$N—;

$R^{1.5.5}$ is independently selected from the group consisting of $R^{1.1}$—(O)S—, $R^{1.1}$—(O)$_2$S—, $R^{1.1}$(HN)S—, $R^{1.1}$(HN)(O)S—, $R^{1.1}(R^{1.1}$N)S—, $R^{1.1}(R^{1.2}$N)S—, $R^{1.1}(R^{1.1}$N)(O)S—, $R^{1.1}(R^{1.2}$N)(O)S—, $R^{1.1}$(NC—N)S— and $R^{1.1}$(NC—N)(O)S—;

$R^{1.5.6}$ is independently selected from the group consisting of HO(O)C—, H$_2$N(O)C—, $R^{1.1}$—O—(O)C—, $R^{1.1}$—NH—(O)C— and $(R^{1.1})_2$N—(O)C—;

$R^{1.5.7}$ is independently selected from the group consisting of $C_{1-6}$-alkylene and $C_{1-6}$-haloalkylene, wherein optionally one or two CH$_2$-groups are replaced by —HN—, —$(R^{1.1})$N—, —$(R^{1.1}$(O)C—)N—, —O—, —S—, —S(O)— or —S(O)$_2$—;

or $R^{1.5}$ is phenyl or a five- or six-membered heterocyclic or heteroaryl ring containing one, two or three elements independently selected from N, O, S, S(O) and S(O)$_2$; each ring optionally substituted with one or two substituents independently selected from HO—, O=, NC—, halogen, $R^{1.1}$, $R^{1.1}$O—, $R^{1.1}$—(O)C—, $R^{1.2}$—, $R^{1.5.4}$, $R^{1.5.5}$ and $R^{1.5.6}$ or two substituents are together $R^{1.5.7}$;

or two $R^{1.5}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and S(O)$_2$; optionally substituted with one or two substituents, independently selected from among HO—, F, O=, NC—, $R^{1.1}$, $R^{1.1}$O—, $R^{1.1}$—(O)C—, $R^{1.2}$—, $R^{1.2}$—, $R^{1.5.4}$, $R^{1.5.5}$ and $R^{1.5.6}$, phenyl and a five- or six-membered heterocyclic or heteroaryl ring containing one, two or three elements independently selected from among N, O, S, S(O) and S(O)$_2$; or two substituents are together $R^{1.5.7}$;

Embodied are above compounds of formula 1, wherein $R^1$ is $R^{1.d}$ and $R^{1.d}$ is phenyl; optionally substituted with one or two substituents independently selected from the group consisting of halogen, NC— and $R^{1.5}R^{1.5}$N(O)C—; and $R^{1.5}$ is independently selected from the group consisting of H, $R^{1.1}$, $R^{1.2}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from $R^{1.5.1}$—, $R^{1.5.2}$— and $R^{1.5.3}$—;

$R^{1.5.1}$ is selected from the group consisting of HO—, halogen, NC—, $R^{1.1}$O—, $R^{1.5.4}$, $R^{1.5.5}$ and $R^{1.5.6}$; or $R^{1.5.2}$ denotes a four-membered heterocyclic ring containing one element independently selected from among N, O, S, S(O) and S(O)$_2$; or $R^{1.5.3}$ denotes a five- or six-membered heterocyclic or heteroaryl ring containing one, two or three elements independently selected from among N, O, S, S(O) and S(O)$_2$; each of the rings optionally substituted with one or two substituents independently selected from among HO—, O=, halogen, NC—, $R^{1.1}$, $R^{1.1}$O—, $R^{1.1}$—(O)C—, HO—$C_{1-6}$-alkyl- or $R^{1.1}$—O—$C_{1-6}$-alkyl-, $R^{1.5.4}$, $R^{1.5.5}$ and $R^{1.5.6}$ or two substituents are together $R^{1.5.7}$;

$R^{1.5.4}$ is independently selected from the group consisting of H$_2$N—, $R^{1.1}$—HN—, $(R^{1.1})_2$N—, $R^{1.1}$—(O)C—HN— and $R^{1.1}$—(O)C—$(R^{1.1})$N—;

$R^{1.5.5}$ is independently selected from the group consisting of $R^{1.1}$—(O)S—, $R^{1.1}$—(O)$_2$S—, $R^{1.1}$(HN)S—, $R^{1.1}$(HN)(O)S—, $R^{1.1}(R^{1.1}$N)S—, $R^{1.1}(R^{1.2}$N)S—, $R^{1.1}(R^{1.1}$N)(O)S—, $R^{1.1}(R^{1.2}$N)(O)S—, $R^{1.1}$(NC—N)S— and $R^{1.1}$(NC—N)(O)S—;

$R^{1.5.6}$ is independently selected from the group consisting of HO(O)C—, H$_2$N(O)C—, $R^{1.1}$—O—(O)C—, $R^{1.1}$—NH—(O)C— and $(R^{1.1})_2$N—(O)C—;

$R^{1.5.7}$ is independently selected from the group consisting of $C_{1-6}$-alkylene and $C_{1-6}$-haloalkylene, wherein optionally one or two CH$_2$-groups are replaced by —HN—, —$(R^{1.1})$N—, —$(R^{1.1}$(O)C—)N—, —O—, —S—, —S(O)— or —S(O)$_2$—.

Embodied are above compounds of formula 1, wherein $R^1$ is $R^{1.e}$ and $R^{1.e}$ is phenyl or pyridinyl, preferably phenyl; each ring optionally substituted with one or two substituents independently selected from the group consisting of F—, Cl—, Br—, NC—, $R^{1.1}$, $R^{1.2}$, $R^{1.3}$, $R^{1.1}$(O)S— and $R^{1.1}$(O)$_2$S—; and $R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{1.2}$ is HO—$C_{1-6}$-alkyl- or $R^{1.1}$—O—$C_{1-6}$-alkyl-;

$R^{1.3}$ is a five-membered heterocyclic or heteroaryl ring, wherein one, two or three elements are replaced by an element independently selected from the group consisting of N, O, S, S(O) and S(O)$_2$; each ring optionally substituted with one, two or three substituents independently selected from the group consisting of halogen, NC—, HO—, O=, $R^{1.1}$, $R^{1.1}$O—, $R^{1.1}$—(O)C—, $R^{1.1}$(O)$_2$S—, $R^{1.1}$—O—(O)C—, $R^{1.1}$—NH—(O)C— and $(R^{1.1})_2$N—(O)C—.

Embodied are above compounds of formula 1, wherein $R^1$ is $R^{1.f}$ and $R^{1.f}$ is phenyl; optionally substituted with one or two substituents independently selected from the group consisting of F—, Cl—, Br—, NC—, $C_{1-6}$-alkyl-, $C_{1-6}$-haloalkyl-, HO $C_{1-6}$ alkyl, $R^{1.3}$, $C_{1-6}$-alkyl-(O)S— and $C_{1-6}$-alkyl-$(O)_2$S—; and $R^{1.3}$ is a five-membered heterocyclic or heteroaryl ring, wherein one, two or three elements are replaced by an element independently selected from the group consisting of N, O, S, S(O) and $S(O)_2$; each ring optionally substituted with one or two substituents independently selected from the group consisting of halogen, NC—, HO—, O═, $C_{1-6}$-alkyl-, $C_{1-6}$-haloalkyl- and $C_{1-6}$-alkyl-O—.

Embodied are above compounds of formula 1, wherein $R^1$ is $R^{1.g}$ and $R^{1.g}$ is phenyl; optionally substituted with one or two substituents independently selected from the group consisting of F—, Cl—, Br—, NC—, methyl, ethyl, propyl, isopropyl, cyclopropyl, $CF_3$—, $CF_2H$—, HO—$(CH_2)$—, HO—$(CH_2)_2$—, Me(O)S—, Et(O)S, $Me(O)_2$S— and $Et(O)_2$S—.

Embodied are above compounds of formula 1, wherein $R^1$ is $R^{1.h}$ and $R^{1.h}$ is phenyl; optionally substituted with one or two substituents independently selected from the group consisting of Br, NC—, $CF_3$— and HO—$(CH_2)$.

Embodied are above compounds of formula 1, wherein $R^{1.i}$ is R and $R^{1.i}$ is phenyl; optionally substituted with one or two substituents independently selected from the group consisting of NC— and $R^{1.3}$; and $R^{1.3}$ is a five-membered heteroaryl ring, wherein one, two or three elements are replaced by an element independently selected from the group consisting of N, O and S; each ring optionally substituted with one or two substituents independently selected from the group consisting of halogen, NC—, HO—, O═, $C_{1-6}$-alkyl-, $C_{1-6}$-haloalkyl- and $C_{1-6}$-alkyl-O—.

Embodied are above compounds of formula 1, wherein $R^1$ is $R^{1.j}$ and $R^{1.j}$ is phenyl; optionally substituted with one or two substituents independently selected from the group consisting of NC— and $R^{1.3}$; and $R^{1.3}$ is a five-membered heteroaryl ring, wherein one, two or three elements are replaced by an element independently selected from the group consisting of N, O and S; each ring optionally substituted with one or two substituents independently selected from the group consisting of F, Cl, Br, NC—, HO—, O═, methyl, ethyl, isopropyl, cyclopropyl, $CF_3$— and $CF_2H$—.

Embodied are above compounds of formula 1, wherein $R^1$ is $R^{1.k}$ and $R^{1.k}$ is phenyl; optionally substituted with one or two substituents independently selected from the group consisting of NC— and $R^{1.3}$; and $R^{1.3}$ is a five-membered heteroaryl ring, wherein one, two or three elements are replaced by an element independently selected from the group consisting of N and O; each ring optionally substituted with methyl.

Embodied are above compounds of formula 1, wherein $R^1$ is $R^{1.l}$ and $R^{1.l}$ is phenyl; optionally substituted with one or two substituents independently selected from the group consisting of NC— and $R^{1.3}$; and $R^{1.3}$ is a five- or six membered heteroaryl ring, wherein one, two or three elements are replaced by an element independently selected from the group consisting of N and O; each ring optionally substituted with methyl.

Embodied are above compounds of formula 1, wherein $R^1$ is $R^{1.l}$ and $R^{1.l}$ is phenyl substituted with NC—, Embodied are above compounds of formula 1, wherein $R^1$ is $R^{1.l}$ and $R^{1.l}$ is

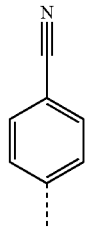

Embodied are above compounds of formula 1, wherein $R^1$ is $R^{1.m}$ and $R^{1.m}$ is

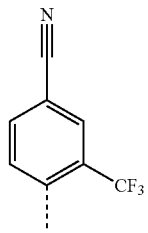

Embodied are above compounds of formula 1, wherein $R^1$ is $R^{1.n}$ and $R^{1.n}$ is

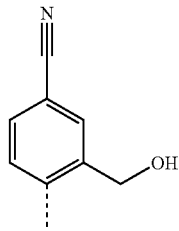

Embodied are above compounds of formula 1, wherein $R^1$ is $R^{1.o}$ and $R^{1.o}$ is

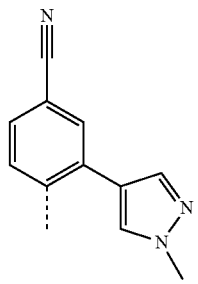

Embodied are above compounds of formula 1, wherein $R^1$ is $R^{1.p}$ and $R^{1.p}$ is

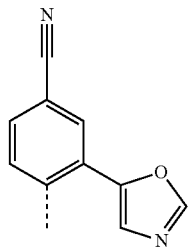

Embodied are above compounds of formula 1, wherein $R^1$ is $R^{1.q}$ and $R^{1.q}$ is

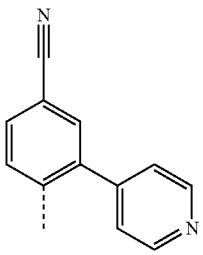

Embodied are above compounds of formula 1, wherein $R^1$ is $R^{1.r}$ and $R^{1.r}$ is

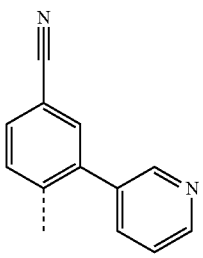

Embodied are above compounds of formula 1, wherein $R^1$ is $R^{1.s}$ and $R^{1.s}$ is

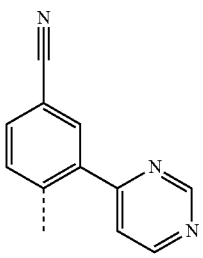

Embodied are above compounds of formula 1, wherein $R^1$ is $R^{1.t}$ and $R^{1.t}$ is

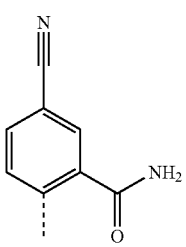

Embodied are above compounds of formula 1, wherein $R^1$ is $R^{1.u}$ and $R^{1.u}$ is

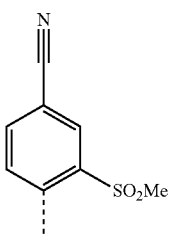

Embodied are above compounds of formula 1, wherein $R^1$ is $R^{1.v}$ and $R^{1.v}$ is

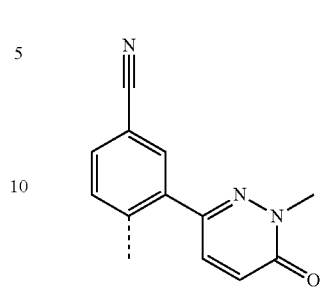

Embodied are above compounds of formula 1, wherein $R^2$ is $R^{2.a}$ and $R^{2.a}$ is phenyl or pyridinyl; each ring optionally substituted with one or two substituents independently selected from halogen, $C_{1-4}$-alkyl- and $C_{1-4}$-haloalkyl-;

Embodied are above compounds of formula 1, wherein $R^2$ is $R^{2.a}$ and $R^{2.a}$ is phenyl; optionally substituted with one or two substituents independently selected from halogen, $C_{1-4}$-alkyl- and $C_{1-4}$-haloalkyl-.

Embodied are above compounds of formula 1, wherein $R^2$ is $R^{2.b}$ and $R^{2.b}$ is phenyl or pyridinyl; each ring optionally substituted with one or two substituents independently selected from F, $CF_3$— or $CF_2H$—.

Embodied are above compounds of formula 1, wherein $R^2$ is $R^{2.b}$ and $R^{2.b}$ is phenyl; optionally substituted with one or two substituents independently selected from F, $CF_3$— and $CF_2H$—.

Embodied are above compounds of formula 1, wherein $R^2$ is $R^{2.c}$ and $R^{2.c}$ is phenyl or pyridinyl; each ring optionally substituted with $CF_3$— or $CF_2H$—.

Embodied are above compounds of formula 1, wherein $R^2$ is $R^{2.c}$ and $R^{2.c}$ is phenyl; optionally substituted with $CF_3$— or $CF_2H$—.

Embodied are above compounds of formula 1, wherein $R^2$ is $R^{2.c}$ and $R^{2.c}$ is pyridinyl; optionally substituted with $CF_3$— or $CF_2H$—.

Embodied are above compounds of formula 1, wherein $R^2$ is $R^{2.d}$ and $R^{2.d}$ is

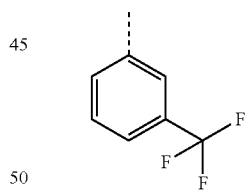

Embodied are above compounds of formula 1, wherein $R^2$ is $R^{2.e}$ and $R^{2.e}$ is

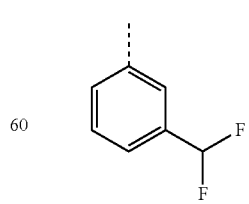

Embodied are above compounds of formula 1, wherein $R^3$ is $R^{3.a}$ and $R^{3.a}$ is a residue independently selected from the group consisting of $R^{3.1}$—;
$R^{3.2}O(O)C$—;
$R^{3.2}O(O)C$-A-; preferably $R^{3.2}O(O)C$—$CH_2$—;
$R^{3.2}(O)_2S$—;
$(R^{3.2})_2N(O)C$ and
$(R^{3.2})_2N(O)C$-A-; preferably $(R^{3.2})_2N(O)C$—$CH_2$—;

$R^{3.1}$ is independently selected from the group consisting of H, $R^{3.3}$, $R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from $R^{3.1.1}$—;

$R^{3.1.1}$ is selected from the group consisting of HO—, halogen, NC—, $R^{3.3}O$—, $R^{3.5}$, $R^{3.6}$ and $R^{3.7}$ or $R^{3.1.1}$ denotes a ring independently selected from phenyl and a four-membered heterocyclic ring containing one element independently selected from among N, O, S, S(O) and S(O)$_2$ or $R^{3.1.1}$ denotes a five- or six-membered heterocyclic or heteroaryl ring containing one, two or three elements independently selected from among N, O, S, S(O) and S(O)$_2$;

each of the rings optionally substituted with one or two substituents independently selected from among HO—, O═, halogen, NC—, $R^{3.3}$, $R^{3.3}O$—, $R^{3.3}$—(O)C—, $R^{3.4}$, $R^{3.5}$, $R^{3.6}$ and $R^{3.7}$ or two substituents are together $R^{3.8}$;

$R^{3.2}$ is independently selected from $R^{3.1}$, phenyl or a five- or six-membered heterocyclic or heteroaryl ring containing one, two or three elements independently selected from N, O, S, S(O) and S(O)$_2$; each ring optionally substituted with one or two substituents independently selected from HO—, O═, NC—, halogen, $R^{3.3}$, $R^{3.3}O$—, $R^{3.3}$—(O)C—, $R^{3.4}$, $R^{3.5}$, $R^{3.6}$ and $R^{3.7}$ or two substituents are together $R^{3.8}$;

or two $R^{3.2}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and S(O)$_2$; optionally substituted with one or two substituents, independently selected from among HO—, F, O═, NC—, $R^{3.3}$, $R^{3.3}O$—, $R^{3.3}$—(O)C—, $R^{3.4}$, $R^{3.5}$, $R^{3.6}$, $R^{3.7}$, phenyl and a five- or six-membered heterocyclic or heteroaryl ring containing one, two or three elements independently selected from among N, O, S, S(O) and S(O)$_2$; or two substituents are together $R^{3.8}$;

$R^{3.3}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{3.4}$ is HO—$C_{1-6}$-alkyl- or $R^{3.3}$—O—$C_{1-6}$-alkyl-;

$R^{3.5}$ is independently selected from the group consisting of $H_2N$—, $R^{3.3}$—HN—, $(R^{3.3})_2N$—, $R^{3.3}$—(O)C—HN— and $R^{3.3}$—(O)C—$(R^{3.3})N$—;

$R^{3.6}$ is independently selected from the group consisting of $R^{3.3}$—(O)S—, $R^{3.3}$—(O)$_2$S—, $R^{3.3}$(HN)S—, $R^{3.3}$(HN)(O)S—, $R^{3.3}(R^{3.3}N)S$—, $R^{3.3}(R^{3.3}N)(O)S$—, $R^{3.3}(R^{3.4}N)S$—, $R^{3.3}(R^{3.4}N)(O)S$—; $R^{3.3}$(NC—N)S— and $R^{3.3}$(NC—N)(O)S—;

$R^{3.7}$ is independently selected from the group consisting of HO(O)C—, $H_2N(O)C$—, $R^{3.3}$—O—(O)C—, $R^{3.3}$—NH—(O)C— and $(R^{3.3})_2N$—(O)C—;

$R^{3.8}$ is independently selected from the group consisting of $C_{1-6}$-alkylene and $C_{1-6}$-haloalkylene, wherein optionally one or two CH$_2$-groups are replaced by —HN—, —$(R^{3.3})N$—, —$(R^{3.4})N$—, —$(R^{3.3}(O)C$—)N—, —$(R^{3.4}(O)C$—)N—, —O—, —S—, —S(O)— or —S(O)$_2$—;

A is —$CH_2$—, —$CH_2$—$CH_2$— or —$CH_2$—$CH_2$—$CH_2$—; preferably —$CH_2$—; optionally substituted with one or two substituents independently selected from the group consisting of halogen, $R^{3.3}$, $R^{3.3}O$— and $R^{3.4}$ or two substituents together are $R^{3.8}$.

Embodied are above compounds of formula 1, wherein $R^3$ is $R^{3.b}$ and $R^{3.b}$ is a residue independently selected from the group of $R^{3.1}$.

Embodied are above compounds of formula 1, wherein $R^3$ is $R^{3.c}$ and $R^{3.c}$ is a residue independently selected from H, $C_{1-6}$-alkyl-, $C_{3-6}$-cycloalkyl-, $C_{1-6}$-haloalkyl-, $C_{3-6}$-halocycloalkyl; HO—$C_{1-6}$-alkyl- and $C_{1-6}$-alkyl-O—$C_{1-6}$-alkyl-; each optionally substituted with one or two substituents independently selected from HO—, halogen and NC—.

Embodied are above compounds of formula 1, wherein $R^3$ is $R^{3.d}$ and $R^{3.d}$ is a residue independently selected from H, methyl, ethyl, propyl and HO—$(CH_2)_2$—.

Embodied are above compounds of formula 1, wherein $R^3$ is $R^{3.e}$ and $R^{3.e}$ is methyl.

Embodied are above compounds of formula 1, wherein $R^3$ is $R^{3.f}$ and $R^{3.f}$ is H.

Embodied are above compounds of formula 1, wherein $R^3$ is $R^{3.g}$ and $R^{3.g}R^{3.2}(O)_2S$—.

Embodied are above compounds of formula 1, wherein $R^3$ is $R^{3.h}$ and $R^{3.h}R^{3.1}(O)_2S$—.

Embodied are above compounds of formula 1, wherein $R^3$ is $R^{3.i}$ and $R^{3.i}$ is $R^{3.1}(O)_2S$—; and $R^{3.1}$ is independently selected from the group consisting of $C_{1-6}$-alkyl-, $C_{3-6}$-cycloalkyl-, $C_{1-6}$-haloalkyl-, $C_{3-6}$-halocycloalkyl, HO—$C_{1-6}$-alkyl- and $C_{1-6}$-alkyl-O—$C_{1-6}$-alkyl-; each optionally substituted with one or two substituents independently selected from HO—, halogen, NC—, $C_{1-6}$-alkyl-O— and $C_{1-6}$-alkyl-(O)$_2$S—.

Embodied are above compounds of formula 1, wherein $R^3$ is $R^{3.j}$ and $R^{3.j}$ is a residue independently selected from the group of $C_{1-6}$-alkyl-(O)$_2$S—, $C_{3-6}$-cycloalkyl-(O)$_2$S—, HO—$C_{1-6}$-alkyl-(O)$_2$S— and $C_{1-6}$-alkyl-O—$C_{1-6}$-alkyl-(O)$_2$S—.

Embodied are above compounds of formula 1, wherein $R^3$ is $R^{3.k}$ and $R^{3.k}$ is methyl-(O)$_2$S— or ethyl-(O)$_2$S—.

Embodied are above compounds of formula 1, wherein $R^3$ is $R^{3.l}$ and $R^{3.l}$ is $(R^{3.2})_2N(O)C$—.

Embodied are above compounds of formula 1, wherein $R^3$ is $R^{3.m}$ and $R^{3.m}$ is $(R^{3.2})_2N(O)C$; and $R^{3.2}$ is independently selected from H, $C_{1-6}$-alkyl-, $C_{3-6}$-cycloalkyl-, $C_{1-6}$-haloalkyl-, $C_{3-6}$-halocycloalkyl, HO—$C_{1-6}$-alkyl-, $C_{1-6}$-alkyl-O—$C_{1-6}$-alkyl-, $C_{1-6}$-alkyl-$C_{3-6}$-cycloalkyl- and $C_{3-6}$-cycloalkyl-$C_{1-6}$-alkyl-; each optionally substituted with one or two substituents independently selected from HO—, halogen, NC—, $C_{1-6}$-alkyl-O—, $H_2N$—, $C_{1-6}$-alkyl-HN—, $(C_{1-6}$-alkyl)$_2N$—, $C_{1-6}$-alkyl-(O)C—HN—, $C_{1-6}$-alkyl-(O)C—$(C_{1-6}$-alkyl)N—, $C_{1-6}$-alkyl-(O)S—, $C_{1-6}$-alkyl-(O)$_2$S—, $C_{1-6}$-alkyl-(HN)S—, $C_{1-6}$-alkyl-(HN)(O)S—, $C_{1-6}$-alkyl($C_{1-6}$-alkyl-N)S—, $C_{1-6}$-alkyl-($C_{1-6}$-alkyl-N)(O)S—, $C_{1-6}$-alkyl-(NC—N)S—, $C_{1-6}$-alkyl-(NC—N)(O)S—, HO(O)C—, $H_2N(O)C$—, $C_{1-6}$-alkyl-NH—(O)C— and $(C_{1-6}$-alkyl)$_2$N—(O)C—;

Embodied are above compounds of formula 1, wherein $R^3$ is $R^{3.n}$ and $R^{3.n}$ is $(R^{3.2})_2N(O)C$ and $R^{3.2}$ is independently selected from H, $C_{1-6}$-alkyl- and HO—$C_{1-6}$-alkyl-; each optionally substituted with one or two substituents independently selected from HO—, NC— and $C_{1-6}$-alkyl-O—.

Embodied are above compounds of formula 1, wherein $R^3$ is $R^{3 \cdot o}$ and $R^{3 \cdot o}$ is $(R^{3.2})_2N(O)C$ and $R^{3.2}$ is independently selected from H, methyl, ethyl, propyl, isopropyl, MeO—$(CH_2)_2$—, HO—$(CH_2)_2$— and HO—$(CMe_2)$-$(CH_2)$—.

Embodied are above compounds of formula 1, wherein $R^3$ is $R^{3 \cdot p}$ and $R^{3 \cdot p}$ is $(R^{3.2})_2N(O)C$ and $R^{3.2}$ is independently selected from H, methyl and HO—$(CH_2)_2$—.

Embodied are above compounds of formula 1, wherein $R^3$ is $R^{3 \cdot q}$ and $R^{3 \cdot q}$ is
$(R^{3.2})_2N(O)C$-A-; preferably $(R^{3.2})_2N(O)C$—$CH_2$—; and
$R^{3.2}$ is independently selected from $R^{3.1}$, phenyl or a five- or six-membered heterocyclic or heteroaryl ring containing one, two or three elements independently selected from N, O, S, S(O) and $S(O)_2$; each ring optionally substituted with one or two substituents independently selected from HO—, O=, NC—, halogen, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$;
or two $R^{3.2}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and $S(O)_2$; optionally substituted with one or two substituents, independently selected from among HO—, F, O=, NC—, $R^{3.3}$, $R^{3.3}$O—, $R^{3.3}$—(O)C—, $R^{3.4}$, $R^{3.5}$, $R^{3.6}$, $R^{3.7}$, phenyl and a five- or six-membered heterocyclic or heteroaryl ring containing one, two or three elements independently selected from among N, O, S, S(O) and $S(O)_2$; or two substituents are together $R^{3.8}$.

Embodied are above compounds of formula 1, wherein $R^3$ is $R^{3 \cdot r}$ and $R^{3 \cdot r}$ is
$(R^{3.2})_2N(O)C$—$CH_2$—; and
$R^{3.2}$ is independently selected from H, $C_{1-6}$-alkyl-, HO—$C_{1-6}$-alkyl-, $C_{1-6}$-alkyl-O—$C_{1-6}$-alkyl-, $C_{1-6}$-alkyl-(O)S—$C_{1-6}$-alkyl-; or two $R^{3.2}$ are together a five- or six-membered monocyclic or a six- or eight-membered bicyclic heterocyclic or heteroaryl ring optionally containing additional to the nitrogen one or two elements independently selected from among N, O, S and $S(O)_2$; optionally substituted with one or two substituents independently selected from among $C_{1-6}$-alkyl-, F— and $C_{1-6}$-alkyl-O—.

Embodied are above compounds of formula 1, wherein $R^3$ is $R^{3 \cdot s}$ and $R^{3 \cdot s}$ is
$(R^{3.2})_2N(O)C$—$CH_2$—; and
$R^{3.2}$ is independently selected from H, methyl, ethyl, propyl, cyclopropyl, isopropyl, HO—$(CH_2)_2$—, HO—$(CH_2)_3$—, MeO—$(CH_2)_2$—, MeO—$(CH_2)_3$—, Me(O)S—$(CH_2)_2$— and Me(O)S—$(CH_2)_3$—; or two $R^{3.2}$ are together a five- or six-membered monocyclic or a six- or eight-membered bicyclic heterocyclic or heteroaryl ring optionally containing additional to the nitrogen one or two elements independently selected from among N, O, S and $S(O)_2$; optionally substituted with one or two substituents independently selected from among methyl, F and MeO—.

Embodied are above compounds of formula 1, wherein $R^3$ is $R^{3 \cdot t}$ and $R^{3 \cdot t}$ is
$(R^{3.2})_2N(O)C$—$CH_2$—; and
$R^{3.2}$ is independently selected from H, methyl, ethyl, HO—$(CH_2)_2$—, MeO—$(CH_2)_2$— and Me(O)S—$(CH_2)_2$—. or two $R^{3.2}$ are together a five- or six-membered monocyclic or a six- or eight-membered bicyclic heterocyclic or heteroaryl ring optionally containing additional to the nitrogen one or two elements independently selected from among N, O, S and $S(O)_2$; optionally substituted with one or two substituents independently selected from among methyl-, F— and MeO—.

Embodied are above compounds of formula 1, wherein $R^4$ is $R^{4 \cdot a}$ and $R^{4 \cdot a}$ is $R^3$.

Embodied are above compounds of formula 1, wherein $R^4$ is $R^{4 \cdot b}$ and $R^{4 \cdot b}$ is selected from H, $R^{3.3}$, $R^{3.4}$ and $R^{3.7}$.

Embodied are above compounds of formula 1, wherein $R^4$ is $R^{4 \cdot c}$ and $R^{4 \cdot c}$ is independently selected from H, $C_{1-6}$-alkyl-, $C_{3-6}$-cycloalkyl-, $C_{1-6}$-haloalkyl-, $C_{3-6}$-halocycloalkyl, HO—$C_{1-6}$-alkyl-, $C_{1-6}$-alkyl-O—$C_{1-6}$-alkyl-, HO(O)C—, $H_2N(O)C$—, $C_{1-6}$-alkyl-O—(O)C—, $C_{1-6}$-alkyl-NH—(O)C—, HO—$C_{1-6}$-alkyl-NH—(O)C— and $(C_{1-6}$-alkyl$)_2N$—(O)C—.

Embodied are above compounds of formula 1, wherein $R^4$ is $R^{4 \cdot d}$ and $R^{4 \cdot d}$ is independently selected from H, $C_{1-6}$-alkyl-, $C_{1-6}$-alkyl-NH—(O)C— and HO—$C_{1-6}$-alkyl-NH—(O)C—.

Embodied are above compounds of formula 1, wherein $R^4$ is $R^{4 \cdot e}$ and $R^{4 \cdot e}$ is H, methyl, ethyl-NH—(O)—C—, $HO(CH_2)_2NH$—(O)—C— and $HO(CH_2)_3NH$—(O)—C—.

Embodied are above compounds of formula 1, wherein $R^4$ is $R^{4 \cdot f}$ and $R^{4 \cdot f}$ is H or methyl.

Embodied are above compounds of formula 1, wherein $R^4$ is $R^{4 \cdot g}$ and $R^{4 \cdot g}$ is H.

Embodied are above compounds of formula 1, wherein $R^5$ and $R^6$ are independently from each other $R^{5 \cdot a}$ and $R^{5 \cdot a}$ is independently selected from H, $C_{1-6}$-alkyl-, $C_{3-6}$-cycloalkyl-, $C_{1-6}$-haloalkyl-, $C_{3-6}$-halocycloalkyl-, HO—$C_{1-6}$-alkyl- and $C_{1-6}$-alkyl-O—$C_{1-6}$-alkyl-; or two $R^{5 \cdot a}$ are together $C_{1-6}$-alkylene or $C_{1-6}$-haloalkylene, wherein optionally one $CH_2$-group can be replaced by —O—, —S—, —S(O)— or —$S(O)_2$—.

Embodied are above compounds of formula 1, wherein $R^5$ and $R^6$ are independently from each other $R^{5 \cdot b}$ and $R^{5 \cdot b}$ is independently selected from H, $C_{1-6}$-alkyl-, $C_{3-6}$-cycloalkyl-, $C_{1-6}$-haloalkyl-, $C_{3-6}$-halocycloalkyl-, HO—$C_{1-6}$-alkyl- and $C_{1-6}$-alkyl-O—$C_{1-6}$-alkyl-.

Embodied are above compounds of formula 1, wherein $R^5$ and $R^6$ are independently from each other $R^{5 \cdot c}$ and $R^{5 \cdot c}$ is independently selected from H, methyl, ethyl, propyl, isopropyl and cyclopropyl.

Embodied are above compounds of formula 1, wherein $R^5$ and $R^6$ are independently from each other $R^{5 \cdot d}$ and $R^{5 \cdot d}$ is methyl.

Embodied are above compounds of formula 1, wherein $R^5$ and $R^6$ are independently from each other $R^{5 \cdot e}$ and $R^{5 \cdot e}$ is H.

Embodied of all of the above mentioned embodiments of the invention is a compound of formula 1, wherein the configuration of formula 1 is according to formula 1'

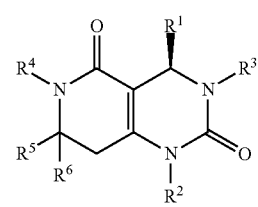

or a pharmaceutically acceptable salt thereof.

Embodied are the compounds of formula 1, wherein the compounds are selected from the group consisting of examples 1, 1a, 2, 2a, 3, 4, 4a, 5, 6, 7, 8a, 9, 10, 11, 12, 12a, 12.1, 12.2, 12.3, 12.4, 12.5, 12.6, 12.7, 12.8, 12.9, 13, 14, 15, 15.1, 15.2, 15.3, 15.4, 15.5, 15.6, 16, 17, 18, 19, 20, 21, 22, 23, 24, 25, 26, 27, 28, 29, 30a, 31a, 32a, 33, 34, 35, 36, 36.1, 36.2, 36.3, 37, 38, 39, 39.1, 39.2, 40 and 41.

Embodied are the compounds of formula 1, wherein the compounds are selected from the group consisting of examples 1a, 2a, 4a, 6, 8a, 9, 30a, 31a, 32a, 34, 35, 36, 36.1, 36.2, 36.3, 37, 38, 39, 39.1, 39.2, 40 and 41.

Embodied are the compounds of formula 1, wherein the compounds are selected from the group consisting of examples 1a, 2a, 4a, 6, 8a, 9, 30a, 31a, 32a, 35, 36, 36.1, 36.2, 36.3, 37, 38, 39, 39.1, 39.2 and 41.

Embodied are the compounds of formula 1, wherein the compounds are selected from the group consisting of examples 1a, 2a, 4a, 6, 8a, 9, 30a, 31a, 35, 36, 37, 39, 39.1, 40 and 41.

Embodied are the compounds of formula 1, wherein the compounds are selected from the group consisting of examples 1a, 30a, 31a, 32a, 36 and 37.

Embodied are the compounds of formula 1, wherein the compounds are selected from the group consisting of examples 1a, 8a, 30a, 31a, 32a, 34, 35, and 40.

Any and each other of the definitions of $R^1$, $R^{1.1}$, $R^{1.2}$, $R^{1.3}$, $R^{1.3.1}$, $R^{1.3.2}$, $R^{1.3.3}$, $R^{1.4}$, $R^{1.5}$, $R^{1.5.1}$, $R^{1.5.2}$, $R^{1.5.3}$, $R^{1.5.4}$, $R^{1.5.5}$, $R^{1.5.6}$, $R^{1.5.7}$, $R^2$, $R^3$, $R^{3.1}$, $R^{3.2}$, $R^{3.3}$, $R^{3.4}$, $R^{3.5}$, $R^{3.6}$, $R^{3.7}$, $R^{3.8}$, $R^4$, $R^5$, $R^6$ and A may be combined with each other.

A further embodiment of the invention is a process for the preparation of compounds of general formula 1, characterized in that the process comprises the preparation of intermediates of general formula C1a,

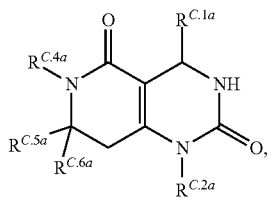

C.1a optionally in the form of the tautomers thereof; wherein the process comprises the reaction A, wherein A is the reaction of a compound of formula C2 with a compound of formula C3, to form a compound of formula C.1a,

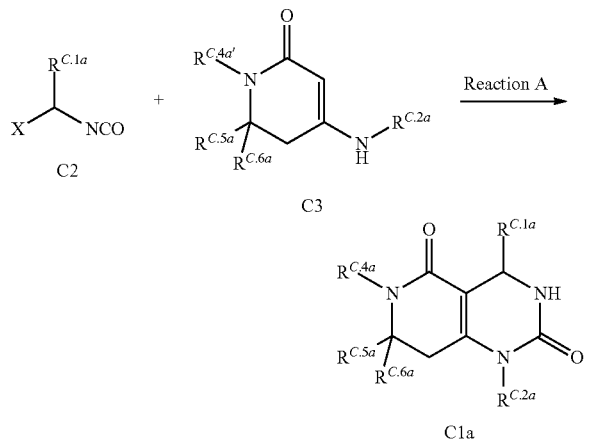

wherein
$R^{C.1a}$ is phenyl; optionally substituted with one or two substituents independently selected from the group consisting of F, Cl, Br, NC—, methyl, ethyl, $CF_2H$—, $CF_3$—, MeO—, EtO—, $CF_3O$—, methyl-(O)S—, ethyl-(O)S—, methyl-$(O)_2S$— and ethyl-$(O)_2S$—; preferably phenyl, optionally substituted with one or two substituents independently selected from the group consisting of Br, NC— and $CF_3$—;

$R^{C.2a}$ is phenyl; optionally substituted with one or two substituents independently selected from F—, $CF_3$— and $CF_2H$—;

$R^{C.4a'}$ is H, $C_{1-6}$-alkyl- or $C_{1-6}$-alkyl-O(O)C—;

$R^{C.4a}$ is H or $C_{1-6}$-alkyl-;

$R^{C.5a}$ is independently selected from H and $C_{1-6}$-alkyl-;

$R^{C.6a}$ is independently selected from H and $C_{1-6}$-alkyl-; and

X is halogen;

Another embodiment of the invention is a process for the preparation of compounds of general formula 1, characterized in that the process comprises the preparation of intermediates of general formula C1a,

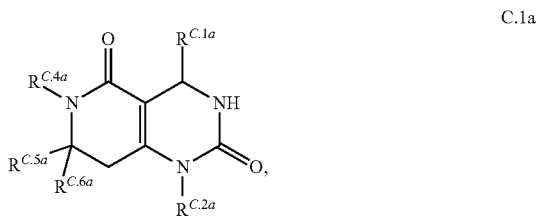

C.1a optionally in the form of the tautomers thereof; wherein the process comprises the reaction A, wherein A is the reaction of a compound of formula C2 with a compound of formula C3, to form a compound of formula C.1a,

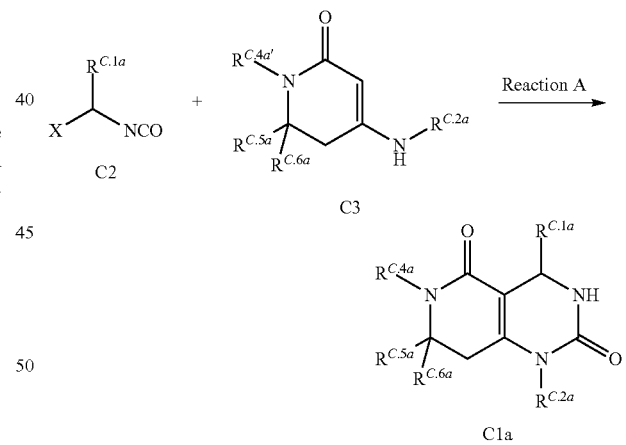

wherein
$R^{C.1a}$ is phenyl, optionally substituted with one or two substituents independently selected from the group consisting of Br, NC— or $CF_3$—;

$R^{C.2a}$ is phenyl; optionally substituted with one substituent independently selected from $CF_3$— and $CF_2H$—;

$R^{C.4a'}$ is H, methyl or tert-butyl-O(O)C—;

$R^{C.4a}$ is H or methyl;

$R^{C.5a}$ is H or methyl;

$R^{C.6a}$ is H or methyl;

X is Cl;

A further embodiment of the invention are compounds of formula C2,

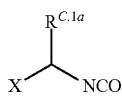

C2 or a pharmaceutically acceptable salt thereof, optionally in the form of the tautomers thereof, useful for the preparation of compounds of general formula C1a, wherein
$R^{C.1a}$ is

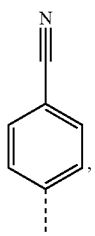

optionally substituted with one additional substituent independently selected from Br and $CF_3$; and
X is Cl;

Another embodiment of the invention are compounds of formula C2,

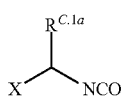

C2 or a pharmaceutically acceptable salt thereof, optionally in the form of the tautomers thereof, useful for the preparation of compounds of general formula C1a, wherein
$R^{C.1a}$ is

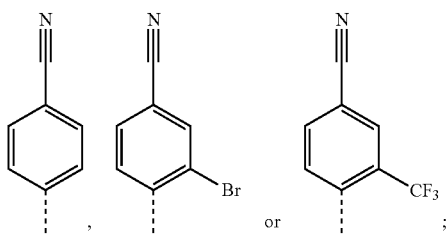

and
X is Cl.

A further embodiment of the invention are compounds of formula C3,

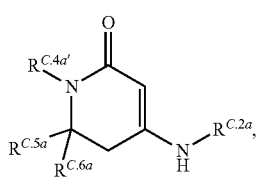

C3 or a pharmaceutically acceptable salt thereof, optionally in the form of the tautomers thereof, useful for the preparation of compounds of general formula C.1a, wherein
$R^{C.2a}$ is phenyl; optionally substituted with one or two substituents independently selected from F—, $CF_3$— and $CF_2H$—;
$R^{C.4a'}$ H, $C_{1-6}$-alkyl- or $C_{1-6}$-alkyl-O(O)C—;
$R^{C.5a}$ H or $C_{1-6}$-alkyl-; and
$R^{C.6a}$ H or $C_{1-6}$-alkyl-;

A further embodiment of the invention are compounds of formula C3,

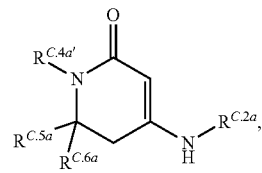

C3 or a pharmaceutically acceptable salt thereof, optionally in the form of the tautomers thereof, useful for the preparation of compounds of general formula C.1a,
wherein
$R^{C.2a}$ is

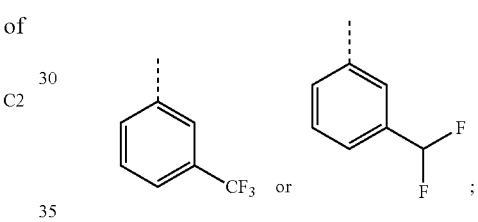

$R^{C.4a'}$ H, methyl or tert-butyl-O(O)C—;
$R^{C.5a}$ is H or methyl; and
$R^{C.6a}$ is H or methyl;

A further embodiment of the invention is a process for the preparation of compounds of general formula 1, characterized in that the process comprises the preparation of compounds of general formula C4,

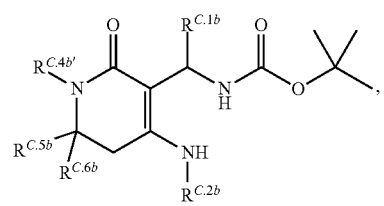

C4 optionally in the form of the tautomers thereof; characterized in that the process comprises the reaction B, wherein B is the reaction of a compound of formula C5 with a compound of formula C6, to form a compound of formula C4,

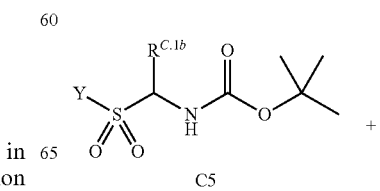

+

C5

-continued

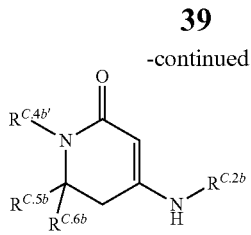

C6

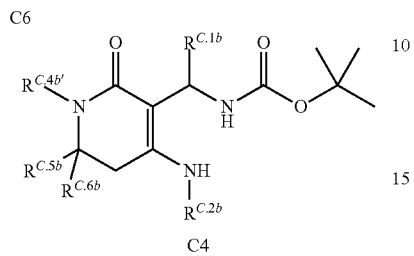

C4 wherein $R^{C.1b}$ is phenyl; optionally substituted with one or two substituents independently selected from the group consisting of F, Cl, Br, NC—, methyl, ethyl, $CF_2H$—, $CF_3$—, MeO—, EtO—, $CF_3O$—, methyl-(O)S—, ethyl-(O)S—, methyl-$(O)_2$S— and ethyl-$(O)_2$S—;

$R^{C.2b}$ is phenyl; optionally substituted with one or two substituents independently selected from F—, $CF_3$— and $CF_2H$—;

$R^{C.4b'}$ is H, $C_{1-6}$-alkyl- or $C_{1-6}$-alkyl-O(O)C—;

$R^{C.5b}$ is independently selected from H and $C_{1-6}$-alkyl-;

$R^{C.6b}$ is independently selected from H and $C_{1-6}$-alkyl-; and

Y is phenyl, optionally substituted with one or two substituents independently selected from the group consisting of halogen, NC—, $O_2N$—, $C_{1-6}$-alkyl-, $C_{1-6}$-haloalkyl-, $C_{1-6}$-alkyl-O— and $C_{1-6}$-haloalkyl-O—;

Another embodiment of the invention is a process for the preparation of compounds of general formula 1, characterized in that the process comprises the preparation of compounds of general formula C4,

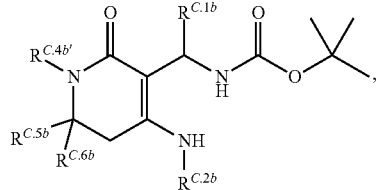

optionally in the form of the tautomers thereof; characterized in that the process comprises the reaction B, wherein B is the reaction of a compound of formula C5 with a compound of formula C6, to form a compound of formula C4,

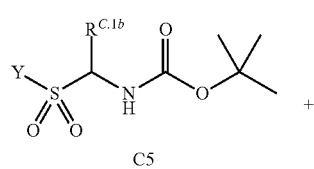

+

-continued

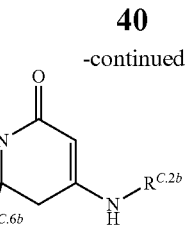

C6

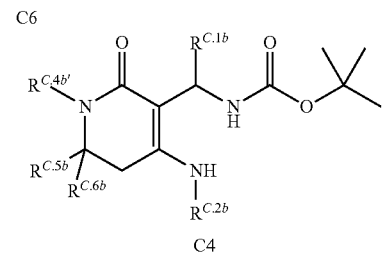

C4 wherein $R^{C.1b}$ is phenyl, optionally substituted with one or two substituents independently selected from the group consisting of Br, NC— and $CF_3$—;

$R^{C.2b}$ is phenyl; optionally substituted with $CF_3$—;

$R^{C.4b'}$ is tert-butyl-O(O)C—;

$R^{C.5b}$ is H;

$R^{C.6b}$ is H; and

Y is phenyl;

A further embodiment of the invention is a process for the preparation of compounds of general formula 1, characterized in that the process comprises the preparation of compounds of general formula C7,

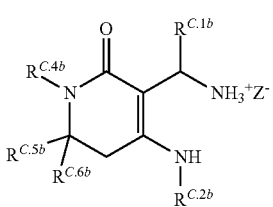

optionally in the form of the tautomers thereof; characterized in that the process comprises the reaction C, wherein C is the reaction of a compound of formula C4, to form a compound of formula C7,

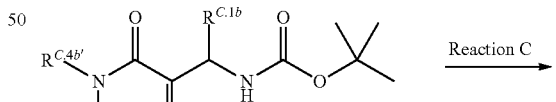

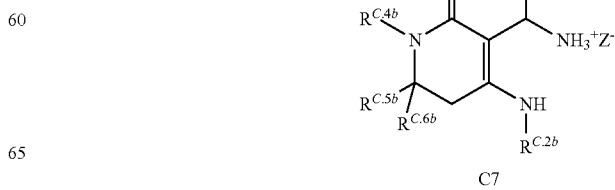

wherein
$R^{C.1b}$ is phenyl; optionally substituted with one or two substituents independently selected from the group consisting of F, Cl, Br, NC—, methyl, ethyl, $CF_2H$—, $CF_3$—, MeO—, EtO—, $CF_3O$—, methyl-(O)S—, ethyl-(O)S—, methyl-$(O)_2S$— and ethyl-$(O)_2S$—;
$R^{C.2b}$ is phenyl; optionally substituted with one or two substituents independently selected from F—, $CF_3$— and $CF_2H$—;
$R^{C.4b'}$ is H, $C_{1-6}$-alkyl- or $C_{1-6}$-alkyl-O(O)C—;
$R^{C.4b}$ is H or $C_{1-6}$-alkyl-;
$R^{C.5b}$ is independently selected from H and $C_{1-6}$-alkyl-;
$R^{C.6b}$ is independently selected from H and $C_{1-6}$-alkyl-; and
Z is halogen;

Another embodiment of the invention is a process for the preparation of compounds of general formula 1, characterized in that the process comprises the preparation of compounds of general formula C7,

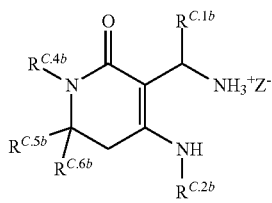

C7 optionally in the form of the tautomers thereof; characterized in that the process comprises the reaction C, wherein C is the reaction of a compound of formula C4, to form a compound of formula C7,

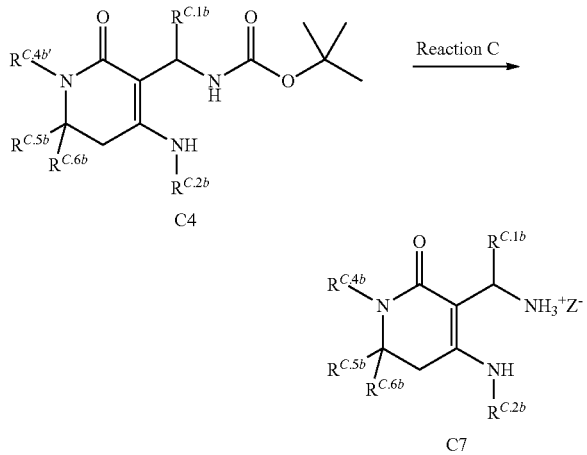

wherein
$R^{C.1b}$ is phenyl, optionally substituted with one or two substituents independently selected from the group consisting of Br, NC— and $CF_3$—;
$R^{C.2b}$ phenyl; optionally substituted with $CF_3$—;
$R^{C.4b'}$ is tert-butyl-O(O)C—;
$R^{C.4b}$ is H;
$R^{C.5b}$ is H;
$R^{C.6b}$ is H; and
Z is Cl;

A further embodiment of the invention is a process for the preparation of compounds of general formula 1, characterized in that the process comprises the preparation of compounds of general formula C1b,

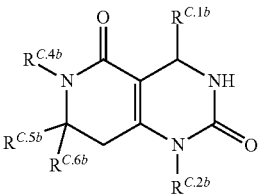

C1b optionally in the form of the tautomers thereof; characterized in that the process comprises the reaction D, wherein D is the reaction of a compound of formula C7, to form a compound of formula C1b,

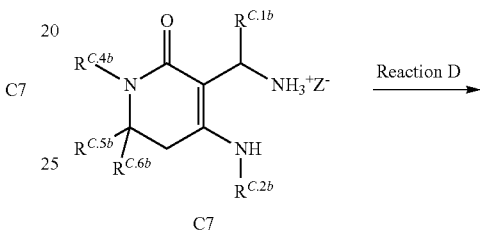

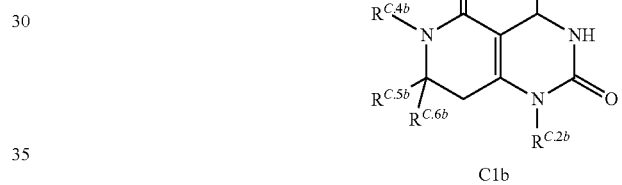

C1b wherein
$R^{C.1b}$ is phenyl; optionally substituted with one or two substituents independently selected from the group consisting of F, Cl, Br, NC—, methyl, ethyl, $CF_2H$—, $CF_3$—, MeO—, EtO—, methyl-(O)S—, ethyl-(O)S—, methyl-$(O)_2S$— and ethyl-$(O)_2S$—;
$R^{C.2b}$ is phenyl; optionally substituted with one or two substituents independently selected from F—, $CF_3$— and $CF_2H$—;
$R^{C.4b}$ is H or $C_{1-6}$-alkyl-;
$R^{C.5b}$ is independently selected from H and $C_{1-6}$-alkyl-;
$R^{C.6b}$ is independently selected from H and $C_{1-6}$-alkyl-; and
Z is halogen;

Another embodiment of the invention is a process for the preparation of compounds of general formula 1, characterized in that the process comprises the preparation of compounds of general formula C1b,

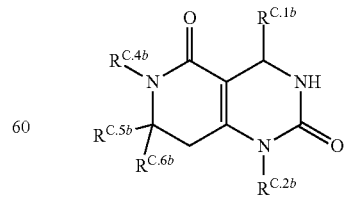

C1b optionally in the form of the tautomers thereof; characterized in that the process comprises the reaction D, wherein D is the reaction of a compound of formula C7, to form a compound of formula C1b,

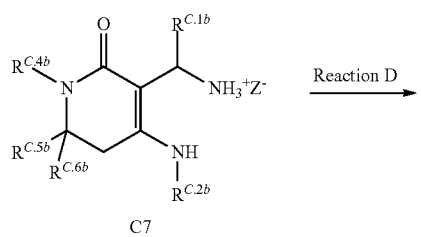

C7

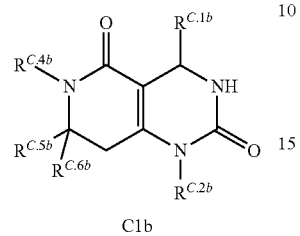

C1b wherein
R$^{C.1b}$ is phenyl, optionally substituted with one or two substituents independently selected from the group consisting of Br, NC— and CF$_3$—;
R$^{C.2b}$ is phenyl; optionally substituted with CF$_3$—;
R$^{C.4b}$ is H,
R$^{C.5b}$ is H,
R$^{C.6b}$ is H; and
Z Cl;

A further embodiment of the invention is a process for the preparation of compounds of general formula 1, characterized in that the process comprises the preparation of compounds of general formula C1b,

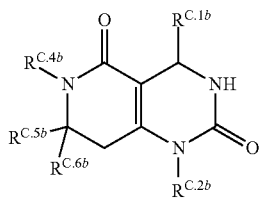

C1b optionally in the form of the tautomers thereof; characterized in that the process comprises the reactions B, C and D, wherein B is the reaction of a compound of formula C5 with a compound of formula C6, to form a compound of formula C4, C is the reaction of a compound of formula C4, to form a compound of formula C7, and D is the reaction of a compound of formula C7, to form a compound of formula C1b,

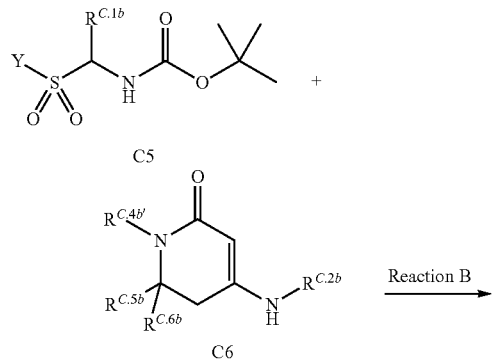

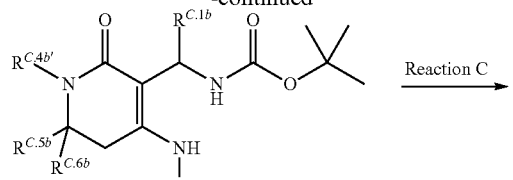

C4

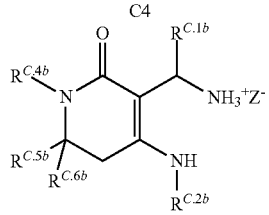

C7

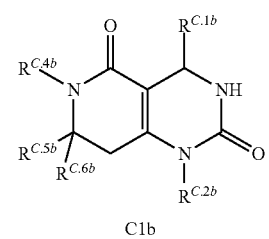

C1b wherein
R$^{C.1b}$ is phenyl; optionally substituted with one or two substituents independently selected from the group consisting of F, Cl, Br, NC—, methyl, ethyl, CF$_2$H—, CF$_3$—, MeO—, EtO—, CF$_3$O—, methyl-(O)S—, ethyl-(O)S—, methyl-(O)$_2$S— and ethyl-(O)$_2$S—;
R$^{C.2b}$ is phenyl; optionally substituted with one or two substituents independently selected from F—, CF$_3$— and CF$_2$H—;
R$^{C.4b'}$ is H, C$_{1-6}$-alkyl- or C$_{1-6}$-alkyl-O(O)C—;
R$^{C.4b}$ is H or C$_{1-6}$-alkyl-;
R$^{C.5b}$ is independently selected from H and C$_{1-6}$-alkyl-;
R$^{C.6b}$ is independently selected from H and C$_{1-6}$-alkyl-;
Y is phenyl, optionally substituted with one or two substituents independently selected from the group consisting of halogen, NC—, O$_2$N—, C$_{1-6}$-alkyl-, C$_{1-6}$-haloalkyl-, C$_{1-6}$-alkyl-O— and C$_{1-6}$-haloalkyl-O—; and
Z is halogen;

Another embodiment of the invention is a process for the preparation of compounds of general formula 1, characterized in that the process comprises the preparation of compounds of general formula C1b,

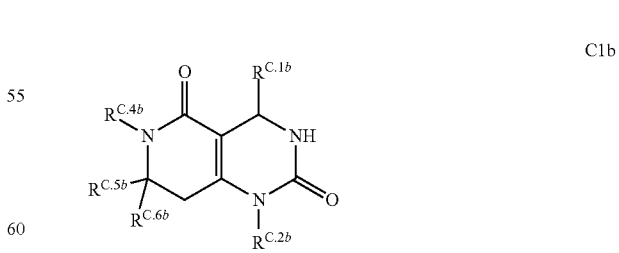

C1b optionally in the form of the tautomers thereof; characterized in that the process comprises the reactions B, C and D, wherein B is the reaction of a compound of formula C5 with a compound of formula C6, to form a compound of formula C4, C is the reaction of a compound of formula C4, to form a compound of formula C7, and D is the reaction of a compound of formula C7, to form a compound of formula C1b,

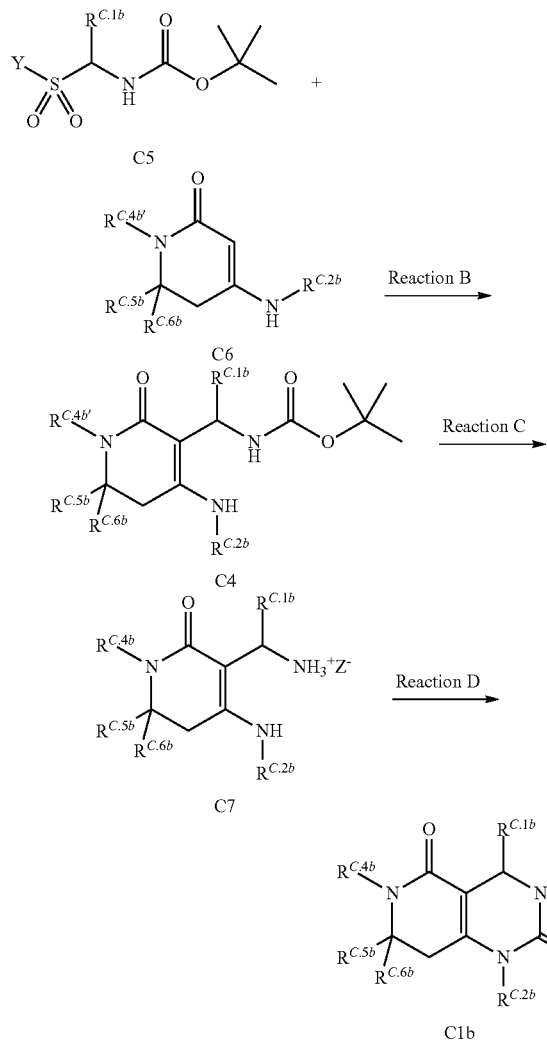

wherein
$R^{C.1b}$ is phenyl, optionally substituted with one or two substituents independently selected from the group consisting of Br, NC— and $CF_3$—;
$R^{C.2b}$ is phenyl; optionally substituted with $CF_3$—;
$R^{C.4b'}$ is tert-butyl-O(O)C—;
$R^{C.4b}$ is H;
$R^{C.5b}$ is H;
$R^{C.6b}$ is H;
Y is phenyl; and
Z Cl;

A further embodiment of the invention are compounds of formula C4,

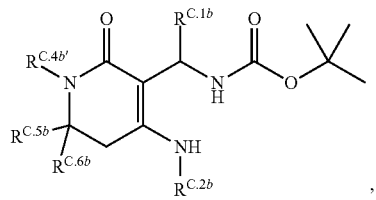

or a pharmaceutically acceptable salt thereof, optionally in the form of the tautomers thereof, useful for the preparation of compounds of general formula C1b,
wherein
$R^{C.1b}$ is phenyl, optionally substituted with one or two substituents independently selected from the group consisting of Br, NC— and $CF_3$—;
$R^{C.2b}$ is phenyl; optionally substituted with $CF_3$—;
$R^{C.4b'}$ is H, $C_{1-6}$-alkyl- or $C_{1-6}$-alkyl-O(O)C—;
$R^{C.5b}$ is independently selected from H and $C_{1-6}$-alkyl-; and
$R^{C.6b}$ is independently selected from H and $C_{1-6}$-alkyl-;

Another embodiment of the invention are compounds of formula C4,

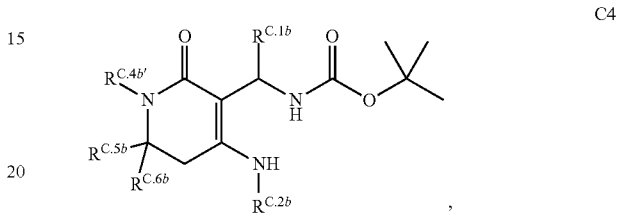

or a pharmaceutically acceptable salt thereof, optionally in the form of the tautomers thereof, useful for the preparation of compounds of general formula C1b,
wherein
$R^{C.1b}$ is

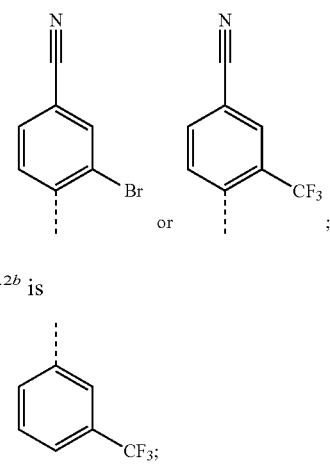

$R^{C.2b}$ is

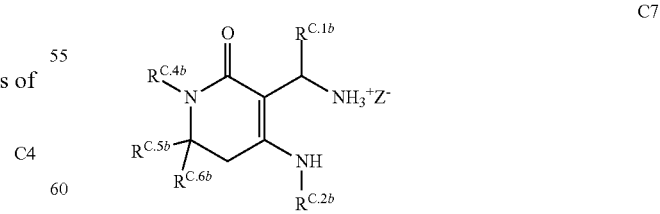

$R^{C.4b'}$ tert-butyl-O(O)C—;
$R^{C.5b}$ is H; and
$R^{C.6b}$ is H;

Another embodiment of the invention are compounds of formula C7,

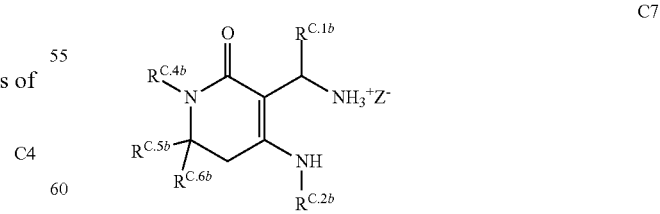

or a pharmaceutically acceptable salt thereof, optionally in the form of the tautomers thereof, useful for the preparation of compounds of general formula C1b, wherein
$R^{C.1b}$ is phenyl, optionally substituted with one or two substituents independently selected from the group consisting of Br, NC— and $CF_3$—;

$R^{C.2b}$ is phenyl; optionally substituted with $CF_3$—;
$R^{C.4b}$ is H or $C_{1-6}$-alkyl-;
$R^{C.5b}$ is independently selected from H and $C_{1-6}$-alkyl-;
$R^{C.6b}$ is independently selected from H and $C_{1-6}$-alkyl-; and
Z is halogen;

Another embodiment of the invention are compounds of formula C7,

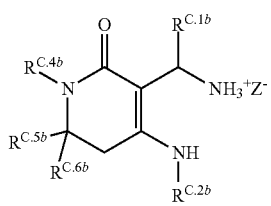

C7 or a pharmaceutically acceptable salt thereof, optionally in the form of the tautomers thereof, useful for the preparation of compounds of general formula C1b,
wherein
$R^{C.1b}$ is

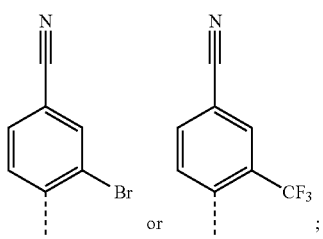

$R^{C.2b}$

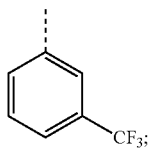

$R^{C.4b}$ is H,
$R^{C.5b}$ is H;
$R^{C.6b}$ is H, and
Z is Cl;

A further embodiment of the invention is are compounds of formula C1b,

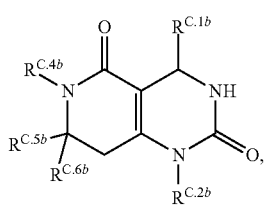

C1b or a pharmaceutically acceptable salt thereof, optionally in the form of the tautomers thereof, wherein
$R^{C.1b}$ is phenyl, optionally substituted with one or two substituents independently selected from the group consisting of Br, NC— and $CF_3$—;
$R^{C.2b}$ is phenyl; optionally substituted with $CF_3$—;
$R^{C.4b}$ is H or $C_{1-6}$-alkyl-;
$R^{C.5b}$ is independently selected from H and $C_{1-6}$-alkyl-; and
$R^{C.6b}$ is independently selected from H and $C_{1-6}$-alkyl-;

Another embodiment of the invention is are compounds of formula C1b,

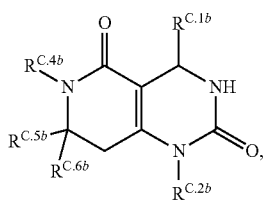

C1b or a pharmaceutically acceptable salt thereof, optionally in the form of the tautomers thereof,
wherein
$R^{C.1b}$ is

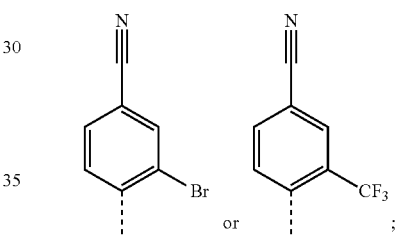

$R^{C.2b}$ is

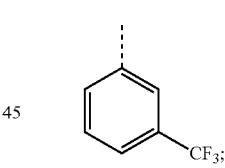

$R^{C.4b}$ is H;
$R^{C.5b}$ is H; and
$R^{C.6b}$ is H.

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes.

Starting materials are commercially available or may be prepared by methods that are described in the literature or herein, or may be prepared in an analogous or similar manner Any functional groups in the starting materials or intermediates may be protected using conventional protecting groups. These protecting groups may be cleaved again at a suitable stage within the reaction sequence using methods familiar to the one skilled in the art.

Compounds of the invention VI are accessible using the synthetic route illustrated in Scheme 1; $R^I$, $R^{E.1}$, $R^{E.2}$ and $R^{E.4}$ have the meanings as defined hereinbefore and hereinafter.

example benzene or toluene. The reaction takes place within 1 to 24 hours. Preferred reaction temperatures are between 50° C. and 150° C.

Alternatively, intermediates III can be prepared as described in Jochims et al. (*Chem. Ber.* 1982, 115, 860-870) by α-halogenation of aliphatic isocyanates, for example benzyl isocyanate, using for example a bromination agent, for example N-bromosuccinimide Isocyanates can be synthesized as described in U.S. Pat. No. 6,207,665 and in Charalambides et al. (*Synth. Commun.* 2007, 37, 1037-1044), by reacting an amine precursor with phosgene.

SCHEME 1

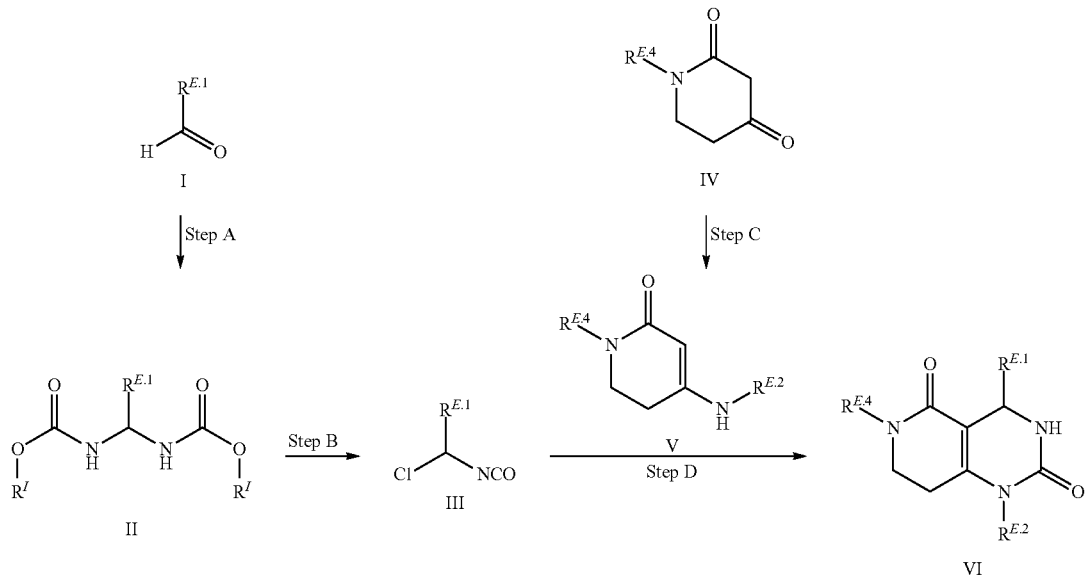

Intermediates II (Step A, intermediate I→intermediate II) can be prepared as described in Vovk et al. (*Synlett* 2006, 3, 375-378) or in PL2004/369318, by heating an aliphatic or aromatic aldehyde I with a carbamate, for example methyl carbamate, ethyl carbamate (urethane) or benzyl carbamate in the presence of a strong Brønsted or a Lewis acid, for example sulfuric acid, hydrogen chloride, p-toluenesulfonic acid, Amberlyst 15, tetrafluoroboric acid, trifluoroacetic acid or boron trifluoride, either without solvent as a melt or in a suitable solvent, such as benzene, toluene, acetonitrile, diethyl ether, chloroform, acetic anhydride or mixtures thereof. The reaction takes place within 1 to 24 hours. Preferred reaction temperatures are between room temperature and 160° C., or the boiling point of the solvent, respectively. Preferably the reaction is done with molten ethyl carbamate as reactant and a catalytic amount of concentrated sulfuric acid at temperatures of 140-160° C. without any additional solvent.

The chlorination (Step B, intermediate II→intermediate III) can be done as described in Vovk et al. (*Synlett* 2006, 3, 375-378) and Sinitsa et al. (*J. Org. Chem. USSR* 1978, 14, 1107) by heating intermediate II together with a chlorinating agent, for example phosphorous pentachloride, phosphoryl chloride or sulfuryl chloride in an organic solvent, for Intermediates V (Step C, intermediate IV→intermediates V) can be prepared as described in Chen et al. (*Synth. Commun.* 2010, 40, 2506-2510) and Tietcheu et al. (*J. Heterocyclic Chem.* 2002, 39, 965-973) by reacting piperidine-2,4-dione (IV, $R^{E.4}$=H) and an aliphatic or aromatic amine in the presence of a catalyst, for example Ytterbium triflate [Yb(OTf)₃] or an acid, for example hydrogen chloride or p-toluenesulfonic acid, optionally in a solvent, for example water, acetic acid, acetonitrile, benzene, toluene. The reaction takes place within 1-24 hours. Preferred reaction temperatures are between room temperature and 120° C., most preferred room temperature.

Alternatively, the piperidine-2,4-dione can be further substituted on nitrogen (intermediate IV, $R^{E.4}$≠H) or can carry a suitable protecting group on nitrogen (intermediate IV, $R^{E.4}$≠H). The protecting group can be for example a carbamate, for example tert-butyl carbamate (Boc) or benzyloxycarbonyl (Cbz), benzyl (Bn) or para-methoxybenzyl (PMB), or any other suitable protecting group known to the one skilled in the art or as described in Kociasky (*Protecting groups*, Thieme, 3rd ed, 2005).

Alternatively, intermediates V can be prepared as described in WO12035078 by direct condensation of the piperidine-2,4-dione with an amine or as described in Scott et al. (*J. Med. Chem.* 1993, 36, 1947-1955) under reflux in a suitable solvent, for example benzene or toluene with azeotropic removal of water.

Compounds according to the present invention (Step D, intermediates III→compounds of the invention VI) can be prepared as described in Vovk et al. (*Synlett* 2006, 3, 375-378), Vovk et al. (*Russ. J. Org. Chem.* 2010, 46, 709-715) and Kushnir et al. (*Russ. J. Org. Chem.* 2011, 47, 1727-1732) by reacting intermediates III with intermediates V in an organic solvent, for example dichloromethane, chloroform, benzene or toluene. The reaction takes place within 1-24 hours. Preferred reaction temperatures are between 0° C. and 100° C.

Compounds according to the present invention VII, VIII, IX, X and XI are accessible via the synthetic routes depicted in Scheme 2; $R^{II}$, $R^{III}$, $R^{IV}$, $R^{V}$, $R^{E.1}$, $R^{E.2}$, $R^{E.3}$, $R^{E.4}$ have the meanings as defined hereinbefore and hereinafter.

Compounds of the invention VII (Step E, compounds of the invention VI→compounds of the invention VII, $R^{E.3}$=alkyl or substituted alkyl) can be prepared as described in WO04024700 by reacting compounds of the invention VI with an alkylating agent, for example a dialkyl sulfate, for example dimethyl sulfate, an alkyl halide, for example methyl iodide or an alkyl sulfonylate, for example benzyl tosylate, in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofuran, N,N-dimethylformamide, acetonitrile, 1,4-dioxane, dichloromethane or toluene. The reaction takes place within 1-72 hours. Preferred reaction temperatures are between 0° C. and 100° C.

SCHEME 2

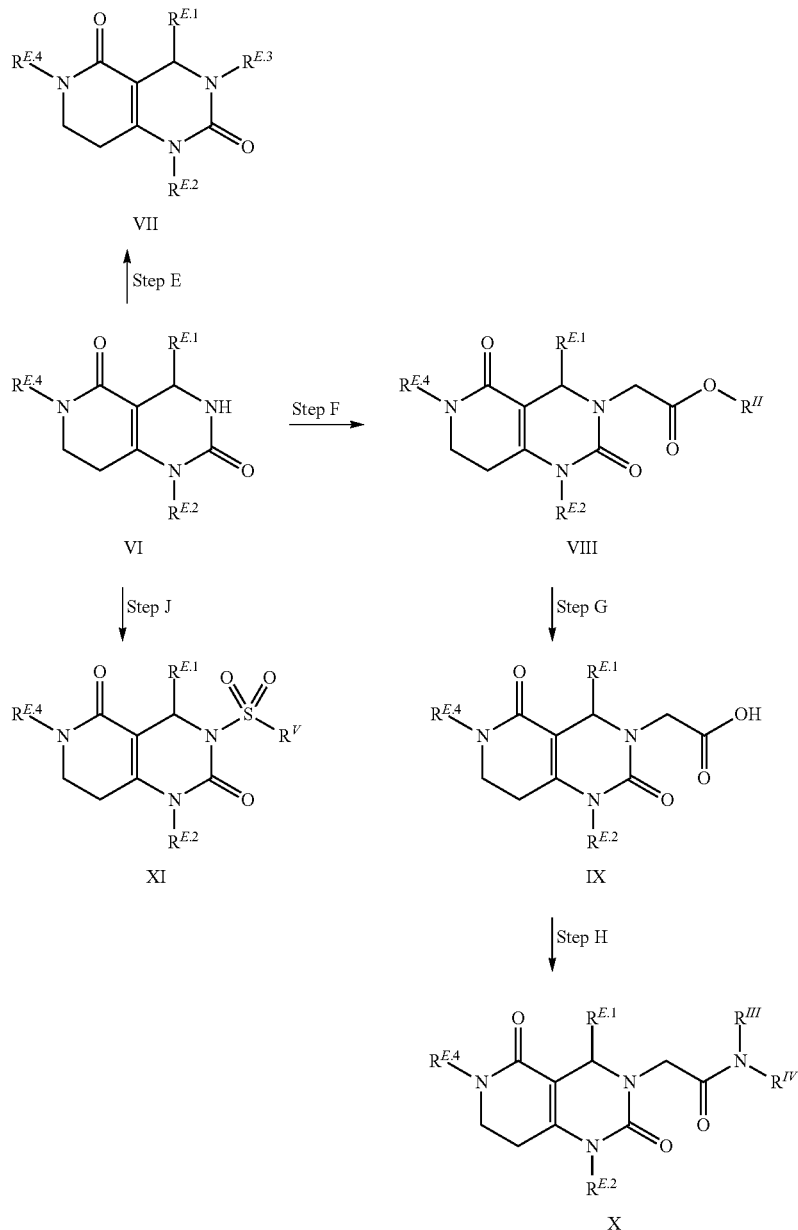

Compounds of the invention VIII (Step F, compounds of the invention VI→compounds of the invention VIII) can be prepared in analogy to compounds of the invention VII (Step E, compounds of the invention VI→compounds of the invention VII), using an appropriate alkyl haloacetate as alkylating agent, for example methyl bromoacetate.

Compounds of the invention IX (Step G, compounds of the invention VIII→compounds of the invention IX) can be prepared as described in WO04024700, by reacting compounds of the invention VIII with water in the presence of a suitable base, for example sodium hydroxide, potassium hydroxide, caesium hydroxide, lithium hydroxide, sodium carbonate, potassium carbonate, sodium methoxide or sodium ethoxide in a suitable solvent, for example water, methanol, ethanol, propanol, N,N-dimethylformamide, tetrahydrofuran, 1,4-dioxane, acetonitrile or mixtures thereof. The reaction takes place within 1-72 hours. Preferred reaction temperatures are between 0° C. and 100° C.

The amide coupling (Step H, compounds of the invention IX→compounds of the invention X) can be achieved by reacting the carboxylic acid intermediate IX with amines $R^{III}NH_2$ or $R^{III}R^{IV}NH$ in the presence of an amide coupling reagent, for example N,N,N',N'-tetramethyl-O-(benzotriazol-1-yl)uronium tetrafluoroborate (TBTU) or N,N,N',N'-tetramethyl-O-(benzotriazol-1-yl)uronium hexafluorophosphate (HBTU), in the presence of a base, for example triethylamine, N,N-diisopropylethylamine or N-methylmorpholine in an organic solvent, for example N-methyl-2-pyrrolidone N,N-dimethylformamide, N,N-dimethylacetamide or mixtures thereof. The reaction takes place within 1-72 hours. Preferred reaction temperatures are between 0° C. and 50° C., most preferred room temperature.

Compounds of the invention XI (Step J, compounds of the invention VI→compounds of the invention XI, $R^V$=alkyl or aryl) can be prepared as described in WO07137874, by reacting compounds of the invention VI with a sulfonylating agent, for example methanesulfonyl chloride or para-toluenesulfonyl chloride in the presence of a base, for example sodium hydride, lithium diisopropylamide, potassium hexamethyldisilazide, lithium hexamethyldisilazide, an organolithium reagent, for example tert-butyllithium or a Grignard reagent, for example iso-propylmagnesiumchloride, in an organic solvent, for example tetrahydrofuran, N,N-dimethylformamide, acetonitrile, 1,4-dioxane or dichloromethane. The reaction takes place within 1-72 hours. Preferred reaction temperatures are between 0° C. and room temperature.

Compounds according to the present invention XIII and XIV are accessible via the synthetic routes depicted in Scheme 3; $R^{III}$, $R^{IV}$, $R^{VI}$, $R^{E.1}$, $R^{E.2}$, $R^{E.4}$ have the meanings as defined hereinbefore and hereinafter.

SCHEME 3

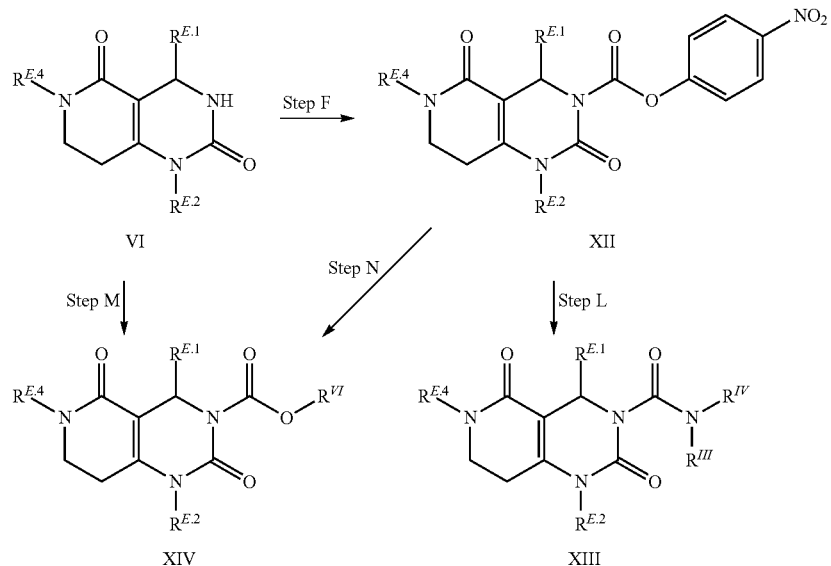

Intermediates XII (Step K, compounds of the invention VI→intermediates XII) can be prepared as described in WO09080199, by reacting compounds of the invention VI with 4-nitrophenyl chloroformate in the presence of a base, for example triethylamine, N,N-diisopropylethylamine or N-methylmorpholine, optionally in the presence of a catalyst, for example 4-dimethylaminopyridine, in an organic solvent, for example dichloromethane, tetrahydrofuran, acetonitrile or N,N-dimethylformamide. The reaction takes place within 1-24 hours. Preferred reaction temperatures are between 0° C. and 50° C., most preferred room temperature.

Compounds of the invention XIII (Step L, intermediates XII→compounds of the invention XIII) can be prepared as described in WO09080199, by reacting intermediates XII with an amine $R^{III}NH_2$ or $R^{III}R^{IV}NH$ in an organic solvent, for example dichloromethane, acetonitrile, tetrahydrofuran, 1,4-dioxane, toluene or N,N-dimethylformamide. The reaction takes place within 1-72 hours. Preferred reaction temperatures are between 0° C. and 50° C., most preferred room temperature.

Compounds of the invention XIV (Step M, compounds of the invention VI→compounds of the invention XIV) can be prepared as described in WO07046513 or JP2000273087, by reacting compounds of the invention VI with a suitable chloroformate $ClCO_2R^{VI}$, for example methyl chloroformate or benzyl chloroformate, in the presence of a suitable base, for example potassium carbonate, sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofuran, N,N-dimethylformamide, acetonitrile, 1,4-dioxane, dichloromethane or toluene. The reaction takes place within 1-72 hours. Preferred reaction temperatures are between 0° C. and 100° C.

Alternatively, compounds of the invention XIV (Step N, intermediates XII→compounds of the invention XIV) can be prepared as described in WO03101917 or WO11085211, by reacting intermediates XII with a suitable alcohol, for example methanol, iso-propanol, 2-methoxyethanol or benzyl alcohol, in the presence of a suitable base, for example potassium carbonate, potassium tert-butoxide or sodium hexamethyldisilazide in an organic solvent, for example tetrahydrofuran, N,N-dimethylformamide, acetonitrile, dichloromethane or dimethylsulfoxide. The reaction takes place within 1-72 hours. Preferred reaction temperatures are between 0° C. and 100° C., most preferred room temperature.

Additionally to the synthetic route depicted in Scheme 1, compounds of the invention VI are also accessible using the synthetic route depicted in Scheme 4, $R^{E.1}$, $R^{E.2}$, $R^{E.4}$ have the meanings as defined hereinbefore and hereinafter.

SCHEME 4

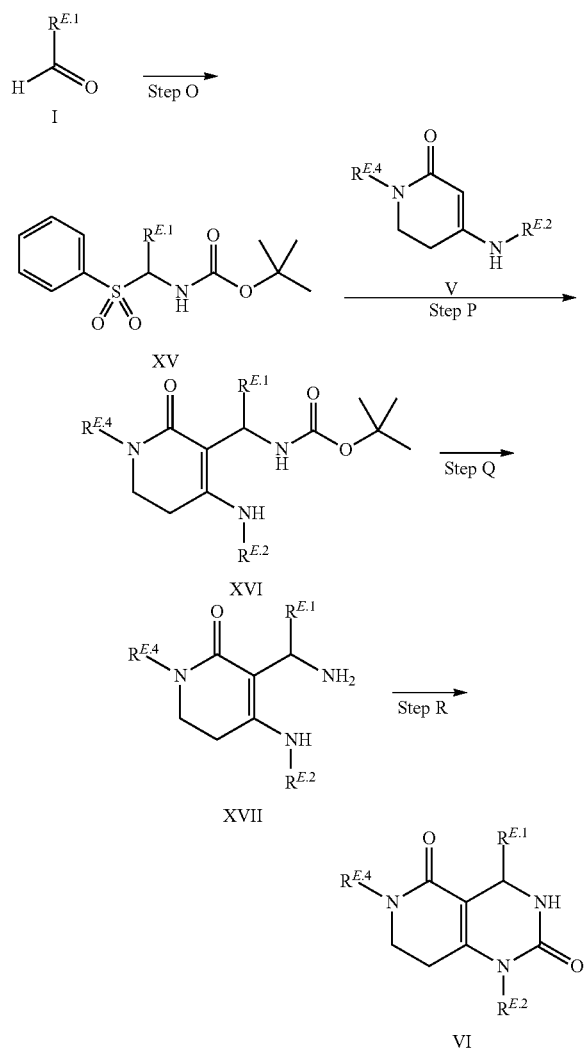

Intermediates XV (Step O, intermediate I→intermediate XV) can be prepared as described in Best et al. (*J. Am. Chem. Soc.* 2012, 134, 18193-18196) or in Yang et al. (*Org. Synth.* 2009, 86, 11-17), by reacting an aromatic aldehyde I with a suitable sulfinate, for example sodium benzenesulfinic acid, and a suitable carbamate, for example methyl carbamate or tert-butyl carbamate, in the presence of a suitable acid, for example formic acid, in a suitable solvent, for example tetrahydrofuran, ethanol, methanol or a mixture of solvents, for example tetrahydrofuran and water. Alternatively, as described in Reingruber et al. (*Adv. Synth. Catal.* 2009, 351, 1019-1024) or in WO06136305, a suitable lewis acid, for example trimethylsilyl chloride, can be used as acid and acetonitrile or toluene can be used as solvent. The reaction takes place within 1-6 days. Preferred reaction temperatures are between 0° C. and 50° C., most preferred room temperature.

Intermediates XVI (Step P, intermediate XV→intermediate XVI) can be prepared in analogy to the method described for the preparation of compounds of the invention VI (Scheme 1, Step D, intermediate III→compound of the invention VI), by reacting intermediates XV with intermediates V in the presence of a suitable base, for example sodium hydride or sodium tert-butoxide, in a suitable organic solvent, for example tetrahydrofuran or 2-methyltetrahydrofuran. The reaction takes place within 1-24 h. Preferred reaction temperatures are between 0° C. and 50° C., most preferred room temperature.

Intermediates XVII (Step Q, intermediate XVI→intermediate XVII) can be prepared by reacting intermediates XVI with a suitable acid or lewis acid, for example hydrogen chloride or trimethylsilyl iodide, in a suitable solvent, for example 1,4-dioxane. The reaction takes place between 1-72 hours. Preferred reaction temperatures are between 0° C. and room temperature, most preferred room temperature.

Compounds of the invention VI (Step R, intermediate XVII→compound of the invention VI) can be prepared as described in Csütörtöki et al. (*Tetrahedron Lett.* 2011, 67, 8564-8571) or in WO11042145, by reacting intermediates XVII with a suitable reagent, for example phosgene, triphosgene or carbonyl diimidazole, in the presence of a suitable base, for example triethylamine, N,N-diisopropylethylamine, pyridine or sodium carbonate, in a suitable solvent, for example acetonitrile, dichloromethane or toluene. The reaction takes place between 1-72 hours. Preferred reaction temperatures are between 0° C. and 50° C., most preferred room temperature.

Preliminary Remarks

The term room temperature denotes a temperature of about 20° C., e.g. 15-25° C., preferably 18-22° C. As a rule, $^1$H NMR spectra and/or mass spectra have been obtained of the compounds prepared. Compounds given with a specific configuration at a stereocenter are isolated as pure isomers.

The retention times given are measured under the following conditions (TFA: trifluoroacetic acid, DEA: diethylamine, scCO$_2$: supercritical carbon dioxide):

| Method Name: | V001_006 |
| Column: | XBridge C18, 4.6 × 30 mm, 3.5 μm |
| Column Supplier: | Waters |

| Gradient/ Solvent Time [min] | % Solvent [H$_2$O, 0.1% TFA] | % Solvent [methanol] | Flow [ml/min] | Temp [° C.] |
| --- | --- | --- | --- | --- |
| 0.0 | 95 | 5 | 4.8 | 60 |
| 1.6 | 0 | 100 | 4.8 | 60 |
| 1.85 | 0 | 100 | 4.8 | 60 |
| 1.9 | 95 | 5 | 4.8 | 60 |

Method Name: V011_S01  
Column: XBridge C18, 4.6 × 30 mm, 3.5 μm  
Column Supplier: Waters

| Gradient/ Solvent Time [min] | % Solvent [H$_2$O, 0.1% NH$_3$] | % Solvent [acetonitrile] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method Name: V012_S01  
Column: XBridge C18, 4.6 × 30 mm, 3.5 μm  
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method Name: W018_S01  
Column: Sunfire C18, 4.6 × 30 mm, 2.5 μm  
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 97 | 3 | 4 | 60 |
| 0.15 | 97 | 3 | 3 | 60 |
| 2.15 | 0 | 100 | 3 | 60 |
| 2.20 | 0 | 100 | 4,5 | 60 |
| 2.40 | 0 | 100 | 4,5 | 60 |

Method Name: X011_S03  
Column: Xbridge BEH C18, 2.1 × 30 mm, 1.7 μm  
Column Supplier: Waters

| Gradient/ Solvent Time [min] | % Solvent [H$_2$O, 0.1% NH$_3$] | % Solvent [acetonitrile] | Flow [ml/min] | Temperature [° C.] |
|---|---|---|---|---|
| 0.0 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: X012_S01  
Column: Xbridge BEH C18, 2.1 × 30 mm, 1.7 μm  
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method Name: X018_S01  
Column: Sunfire C18, 2.1 × 30 mm, 2.5 μm  
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method Name: Z001_005  
Column: XBridge C18, 3 × 30 mm, 2.5 μm  
Column Supplier: Waters

| Gradient/ Solvent Time [min] | % Solvent [H$_2$O, 0.1% TFA] | % Solvent [methanol] | Flow [ml/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |
| 0.0 | 95 | 5 | 1.9 | 60 |

Method Name: Z003_004  
Column: XBridge C18, 3 × 30 mm, 2.5 μm  
Column Supplier: Waters

| Gradient/ Solvent Time [min] | % Solvent [H$_2$O, 0.1% NH$_3$] | % Solvent [methanol] | Flow [ml/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method Name: Z006_U01  
Column: XBridge Phenyl, 3 × 30 mm, 2.5 μm  
Column Supplier: Waters

| Gradient/ Solvent Time [min] | % Solvent [H$_2$O, 0.1% TFA] | % Solvent [methanol] | Flow [ml/min] | Temperature [° C.] |
|---|---|---|---|---|
| 0.0 | 50 | 50 | 1.9 | 60 |
| 0.20 | 50 | 50 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method Name: Z011_S03  
Column: XBridge C18, 3 × 30 mm, 2.5 μm  
Column Supplier: Waters

| Gradient/ Solvent Time [min] | % Solvent [H$_2$O, 0.1% NH$_3$] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z017_S04 |
|---|---|
| Column: | ZORBAX™ SB-C$_{18}$, 3 × 30 mm, 1.8 µm |
| Column Supplier: | Agilent |

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z018_S04 |
|---|---|
| Column: | Sunfire, 3 × 30 mm, 2.5 µm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | 001_CA03 |
|---|---|
| Column: | SunFire C18, 4.6 × 30 mm, 3.5 µm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 98 | 2 | 2.5 | 60.0 |
| 1.5 | 0 | 100 | 2.5 | 60.0 |
| 1.8 | 0 | 100 | 2.5 | 60.0 |

| Method Name: | 001_CA07 |
|---|---|
| Column: | SunFire C18, 2.1 × 50 mm, 2.5 µm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 95 | 5 | 1.5 | 60.0 |
| 0.75 | 0 | 100 | 1.5 | 60.0 |
| 0.85 | 0 | 100 | 1.5 | 60.0 |

| Method Name: | 002_CA03 |
|---|---|
| Column: | SunFire C18, 3.0 × 30 mm, 2.5 µm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 2.0 | 60.0 |
| 0.90 | 0 | 100 | 2.0 | 60.0 |
| 1.1 | 0 | 100 | 2.0 | 60.0 |

| Method Name: | 002_CA07 |
|---|---|
| Column: | XBridge BEH C18, 3 × 30 mm, 1.7 µm |
| Column Supplier: | Waters |

| Gradient/ Solvent Time [min] | % Solvent [H$_2$O, 0.1% NH$_3$] | % Solvent [acetonitrile] | Flow [ml/min] | Temperature [° C.] |
|---|---|---|---|---|
| 0.0 | 95 | 5.0 | 1.5 | 60.0 |
| 0.7 | 0.1 | 99.9 | 1.5 | 60.0 |
| 0.8 | 0.1 | 99.9 | 1.5 | 60.0 |
| 0.81 | 95 | 5 | 1.5 | |
| 1.1 | 95 | 5 | 1.5 | |

| Method Name: | 003_CA04 |
|---|---|
| Column: | XBridge C18, 3 × 30 mm, 2.5 µm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 98 | 2 | 2.0 | 60.0 |
| 1.2 | 0 | 100 | 2.0 | 60.0 |
| 1.4 | 0 | 100 | 2.0 | 60.0 |

| Method Name: | 005_CA01 |
|---|---|
| Column: | SunFire C18, 3.0 × 30 mm, 2.5 µm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 98 | 2 | 2.0 | 60.0 |
| 1.2 | 0 | 100 | 2.0 | 60.0 |
| 1.4 | 0 | 100 | 2.0 | 60.0 |

| Method Name: | 005_CA07 |
|---|---|
| Column: | SunFire C18, 3.0 × 30 mm, 2.5 µm |
| Column Supplier: | Waters |

| Gradient/ Solvent Time [min] | % Solvent [H$_2$O, 0.1% TFA] | % Solvent [acetonitrile, 0.08% TFA] | Flow [ml/min] | Temperature [° C.] |
|---|---|---|---|---|
| 0.0 | 95 | 5 | 1.5 | 60.0 |
| 1.3 | 0 | 100 | 1.5 | 60.0 |
| 1.5 | 0 | 100 | 1.5 | 60.0 |
| 1.6 | 95 | 5 | 1.5 | 60.0 |

| Method Name: | I_IA_15_MeOH_DEA |
|---|---|
| Column: | Chiralpak IA 4.6 × 250 mm, 5 µm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 15 | 85 | 4 | 40 | 150 |

| Method Name: | I_IA_20_MeOH_DEA |
| Column: | Chiralpak IA 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

| Method Name: | I_IA_20_MeOH_NH3 |
| Column: | Chiralpak IA 4.6 × 250 mm, 5 μm |
| Column Supplier: | Daicel |

| Gradient/Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

| Method Name: | I_IA_30_MeOH_NH3 |
| Column: | Chiralpak IA 4.6 × 250 mm, 5 μm |
| Column Supplier: | Daicel |

| Gradient/Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 30 | 70 | 4 | 40 | 150 |

| Method Name: | I_IB_15_MeOH_DEA |
| Column: | Chiralpak IB 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 15 | 85 | 4 | 40 | 150 |

| Method Name: | I_IB_20_MeOH_DEA |
| Column: | Chiralpak IB 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

| Method Name: | I_IB_25_MeOH_DEA |
| Column: | Chiralpak IB 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 25 | 75 | 4 | 40 | 150 |

| Method Name: | I_IB_25_MeOH_NH3 |
| Column: | Chiralpak IB 4.6 × 250 mm, 5 μm |
| Column Supplier: | Daicel |

| Gradient/Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 25 | 75 | 4 | 40 | 150 |

| Method Name: | I_IB_30_MeOH_DEA |
| Column: | Chiralpak IB 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 30 | 70 | 4 | 40 | 150 |

| Method Name: | I_IB_40_MeOH_DEA |
| Column: | Chiralpak IB 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 40 | 60 | 4 | 40 | 150 |

| Method Name: | I_IC_30_MeOH_DEA |
| Column: | Chiralpak IC 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 30 | 70 | 4 | 40 | 150 |

| Method Name: | I_IC_40_MeOH_DEA |
| Column: | Chiralpak IC 4.6 × 250 mm, 5 μm |
| Column Supplier: | Daicel |

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 40 | 60 | 4 | 40 | 150 |

| Method Name: | Z001_002 |
| Column: | XBridge C18, 3 × 30 mm, 2.5 μm |
| Column Supplier: | Waters |

| Gradient/ Solvent Time [min] | % Solvent [H₂O, 0.1% TFA] | % Solvent [methanol] | Flow [ml/min] | Temperature [° C.] |
| --- | --- | --- | --- | --- |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method Name: | I_IA_20_IPA_NH3 |
| Column: | Chiralpak IA 4.6 × 250 mm, 5 μm |
| Column Supplier: | Daicel |

| Gradient/ Solvent Time [min] | % Solvent [i-PrOH, 0.2% NH₃] | % Solvent [scCO₂] | Flow [ml/min] | Temperature [° C.] | Back Pressure [bar] |
| --- | --- | --- | --- | --- | --- |
| 10 min | 20 | 80 | 4 | 40 | 150 |

| Method Name: | I_IC_30_ETOH_NH3 |
| Column: | Chiralpak IC 4.6 × 250 mm, 5 μm |
| Column Supplier: | Daicel |

| Gradient/ Solvent Time [min] | % Solvent [EtOH, 0.2% NH₃] | % Solvent [scCO₂] | Flow [ml/min] | Temperature [° C.] | Back Pressure [bar] |
| --- | --- | --- | --- | --- | --- |
| 10 min | 30 | 70 | 4 | 40 | 150 |

Assignment of Absolute Configurations

The absolute configuration of example 1A has been assigned unambiguously by X-ray structure analysis to be (R). This (R)-enantiomer (example 1A) is significantly more potent with respect to the inhibition of neutrophil elastase than the (S)-enantiomer (example 1B), as can be seen from the measured IC$_{50}$ values of 3.1 nM (example 1A) and 940 nM (example 1B), respectively. The absolute configuration of all other pure enantiomers described has been assigned in analogy to example 1A, that is, the more potent enantiomer (the eutomer) with respect to the inhibition of neutrophil elastase, that is the enantiomer with the lower IC$_{50}$ value has been assigned to have the same absolute configuration as example 1A.

Syntheses of Starting Materials

1-Bromo-4-(chloro(isocyanato)methyl)benzene was prepared as described in Vovk et al. (*Synlett* 2006, 3, 375-378).
tert-Butyl 2,4-dioxopiperidine-1-carboxylate is commercially available or can be prepared as described in WO12035078.
1-Methylpiperidine-2,4-dione can be prepared as described in WO10057121 or following the procedure described below.
5-(Tetramethyl-1,3,2-dioxaborolan-2-yl)-2-[tris(propan-2-yl)silyl]-1,3-oxazole is commercially available or can be prepared as described in Primas et al. (*Tetrahedron* 2009, 65, 6348-6353).
4-Formyl-3-(trifluoromethyl)benzonitrile can be prepared as described in WO13149997 or WO07140934.
4-Formyl-3-methanesulfonylbenzonitrile can be prepared as described in WO10078953.

Syntheses of Intermediates

Intermediate 1

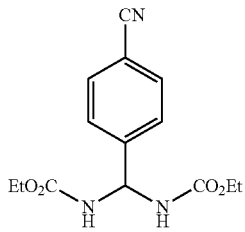 [SMILES: CCOC(=O)NC(NC(=O)OCC)c1ccc(C#N)cc1]

Diethyl (4-Cyanophenyl)methylenedicarbamate

In a three-necked round bottom flask equipped with a drying tube filled with calcium chloride and an inlet for nitrogen, 4-formylbenzonitrile (25.0 g, 191 mmol) and ethyl carbamate (37.4 g, 419 mmol) are heated at 145° C. The flask is being purged with a flow of nitrogen, and concentrated sulfuric acid (ca. 200 μL, ca. 3 mmol) is added slowly drop by drop. After 7 h the solidified reaction mixture is cooled to room temperature, crushed, mixed thoroughly with water and dried. Yield: 53.0 g; ESI mass spectrum: [M+H]$^+$=314; Retention time HPLC: 0.88 min (V011_S01).

Intermediate 2

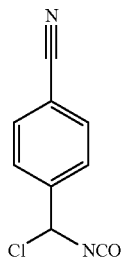

4-(Chloro(isocyanato)methyl)benzonitrile

Phosphorous pentachloride (83.3 g, 400 mmol) is added to a suspension of diethyl (4-cyanophenyl)methylenedicarbamate (intermediate 1, 53.0 g, 182 mmol) in benzene (200 mL) and the mixture is heated at reflux for 2 h. The benzene is evaporated and the mixture is then purified by distillation under reduced pressure. The first fraction (ca. 40° C., ca. 0.01 mbar) is discarded. The second fraction (ca. 110° C., ca. 0.6 mbar) is collected.

Yield: 28.4 g; ESI mass spectrum: [M+MeOH—HCl+H]$^+$=189; Retention time HPLC: 0.65 min (Z003_004).

Intermediate 3

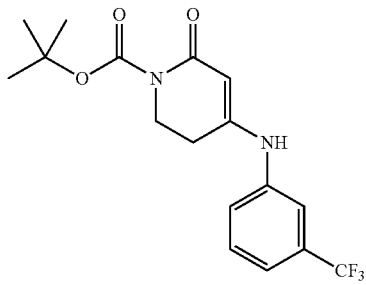 [SMILES: CC(C)(C)OC(=O)N1CCC(Nc2cccc(C(F)(F)F)c2)=CC1=O]

tert-Butyl 2-Oxo-4-(3-(trifluoromethyl)phenylamino)-5,6-dihydropyridine-1(2H)-carboxylate A mixture of tert-butyl 2,4-dioxopiperidine-1-carboxylate (8.00 g, 37.6 mmol), 3-(trifluoromethyl)aniline (4.67 mL, 37.6 mmol), Ytterbium(III) trifluormethanesulfonate (116 mg, 188 μmol) and toluene (6 mL) is stirred at room temperature for 2 h. All volatiles are evaporated and the residue is recrystallized from hot MeOH/water and dried. Yield: 11.8 g; ESI mass spectrum: [M+H]$^+$=357; Retention time HPLC: 1.11 min (V011_S01).

Intermediate 4

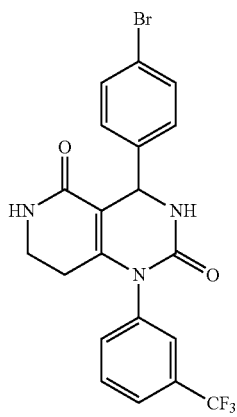 [SMILES: O=C1NCCC2=C1C(c1ccc(Br)cc1)NC(=O)N2c1cccc(C(F)(F)F)c1]

4-(4-Bromophenyl)-1-(3-(trifluoromethyl)phenyl)-3,4,7,8-tetrahydropyrido[4,3-d]-pyrimidine-2,5(1H,6H)-dione A solution of 1-bromo-4-(chloro(isocyanato)methyl)benzene (1.31 g, 5.33 mmol) in dichloromethane (15 mL) is added to a suspension of tert-butyl 2-oxo-4-(3-(trifluoromethyl)-phenylamino)-5,6-dihydropyridine-1(2H)-carboxylate (intermediate 3, 1.90 g, 5.33 mmol) in dichloromethane (50 mL). The mixture is heated at reflux for 30 min, cooled to room temperature and stirred at this temperature over night. Methanol is added and the mixture is filtered. The filtrate is concentrated and the residue is purified by flash chromatography on silica (gradient dichloromethane to dichloromethane/methanol 96:4). Yield: 200 mg; ESI mass spectrum: [($^{79}$Br)-M+H]$^+$=466, [($^{81}$Br)-M+H]$^+$=468; Retention time HPLC: 1.04 min (V011_S01).

Intermediate 5

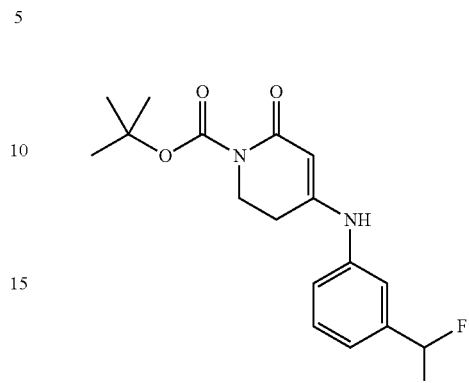

tert-Butyl 4-(3-(Difluoromethyl)phenylamino)-2-oxo-5,6-dihydropyridine-1(2H)-carboxylate A mixture of tert-butyl 2,4-dioxopiperidine-1-carboxylate (2.00 g, 9.38 mmol), 3-(difluoromethyl)aniline (1.34 g, 9.38 mmol) and Ytterbium(III) trifluormethanesulfonate (29 mg, 47 μmol) is stirred at room temperature for 2 h. The solidified reaction mixture is recrystallized from hot MeOH/water. Yield: 2.70 g; ESI mass spectrum: [M+H]$^+$=339; Retention time HPLC: 1.06 min (V012_S01).

Intermediate 6

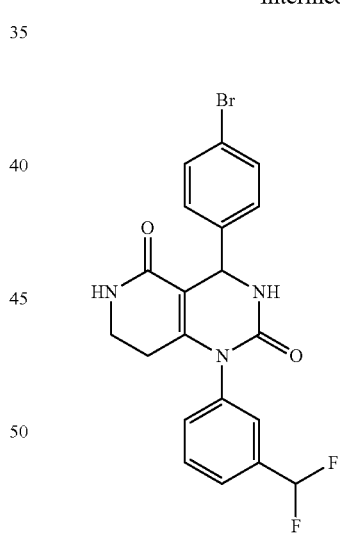

4-(4-Bromophenyl)-1-(3-(difluoromethyl)phenyl)-3,4,7,8-tetrahydropyrido[4,3-d]-pyrimidine-2,5(1H,6H)-dione A solution of 1-bromo-4-(chloro(isocyanato)methyl)benzene (500 mg, 1.62 mmol) in dichloromethane (2.5 mL) is added to a suspension of tert-butyl 4-(3-(difluoromethyl)phenylamino)-2-oxo-5,6-dihydropyridine-1(2H)-carboxylate (intermediate 5, 549 mg, 1.62 mmol) in dichloromethane (2.5 mL). The mixture is heated at reflux for 2 h and cooled to room temperature. Water is added and the mixture is extracted twice with dichloromethane. The combined organic layers are concentrated and the residue is purified by flash chromatography on silica (gradient cyclohexane/ethyl acetate 4:1 to ethyl acetate). Yield: 383 mg; ESI mass spectrum: [($^{79}$Br)-M+H]$^+$=448, [($^{81}$Br)-M+H]$^+$=450; Retention time HPLC: 0.52 min (X012_S01).

Intermediate 7

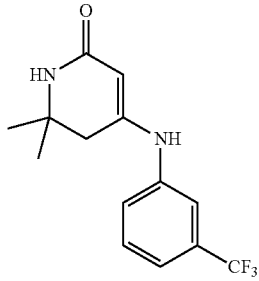 [SMILES: CC1(C)CC(Nc2cccc(C(F)(F)F)c2)=CC(=O)N1]

6,6-Dimethyl-4-(3-(trifluoromethyl)phenylamino)-5,6-dihydropyridin-2(1H)-one

A mixture of 6,6-dimethylpiperidine-2,4-dione (1.00 g, 7.08 mmol), 3-(trifluoromethyl)-aniline (880 µL, 7.08 mmol), Ytterbium(III) trifluormethanesulfonate (22 mg, 35 µmol) and toluene (2 mL) is stirred at room temperature for 5 h. All volatiles are evaporated and the residue is recrystallized from hot MeOH/water. Yield: 950 mg; ESI mass spectrum: [M+H]$^+$=285; Retention time HPLC: 1.11 min (Z001_005).

Intermediate 8

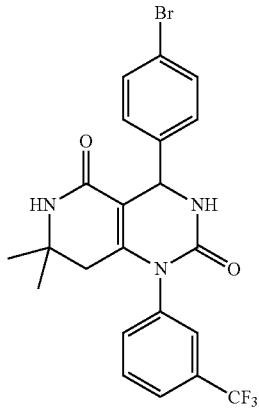 [SMILES: CC1(C)CC2=C(C(=O)N1)C(c1ccc(Br)cc1)NC(=O)N2c1cccc(C(F)(F)F)c1]

4-(4-Bromophenyl)-7,7-dimethyl-1-(3-(trifluoromethyl)phenyl)-3,4,7,8-tetrahydropyrido[4,3-d]pyrimidine-2,5(1H,6H)-dione 1-Bromo-4-(chloro(isocyanato)methyl)benzene (433 mg, 1.76 mmol) is added to a suspension of 6,6-dimethyl-4-(3-(trifluoromethyl)phenylamino)-5,6-dihydropyridin-2(1H)-one (intermediate 7, 500 mg, 1.76 mmol) in dichloromethane (45 mL). The mixture is heated at reflux for 2 h and cooled to room temperature. All volatiles are removed and the residue is crystallized from hot methanol/water. Yield: 184 mg; ESI mass spectrum: [($^{79}$Br)-M+H]$^+$=494, [($^{81}$Br)-M+H]$^+$=496; Retention time HPLC: 1.30 min (Z003_004).

Intermediate 9

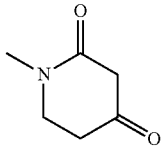

1-Methylpiperidine-2,4-dione

Step 1

Ethyl 3-(Methylamino)propanoate

Methylamine (33% in ethanol, 100 ml, 805 mmol) is cooled in an ice bath at 0° C. Ethyl acrylate (11.0 mL, 10.1 g, 101 mmol) is added, and the mixture is stirred at this temperature for 2 h. The mixture is warmed to room temperature and stirred for 15 min. All volatiles are removed under reduced pressure and the residue is directly used in the next step without further purification. Yield: 11.2 g.

Step 2

Ethyl 3-((3-Ethoxy-3-oxopropyl)(methyl)amino)-3-oxopropanoate

N,N-diisopropylethylamine (16.4 mL, 94.4 mmol) and 4-dimethylaminopyridine (1.05 g, 8.58 mmol) are added at 0° C. to a solution of ethyl 3-(methylamino)propanoate (Step 1, 11.2 g, 85.8 mmol) in dichloromethane (100 mL). Ethyl malonyl chloride (12.0 mL, 94.4 mmoL) is added slowly so that the temperature is kept below 15° C. The mixture is stirred for 30 min and then warmed to room temperature over night. The mixture is poured into aqueous hydrogen chloride solution (2 M, 90 mL) and the phases were separated. The aqueous phase was extracted with dichloromethane, and the combined organic layers were washed with brine, dried over Na$_2$SO$_4$ and concentrated under reduced pressure. The product was purified by flash chromatography on silica (gradient cyclohexane/ethyl acetate 9:1 to 3:7). Yield: 7.2 g; ESI mass spectrum: [M+H]$^+$=246; Retention time HPLC: 0.78 min (Z017_504).

Step 3

1-Methylpiperidine-2,4-dione

Sodium ethylate (21% in ethanol, 12 mL, 32 mmol) is cooled in an ice bath. A solution of ethyl 3-((3-ethoxy-3-oxopropyl)(methyl)amino)-3-oxopropanoate (Step 2, 7.2 g, 29.3 mmol) in ethanol (42 mL) is added slowly so that the temperature is kept below 5° C. The mixture is warmed at room temperature and stirred over night. Tert-butyl methyl ether (15 mL) is added, and the precipitate is filtered and washed with a 1:1 mixture of tert-butyl methyl ether and ethanol (15 mL). The mother liquor is concentrated under reduced pressure, and the residue is dissolved in ethanol (7 mL). tert-Butyl methyl ether (20 mL) is added in portions, and the precipitate is filtered and washed with a 3:1 mixture of tert-butyl methyl ether and ethanol (12 mL). The combined solids are treated with aqueous hydrogen chloride solution (2 M, 55 mL) and dichloromethane (55 mL), and the mixture is stirred for 15 min. The phases are separated and the aqueous layer is extracted with dichloromethane. The combined organic layers are washed with brine, dried over Na$_2$SO$_4$ and concentrated. The residue is dissolved in acetonitrile (75 mL) and water (0.8 mL), and the mixture is heated at reflux for 1 h. All volatiles are removed under reduced pressure. Yield: 3.26 g; ESI mass spectrum: [M+ H]⁺=127; Retention time HPLC: 0.19 min (Z017_504).

Intermediate 10

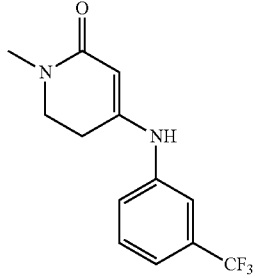 [SMILES: CN1CCC(Nc2cccc(C(F)(F)F)c2)=CC1=O]

1-Methyl-4-(3-(trifluoromethyl)phenylamino)-5,6-dihydropyridin-2(1H)-one

A mixture of 1-methylpiperidine-2,4-dione (intermediate 9, 3.26 g, 25.6 mmol), 3-(trifluoromethyl)aniline (3.19 mL, 25.6 mmol), Ytterbium(III) trifluormethanesulfonate (80 mg, 128 µmol) and toluene (7 mL) is stirred at room temperature for 3 d. The mixture is diluted with methanol and purified by preparative reversed-phase HPLC (Waters Xbridge™-C₁₈, gradient of acetonitrile in water, 0.1% NH₃). Yield: 5.23 g; ESI mass spectrum: [M+H]⁺=271; Retention time HPLC: 0.75 min (Z011_S03).

Intermediate 11

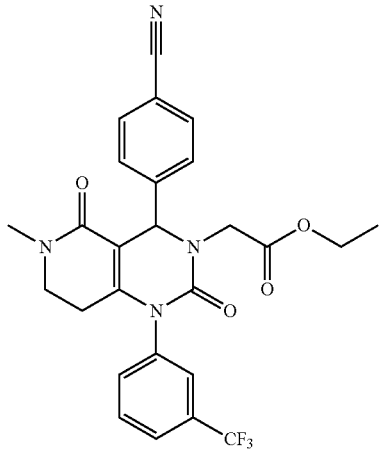 [SMILES: CCOC(=O)CN1C(=O)N(c2cccc(C(F)(F)F)c2)C2=C(C(=O)N(C)CC2)C1c1ccc(C#N)cc1]

Ethyl 2-(4-(4-Cyanophenyl)-6-methyl-2,5-dioxo-1-(3-(trifluoromethyl)phenyl)-1,2,5,6,7,8-hexahydropyrido[4,3-d]pyrimidin-3(4H)-yl)acetate Potassium carbonate (315 mg, 2.28 mmol) and ethyl bromoacetate (200 µL, 0.18 mmol) are added to a solution of 4-(6-methyl-2,5-dioxo-1-(3-(trifluoromethyl)phenyl)-1,2,3,4,5,6,7,8-octahydropyrido[4,3-d]pyrimidin-4-yl)benzonitrile (example 4, 486 mg, 1.14 mmol) in N,N-dimethylformamide (10 mL) and the mixture is stirred at room temperature over night. Water and a few drops of acetonitrile are added, and the mixture is stirred for 4 h. The precipitate is filtered, dissolved in N,N-dimethylformamide and purified by preparative reversed-phase HPLC (Waters SunFire™-C₁₈, gradient of acetonitrile in water, 0.1% TFA). Yield: 365 mg; ESI mass spectrum [M+H]⁺=513; Retention time HPLC: 0.92 min (Z018_S04).

Intermediate 12

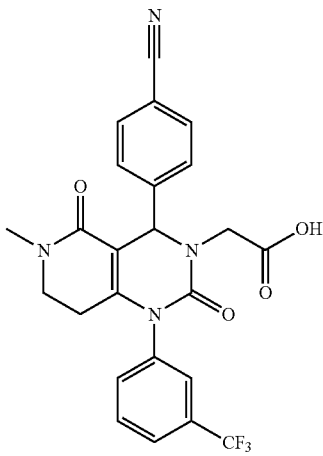 [SMILES: CN1CCC2=C(C1=O)C(c1ccc(C#N)cc1)N(CC(=O)O)C(=O)N2c1cccc(C(F)(F)F)c1]

2-(4-(4-Cyanophenyl)-6-methyl-2,5-dioxo-1-(3-(trifluoromethyl)phenyl)-1,2,5,6,7,8-hexahydropyrido[4,3-d]pyrimidin-3(4H)-yl)acetic acid Aqueous sodium hydroxide (1 M, 1.4 mL, 1.4 mmol) is added to a suspension of ethyl 2-(4-(4-cyanophenyl)-6-methyl-2,5-dioxo-1-(3-(trifluoromethyl)phenyl)-1,2,5,6,7,8-hexahydropyrido[4,3-d]pyrimidin-3(4H)-yl)acetate (intermediate 11, 365 mg, 0.71 mmol) in tetrahydrofuran (10 mL) and the mixture is stirred at room temperature over night. All volatiles are removed under reduced pressure, and the residue is dissolved in water (25 mL). Aqueous hydrogen chloride (1 M, 1.4 mL, 1.4 mmol) is added and the mixture is stirred for 30 min. The precipitate is filtered, washed with water and dried. Yield: 272 mg; ESI mass spectrum [M+H]⁺=485; Retention time HPLC: 0.61 min (Z011_S03).

Intermediate 13

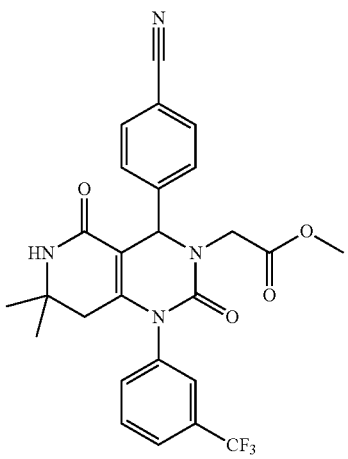

Methyl 2-(4-(4-Cyanophenyl)-7,7-dimethyl-2,5-dioxo-1-(3-(trifluoromethyl)phenyl)-1,2,5,6,7,8-hexahydropyrido[4,3-d]pyrimidin-3(4H)-yl)acetate Lithium diisopropylamide (2.0 M in tetrahydrofuran, 125 µL, 0.25 mmol) is added to a solution of 4-(7,7-dimethyl-2,5-dioxo-1-(3-(trifluoromethyl)phenyl)-1,2,3,4,5,6,7,8-octahydropyrido[4,3-d]pyrimidin-4-yl)benzonitrile (example 3), 100 mg, 0.23 mmol) in N,N-dimethylformamide (5.0 mL). Methyl bromoacetate (25 µL, 0.27 mmol) is added, and the mixture is stirred at room temperature for 4 h. Another portion of lithium diisopropylamide (2.0 M in tetrahydrofuran, 56 µL, 0.11 mmol) and methyl bromoacetate (10 µL, 0.11 mmol) is added, and the mixture is stirred over night. Water is added, and the mixture is extracted twice with dichloromethane. The combined organic layers are dried over Na$_2$SO$_4$ and concentrated under reduced pressure, and the residue is purified by preparative reversed-phase HPLC (Xbridge™-C$_{18}$, gradient of acetonitrile in water, 0.1% NH$_3$). Yield: 24 mg; ESI mass spectrum [M+H]$^+$=513; Retention time HPLC: 1.02 min (V011_S01).

Intermediate 14

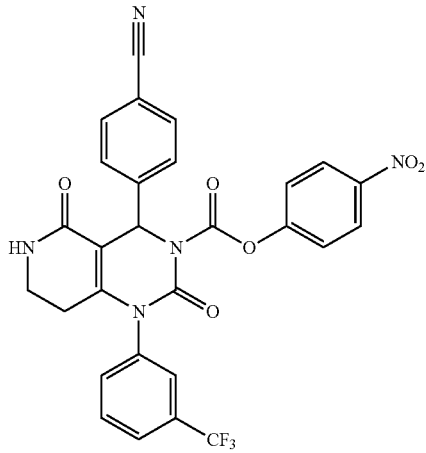 [SMILES: N#Cc1ccc(C2C3=C(CCNC3=O)N(c3cccc(C(F)(F)F)c3)C(=O)N2C(=O)Oc2ccc([N+](=O)[O-])cc2)cc1]

4-Nitrophenyl 4-(4-Cyanophenyl)-2,5-dioxo-1-[3-(trifluoromethyl)phenyl]-1H,2H,3H,4H,5H,6H,7H,8H-pyrido[4,3-d]pyrimidine-3-carboxylate A solution of 4-(2,5-dioxo-1-(3-(trifluoromethyl)phenyl)-1,2,3,4,5,6,7,8-octahydropyrido-[4,3-d]pyrimidin-4-yl)benzonitrile (example 1, 50 mg, 0.12 mmol), 4-nitrophenyl chloroformate (37 mg, 0.18 mmol) and a tip of a spatula of 4-dimethylaminopyridine in toluene (3 mL) is treated with triethylamine (150 µL) and heated in a microwave at 150° C. for 15 min. All volatiles are evaporated under reduced pressure, and the residue is dissolved in acetonitrile and purified by preparative reversed-phase HPLC (Agilent ZORBAX™ SB-C$_{18}$, gradient of acetonitrile in water, 0.15% formic acid). Yield: 25 mg, ESI mass spectrum [M+H]$^+$=578; Retention time HPLC: 1.05 min (Z017_504).

Intermediate 15

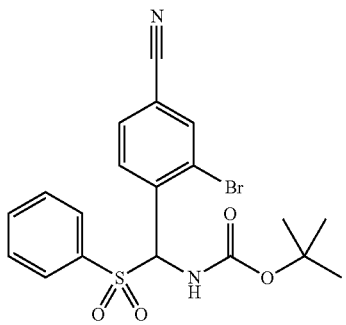 [SMILES: CC(C)(C)OC(=O)NC(c1ccc(C#N)cc1Br)S(=O)(=O)c1ccccc1]

Tert-butyl N-[(Benzenesulfonyl)(2-bromo-4-cyanophenyl)methyl]carbamate

Formic acid (65.2 mL, 1.73 mol) is added to a mixture of tert-butyl carbamate (31.6 g, 270 mmol), 3-bromo-4-formylbenzonitrile (56.7 g, 270 mmol), sodium benzenesulfinate (44.3 g, 270 mmol), tetrahydrofuran (170 mL) and water (340 mL). The mixture is stirred at room temperature for 6 days, and the precipitate is filtered. The precipitate is digested in acetonitrile (300 mL), filtered and washed with cold acetonitrile. Yield: 95.2 g. ESI mass spectrum: [($^{79}$Br)-M+H]$^+$=451, [($^{81}$Br)-M+H]$^+$=453; Retention time HPLC: 0.66 min (X012_S01).

Intermediate 16

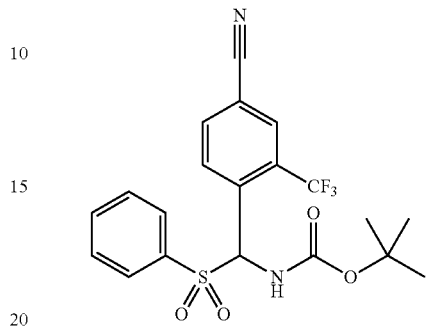

Tert-butyl N-[(Benzenesulfonyl)[4-cyano-2-(trifluoromethyl)phenyl]methyl]carbamate The title compound is prepared in analogy to tert-butyl N-[(benzenesulfonyl)(2-bromo-4-cyanophenyl)methyl]carbamate (intermediate 15), replacing 3-bromo-4-formylbenzonitrile with 4-formyl-3-(trifluoromethyl)benzonitrile (2.00 g, 10.0 mmol) as starting material.

Yield: 1.43 g. ESI mass spectrum: [M+Na]$^+$=463; Retention time HPLC: 1.10 min (Z017_S04).

Intermediate 17

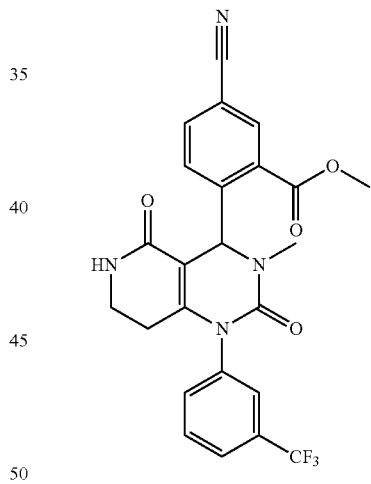

Methyl 5-Cyano-2-{3-methyl-2,5-dioxo-1-[3-(trifluoromethyl)phenyl]-1H,2H,3H,4H,5H,6H,7H,8H-pyrido[4,3-d]pyrimidin-4-yl}benzoate A mixture of 3-bromo-4-{3-methyl-2,5-dioxo-1-[3-(trifluoromethyl)phenyl]-1H,2H,3H,4H,5H,6H,7H,8H-pyrido[4,3-d]pyrimidin-4-yl}benzonitrile (example 22, 79 mg, 0.16 mmol), sodium acetate (38 mg, 0.47 mmol) and [1,1'-bis(diphenylphosphino)-ferrocene]dichloropalladium(II) (1:1 complex with dichloromethane, 13 mg, 16 µmol) in methanol (2.0 mL) is treated with carbon monoxide (5 bar) and stirred at 100° C. over night.

All volatiles are removed under reduced pressure, and the residue is purified by preparative reversed-phase HPLC (Agilent ZORBAX™ SB-C$_{18}$, gradient of acetonitrile in water, 0.15% trifluoroacetic acid). Yield: 40 mg, ESI mass spectrum [M+H]$^+$=485; Retention time HPLC: 0.98 min (Z017_504).

Intermediate 18

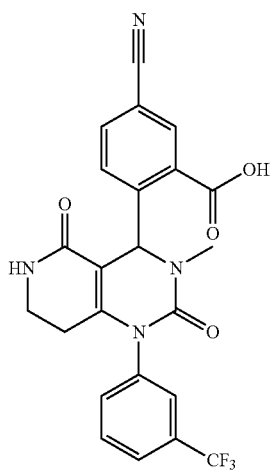 [SMILES: CN1C(=O)N(c2cccc(C(F)(F)F)c2)C2=C(C(=O)NCC2)C1c1ccc(C#N)cc1C(=O)O]

5-Cyano-2-{3-methyl-2,5-dioxo-1-[3-(trifluoromethyl)phenyl]-1H,2H,3H,4H,5H,6H,7H,8H-pyrido[4,3-d]pyrimidin-4-yl}benzoic acid A mixture of methyl 5-cyano-2-{3-methyl-2,5-dioxo-1-[3-(trifluoromethyl)phenyl]-1H,2H,3H,4H,5H,6H,7H,8H-pyrido[4,3-d]pyrimidin-4-yl}benzoate (intermediate 17, 44 mg, 91 μmol), lithium hydroxide (5.4 mg, 0.23 mmol), dioxane (1.0 mL) and water (0.5 mL) is stirred at room temperature for 1 h. Water is added, and the mixture is acidified with aqueous hydrogen chloride (1 M) and extracted with ethyl acetate. The organic layer is extracted with water and dried over Na$_2$SO$_4$. Most volatiles are removed pressure and the residue is treated with methy tert-butyl ether. The precipitate is filtered and dried.

Yield: 23 mg. ESI mass spectrum [M+H]$^+$=471; Retention time HPLC: 0.91 min (Z017_504).

Intermediate 19

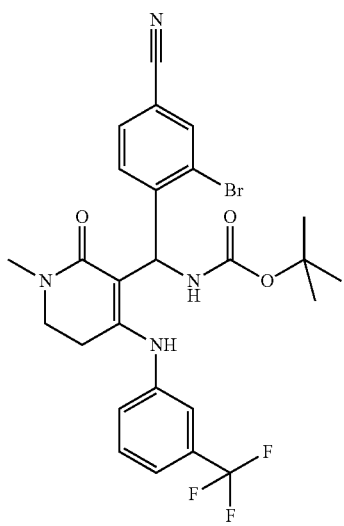 [SMILES: CN1CCC(Nc2cccc(C(F)(F)F)c2)=C(C(NC(=O)OC(C)(C)C)c2ccc(C#N)cc2Br)C1=O]

tert-Butyl N-[(2-Bromo-4-cyanophenyl)(1-methyl-2-oxo-4-{[3-(trifluoromethyl)-phenyl]amino}-1,2,5,6-tetrahydropyridin-3-yl)methyl]carbamate Sodium hydride (60% in mineral oil, 212 mg, 5.32 mmol) is added to a mixture of 1-methyl-4-(3-(trifluoromethyl) phenylamino)-5,6-dihydropyridin-2(1H)-one (intermediate 10, 1.38 g, 5.10 mmol) and methyltetrahydrofuran (10 mL), and the mixture is stirred at room temperature for 10 min Tert-butyl N-[(benzenesulfonyl)(2-bromo-4-cyanophenyl)-methyl]carbamate (intermediate 15, 2.00 g, 4.43 mmol) is added, and the mixture is stirred at room temperature for 4 h. Ethyl acetate (50 mL) is added, and the mixture is extracted twice with water. The organic layer is washed with brine, dried over Na$_2$SO$_4$ and concentrated under reduced pressure. Yield: 3.30 g (4.31 mmol based on 75% purity). ESI mass spectrum: [($^{79}$Br)-M+H]$^+$=579, [($^{81}$Br)-M+H]$^+$=581; Retention time HPLC: 1.18 min (Z017_S04).

Intermediate 20

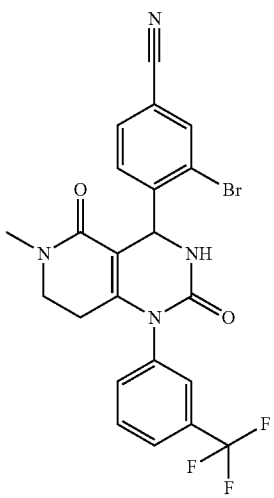 [SMILES: CN1CCC2=C(C1=O)C(c1ccc(C#N)cc1Br)NC(=O)N2c1cccc(C(F)(F)F)c1]

3-Bromo-4-{6-methyl-2,5-dioxo-1-[3-(trifluoromethyl)phenyl]-1H,2H,3H,4H,5H,6H,7H,8H-pyrido[4,3-d]pyrimidin-4-yl}benzonitrile A solution of tert-butyl N-[(2-bromo-4-cyanophenyl)(1-methyl-2-oxo-4-{[3-(trifluoromethyl)phenyl]amino}-1,2,5,6-tetrahydropyridin-3-yl)methyl]carbamate (intermediate 19, 2.80 g, 3.62 mmol based on 75% purity) in acetonitrile (20 mL) is cooled in an ice bath at 0° C. and treated with trimethylsilyl iodide (1.03 mL, 7.25 mmol). The mixture is stirred at 0° C. for 30 min and then treated with water (260 μL). The mixture is dried over Na$_2$SO$_4$ and filtered. The filtrate is treated with 1,1'-carbonyldiimidazole (3.92 g, 24.16 mmol), stirred at room temperature over night and concentrated under reduced pressure. Water is added, and the mixture is treated in an ultrasound bath for a few minutes. The precipitate is filtered and dried. Yield: 2.30 g (2.91 mmol based on 75% purity). ESI mass spectrum: [($^{79}$Br)-M+H]$^+$=505, [($^{81}$Br)-M+H]$^+$=507; Retention time HPLC: 0.84 min (Z011_S03).

Intermediate 21

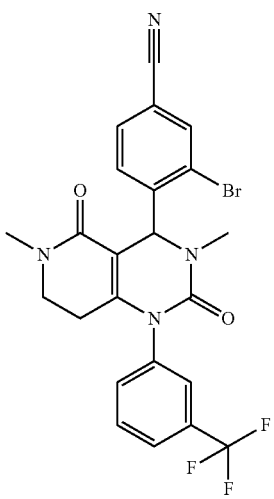 [SMILES: CN1CCC2=C(C1=O)C(c1ccc(C#N)cc1Br)N(C)C(=O)N2c1cccc(C(F)(F)F)c1]

3-Bromo-4-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzonitrile Cesium carbonate (2.37 g, 7.28 mmol) is added to a mixture of 3-bromo-4-{6-methyl-2,5-dioxo-1-[3-(trifluoromethyl)phenyl]-1H,2H,3H,4H,5H,6H,7H,8H-pyrido[4,3-d]-pyrimidin-4-yl}benzonitrile (intermediate 20, 2.30 g, 2.91 mmol based on 75% purity) and N,N-dimethylformamide (10 mL). Methyl iodide (680 µL, 10.9 mmol) is added, and the mixture is stirred for 3 h. The mixture is diluted with methanol and water, treated in an ultrasound bath for a few minutes and stirred for 1 h. The precipitate is filtered and dried.

Yield: 1.92 g (2.95 mmol based on 80% purity). ESI mass spectrum: [($^{79}$Br)-M+H]$^+$=519, [($^{81}$Br)-M+H]$^+$=521; Retention time HPLC: 1.03 min (Z017_S04).

Intermediate 22

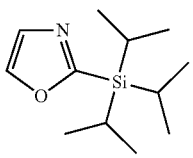

2-[Tris(propan-2-yl)silyl]-1,3-oxazole

A solution of oxazole (10.0 g, 145 mmol) in diethyl ether (400 mL) is cooled at −78° C. in a dry ice bath. n-Butyllithium (1.6 M in hexane, 100 mL, 150 mmol) is added slowly, and the mixture is stirred at −78° C. for 1 h. A solution of triisopropyl trifluormethanesulfonate (40.3 mL, 145 mmol) in diethyl ether (100 mL) is added slowly, and the mixture is allowed to warm slowly to room temperature over night. All volatiles are removed under reduced pressure, and the residue is dissolved in cyclohexane. The mixture is filtered through a pad of silica gel, and the filtrate is concentrated under reduced pressure. Yield: 32.0 g. ESI mass spectrum: [M+H]$^+$=226; Retention time HPLC: 1.43 min (Z001_002).

Intermediate 23

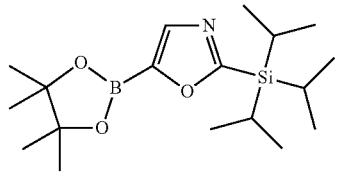 [SMILES: CC(C)[Si](c1ncc(B2OC(C)(C)C(C)(C)O2)o1)(C(C)C)C(C)C]

5-(Tetramethyl-1,3,2-dioxaborolan-2-yl)-2-(tri-tert-butylsilyl)-1,3-oxazole

A solution of 2-[tris(propan-2-yl)silyl]-1,3-oxazole (intermediate 22, 16.95 g, 75.20 mmol) in tetrahydrofuran is cooled at −78° C. in an dry ice bath. n-Butyllithium (2.5 M in hexane, 36 mL, 90 mmol) is added slowly at below −60° C., and the mixture is stirred at this temperature for 1 h. A solution of triisopropyl borate (20.3 mL, 88.5 mmol) in tetrahydrofuran (20 mL) is added at −60° C. within 25 min. The mixture is stirred at this temperature for 2 h and then allowed to warm to room temperature. A solution of 2,3-dimethyl-2,3-butandiol (8.89 g, 75.2 mmol) in tetrahydrofuran (20 mL) is added, and the mixture is stirred for 2 h. Acetic acid (6.78 g, 117.4 mmol) is added, and the mixture is stirred over night. Methyl tert-butyl ether (300 mL) is added, and the mixture is stirred for 30 min and filtered. The filtrate is concentrated under reduced pressure. Yield: 25.2 g. ESI mass spectrum: [M+H]$^+$=352; Retention time HPLC: 0.75 min (V011_S01).

Intermediate 24

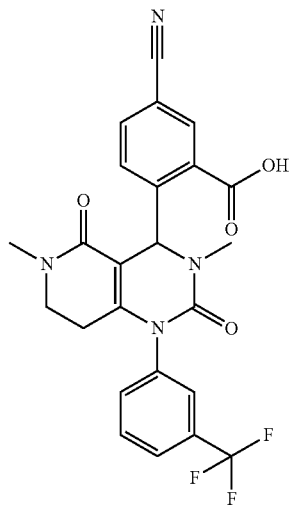 [SMILES: CN1CCC2=C(C1=O)C(c1ccc(C#N)cc1C(=O)O)N(C)C(=O)N2c1cccc(C(F)(F)F)c1]

5-Cyano-2-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzoic acid Step 1

Methyl 5-Cyano-2-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzoate A mixture of 3-bromo-4-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzonitrile (intermediate 21, 2.90 g, 4.19 mmol based on 75% purity), sodium acetate (962 mg, 11.7 mmol) and [1,1'-bis(diphenylphosphino)ferrocene]dichloropalladium(II) (1:1 complex with dichloromethane, 319 mg, 0.39 mmol) in methanol (25 mL) is treated with carbon monoxide (5 bar) and stirred at 100° C. over night. The mixture is filtered over basic aluminium oxide, and the filtrate was concentrated. The residue was treated with water, and the mixture was extracted with dichloromethane. The organic phase was dried and concentrated under reduced pressure. Yield: 2.29 g (3.67 mmol based on 80% purity), ESI mass spectrum [M+H]⁺=499; Retention time HPLC: 1.05 min (Z017_504).

Step 2

5-Cyano-2-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzoic acid Lithium hydroxide (48 mg, 2.0 mmol) is added to a mixture of methyl 5-cyano-2-{3,6-dimethyl-2,5-dioxo-1-[3-(trifluoromethyl)phenyl]-1H,2H,3H,4H,5H,6H,7H,8H-pyrido-[4,3-d]pyrimidin-4-yl}benzoate (step 1, 500 mg, 0.80 mmol based on 80% purity), 1,4-dioxane (5 mL) and water (2.5 mL), and the mixture is stirred at room temperature for 2 h. The mixture is acidified with aqueous hydrogen chloride solution (1 N), and water is added. The precipitate is filtered and dried. Yield: 290 mg. A small portion of the product (40 mg) was purified by preparative reversed-phase HPLC (Sunfire-C₁₈, gradient of acetonitrile in water, 0.1% trifluoroacetic acid). Yield: 12 mg. ESI mass spectrum [M+H]⁺=485; Retention time HPLC: 0.97 min (Z017_504).

Intermediate 25

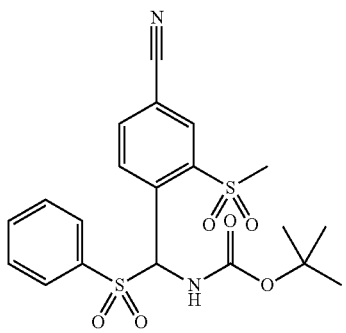 [SMILES: CC(C)(C)OC(=O)NC(c1ccc(C#N)cc1S(C)(=O)=O)S(=O)(=O)c1ccccc1]

tert-Butyl (4-Cyano-2-(methylsulfonyl)phenyl)(phenylsulfonyl)methylcarbamate

Formic acid (6.2 mL, 164 mmol) is added to a solution of tert-butyl carbamate (3.05 g, 26.0 mmol), 4-formyl-3-(methylsulfonyl)benzonitrile (5.44 g, 26.0 mmol) and sodium benzenesulfinate (4.27 g, 26.0 mmol) in a mixture of tetrahydrofuran (10 mL) and water (25 mL), and the mixture is stirred at room temperature for 4 days. Water (30 mL) is added, and the precipitate is filtered, washed with water and acetonitrile and dried Yield: 5.10 g. ESI mass spectrum: [M+H]⁺=451; Retention time HPLC: 0.59 min (X012_S01).

Intermediate 26

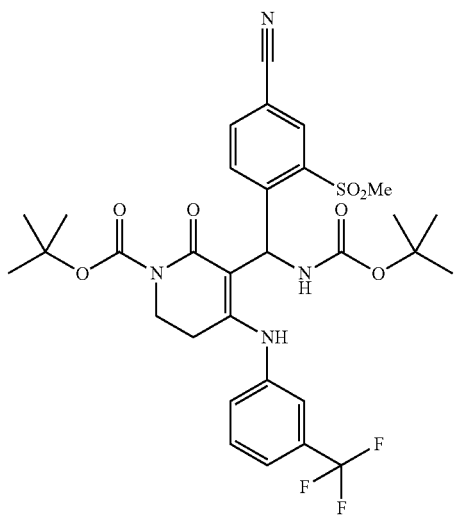 [SMILES: CC(C)(C)OC(=O)NC(C1=C(Nc2cccc(C(F)(F)F)c2)CCN(C(=O)OC(C)(C)C)C1=O)c1ccc(C#N)cc1S(C)(=O)=O]

tert-Butyl 5-({[(tert-Butoxy)carbonyl]amino}(4-cyano-2-methanesulfonylphenyl)-methyl)-6-oxo-4-{[3-(trifluoromethyl)phenyl]amino}-1,2,3,6-tetrahydropyridine-1-carboxylate Sodium hydride (60% in mineral oil, 122 mg, 2.81 mmol) is added to a mixture of tert-butyl 2-oxo-4-(3-(trifluoromethyl)phenylamino)-5,6-dihydropyridine-1(2H)-carboxylate (intermediate 3, 1.00 g, 2.81 mmol) and methyltetrahydrofuran (5 mL), and the mixture is stirred at room temperature for 10 min tert-Butyl (4-cyano-2-(methylsulfonyl)phenyl)-(phenylsulfonyl)methylcarbamate (intermediate 25, 1.14 g, 2.53 mmol) is added, and the mixture is stirred at room temperature over night. Ethyl acetate (50 mL) is added, and the mixture is extracted twice with water. The organic layer is dried over Na₂SO₄ and concentrated under reduced pressure. Yield: 1.57 mg. ESI mass spectrum: [M+H]⁺=665; Retention time HPLC: 1.06 min (Z011_503).

Intermediate 27

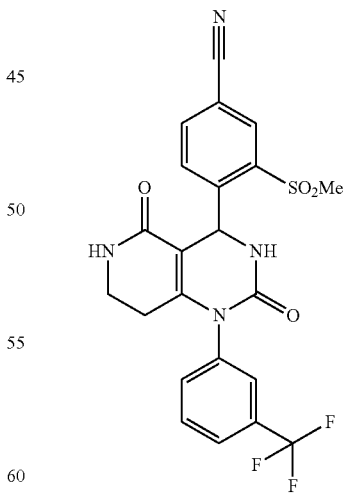

4-{2,5-Dioxo-1-[3-(trifluoromethyl)phenyl]-1H,2H,3H,4H,5H,6H,7H,8H-pyrido[4,3-d]-pyrimidin-4-yl}-3-methanesulfonylbenzonitrile A solution of hydrogen chloride in 1,4-dioxane (4 M, 1.0 mL, 8.0 mmol) is added to a mixture of tert-butyl 5-({[(tert-butoxy)carbonyl]amino}(4-cyano-2-methanesulfonylphenyl)methyl)-6-oxo-4-{[3-(trifluoromethyl)phenyl]amino}-1,2,3,6-tetrahydropyridine-1-carboxylate (intermediate 26, 780 mg, 1.17 mmol) and acetonitrile (2 mL), and the mixture is stirred at room temperature for 1 h. The mixture is filtered, and the filtrate is diluted with acetonitrile (4 mL). Triethylamine (150 µL, 1.08 mmol) and 1,1'-carbonyldiimidazole (150 mg, 0.92 mmol) is added, and the mixture is stirred for 1 h and then purified by preparative reversed-phase HPLC (Agilent ZORBAX™ SB-C$_{18}$, gradient of acetonitrile in water, 0.1% TFA). Yield: 86 mg; ESI mass spectrum: [M+H]$^+$=491; Retention time HPLC: 0.91 min (Z017_504).

Syntheses of Examples

Example 1

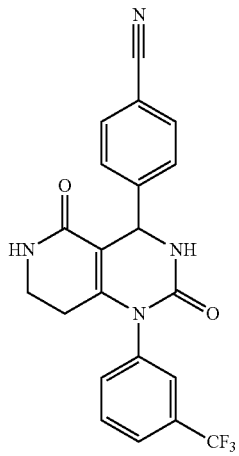 [SMILES: N#Cc1ccc(C2NC(=O)N(c3cccc(C(F)(F)F)c3)C3=C2C(=O)NCC3)cc1]

4-(2,5-Dioxo-1-(3-(trifluoromethyl)phenyl)-1,2,3,4,5,6,7,8-octahydropyrido[4,3-d]-pyrimidin-4-yl)benzonitrile Method A:

A solution of 4-(chloro(isocyanato)methyl)benzonitrile (intermediate 2, 1.97 g, 8.70 mmol) in dichloromethane (5 mL) is added to a solution of tert-butyl 2-oxo-4-(3-(trifluoromethyl)-phenylamino)-5,6-dihydropyridine-1(2H)-carboxylate (intermediate 3, 3.10 g, 8.70 mmol) in dichloromethane (15 mL) and the mixture is heated at reflux over night. The mixture is concentrated under reduced pressure and purified by preparative reversed-phase HPLC (Agilent ZORBAX™ SB-C$_{18}$, gradient of acetonitrile in water, 0.1% TFA). Yield: 464 mg; ESI mass spectrum: [M+H]$^+$=413; Retention time HPLC: 0.89 min (Z017_S04).
Method B:

Under an atmosphere of argon, a mixture of 4-(4-bromophenyl)-1-(3-(trifluoromethyl)-phenyl)-3,4,7,8-tetrahydropyrido[4,3-d]pyrimidine-2,5(1H,6H)-dione (intermediate 4, 790 mg, 1.69 mmol), zinc cyanide (259 mg, 2.20 mmol) and tetrakis(triphenylphosphine)-palladium(0) (196 mg, 169 µmol) in N,N-dimethylformamide (4 mL) is heated over night at 110° C. The mixture is cooled to room temperature, concentrated and purified by preparative reversed-phase HPLC (Agilent ZORBAX™ SB-C$_{18}$, gradient of acetonitrile in water, 0.1% TFA). Yield 473 mg; ESI mass spectrum [M+H]$^+$=413; Retention time HPLC: 0.89 min (Z017_S04).

Examples 1A and 1B: Enantiomers of Example 1

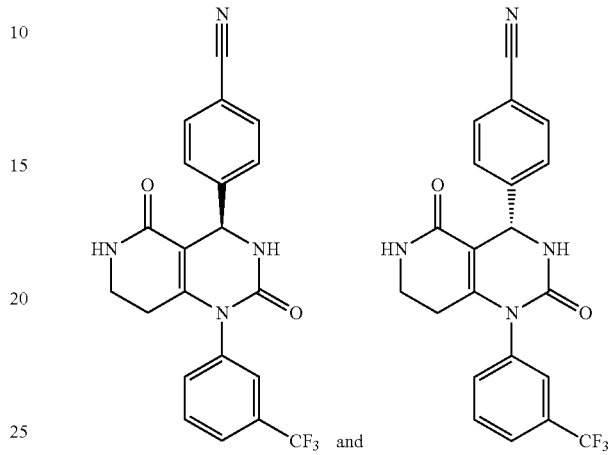

The enantiomers of racemic 4-(2,5-dioxo-1-(3-(trifluoromethyl)phenyl)-1,2,3,4,5,6,7,8-octahydropyrido[4,3-d]pyrimidin-4-yl)benzonitrile (example 1, 90 mg, 0.22 mmol) are separated by preparative supercritical fluid chromatography on a chiral phase (Daicel Chiralpak IC, 20×250 mm, 5 µm, 30% MeOH+0.2% diethylamine in supercritical CO$_2$, 40° C., 150 bar back pressure).

Example 1A

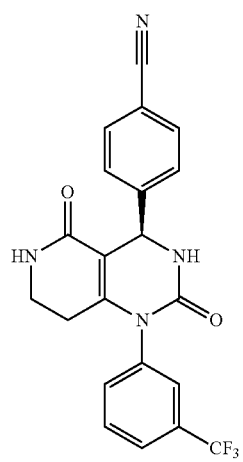

(R)-4-(2,5-Dioxo-1-(3-(trifluoromethyl)phenyl)-1,2,3,4,5,6,7,8-octahydropyrido[4,3-d]-pyrimidin-4-yl)benzonitrile Yield: 37 mg; ESI mass spectrum [M+H]$^+$=413; Retention time: 5.53 min (late eluting enantiomer) (I_IC_30_MeOH_DEA).

Example 1B

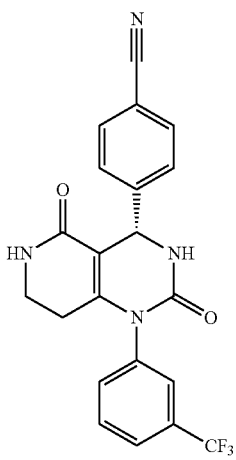 [SMILES: N#Cc1ccc([C@@H]2NC(=O)N(c3cccc(C(F)(F)F)c3)C3=C2C(=O)NCC3)cc1]

(S)-4-(2,5-Dioxo-1-(3-(trifluoromethyl)phenyl)-1,2,3,4,5,6,7,8-octahydropyrido[4,3-d]-pyrimidin-4-yl)benzonitrile Yield: 36 mg; ESI mass spectrum [M+H]$^+$=413; Retention time: 3.96 min (early eluting enantiomer) (I_IC_30_MeOH_DEA).

Example 2

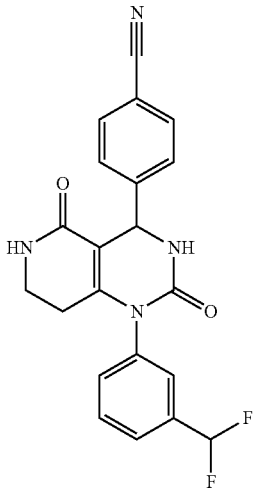

4-(1-(3-(Difluoromethyl)phenyl)-2,5-dioxo-1,2,3,4,5,6,7,8-octahydropyrido[4,3-d]-pyrimidin-4-yl)benzonitrile Method A:

A solution of 4-(chloro(isocyanato)methyl)benzonitrile (intermediate 2, 2.20 g, 9.14 mmol based on 80% purity) in dichloromethane (15 mL) is added to a mixture of tert-butyl 4-(3-(difluoromethyl)phenylamino)-2-oxo-5,6-dihydropyridine-1(2H)-carboxylate (intermediate 5, 3.10 g, 9.14 mmol) and dichloromethane (15 mL), and the mixture is stirred at room temperature over night. The mixture is diluted with water and extracted twice with dichloromethane. The combined organic layers are dried and concentrated under reduced pressure, and the residue is purified by preparative reversed-phase HPLC (Xbridge™-C$_{18}$, gradient of acetonitrile in water, 0.1% TFA). Yield: 566 mg; ESI mass spectrum: [M+H]$^+$=395; Retention time HPLC: 0.54 min (X011_S03).

Method B:

Under an atmosphere of argon, a mixture of 4-(4-bromophenyl)-1-(3-(difluoromethyl)-phenyl)-3,4,7,8-tetrahydropyrido[4,3-d]pyrimidine-2,5(1H,6H)-dione (intermediate 6, 313 mg, 0.698 mg), zinc cyanide (139 mg, 1.19 mmol) and tetrakis(triphenylphosphine)palladium(0) (81 mg, 70 µmol) in N,N-dimethylformamide (9 mL) is heated at 110° C. for 2 h and then cooled to room temperature. Water is added and the mixture is extracted twice with dichloromethane. The combined organic layers are concentrated and the residue is purified by preparative reversed-phase HPLC (Waters Xbridge™-C$_{18}$, gradient of acetonitrile in water, 0.1% TFA). Yield: 96 mg, ESI mass spectrum [M+H]$^+$=395; Retention time HPLC: 0.44 min (X012_S01).

Examples 2A and 2B: Enantiomers of Example 2

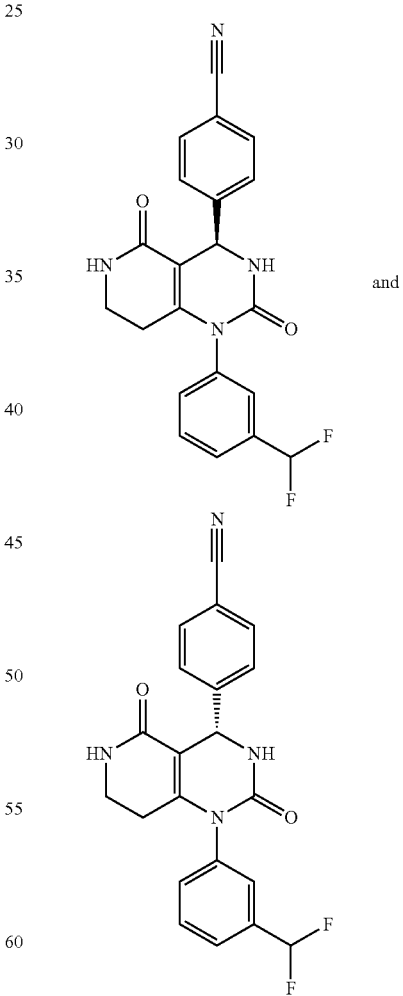

and

The enantiomers of racemic 4-(1-(3-(difluoromethyl)phenyl)-2,5-dioxo-1,2,3,4,5,6,7,8-octahydropyrido[4,3-d]pyrimidin-4-yl)benzonitrile (example 2, 90 mg, 0.23 mmol) are separated by preparative supercritical fluid chromatography on a chiral phase (Daicel Chiralpak IC, 10×250 mm, 5 μm, 40% MeOH+0.2% diethylamine in supercritical CO$_2$, 40° C., 150 bar back pressure).

Example 2A

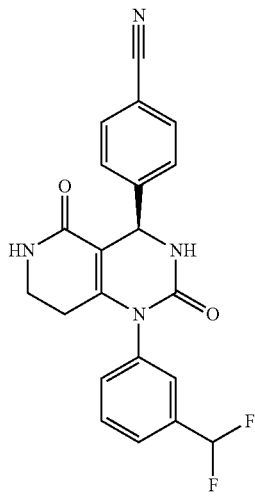 [SMILES: N#Cc1ccc([C@H]2NC(=O)N(c3cccc(C(F)F)c3)C3=C2C(=O)NCC3)cc1]

(R)-4-(1-(3-(Difluoromethyl)phenyl)-2,5-dioxo-1,2,3,4,5,6,7,8-octahydropyrido[4,3-d]-pyrimidin-4-yl)benzonitrile Yield: 31 mg; ESI mass spectrum [M+H]$^+$=395; Retention time: 5.37 min (late eluting enantiomer) (I_IC_40_MeOH_DEA).

Example 2B

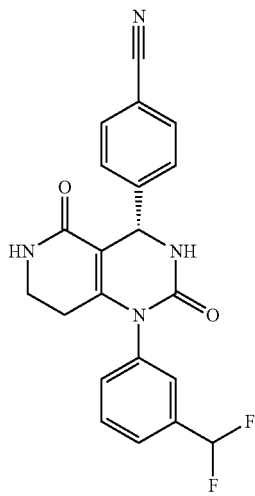

(S)-4-(1-(3-(Difluoromethyl)phenyl)-2,5-dioxo-1,2,3,4,5,6,7,8-octahydropyrido[4,3-d]-pyrimidin-4-yl)benzonitrile Yield: 34 mg; ESI mass spectrum [M+H]$^+$=395; Retention time: 3.94 min (early eluting enantiomer) (I_IC_40_MeOH_DEA).

Example 3

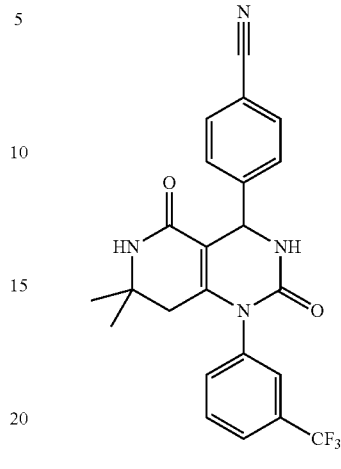

4-(7,7-Dimethyl-2,5-dioxo-1-(3-(trifluoromethyl)phenyl)-1,2,3,4,5,6,7,8-octahydropyrido[4,3-d]pyrimidin-4-yl)benzonitrile Under an atmosphere of argon, a mixture of 4-(4-bromophenyl)-7,7-dimethyl-1-(3-(trifluoromethyl)phenyl)-3,4,7,8-tetrahydropyrido[4,3-d]pyrimidine-2,5 (1H,6H)-dione (intermediate 8, 560 mg, 1.13 mmol), zinc cyanide (200 mg, 1.70 mmol) and tetrakis(triphenylphosphine)palladium(0) (130 mg, 112 μmol) in N,N-dimethylformamide (5 mL) is heated at 110° C. over night and then cooled to room temperature. Water is added and the mixture is filtered. The precipitate is suspended in a mixture of methanol and ethyl acetate, stirred for 30 min, filtered and washed with ethyl acetate. Yield: 280 mg; ESI mass spectrum [M+H]$^+$=441; Retention time HPLC: 1.31 min (V001_006).

Example 4

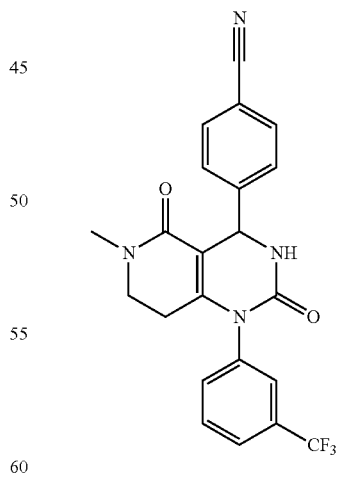

4-(6-Methyl-2,5-dioxo-1-(3-(trifluoromethyl)phenyl)-1,2,3,4,5,6,7,8-octahydropyrido[4,3-d]pyrimidin-4-yl)benzonitrile A solution of 4-(chloro(isocyanato)methyl)benzonitrile (intermediate 2, 3.50 g, 18.2 mmol) in dichloromethane (5 mL) is added to a solution of 1-methyl-4-(3-(trifluoromethyl)phenylamino)-5,6-dihydropyridin-2(1H)-one (intermediate 10, 4.91 g, 18.2 mmol) in dichloromethane (15 mL), and the mixture is heated at reflux for 4 h. The mixture is concentrated under reduced pressure and purified by preparative reversed-phase HPLC (Waters SunFire™-C$_{18}$, gradient of acetonitrile in water, 0.1% formic acid). Yield: 1.11 g; ESI mass spectrum: [M+H]$^+$=427; Retention time HPLC: 0.97 min (Z018_S04).

Examples 4A and 4B

Enantiomers of Example 4

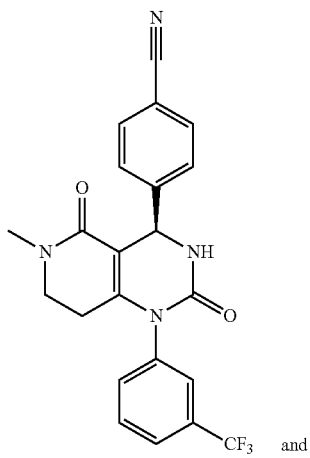

and

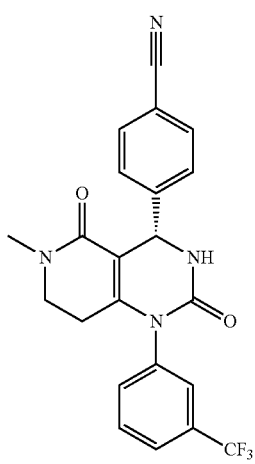

The enantiomers of racemic 4-(6-methyl-2,5-dioxo-1-(3-(trifluoromethyl)phenyl)-1,2,3,4,5,6,7,8-octahydropyrido[4,3-d]pyrimidin-4-yl)benzonitrile (example 4, 80 mg, 0.17 mmol) are separated by preparative supercritical fluid chromatography on a chiral phase (Daicel Chiralpak IB, 20×250 mm, 5 μm, 20% MeOH+0.2% diethylamine in supercritical CO$_2$, 40° C., 120 bar back pressure).

Example 4A

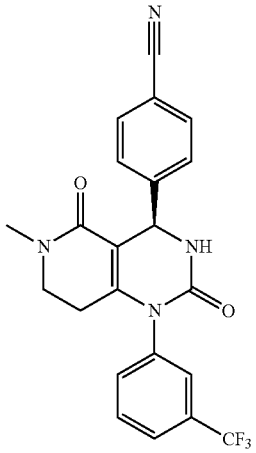 [SMILES: CN1CCC2=C(C1=O)[C@@H](c1ccc(C#N)cc1)NC(=O)N2c1cccc(C(F)(F)F)c1]

(R)-4-(6-Methyl-2,5-dioxo-1-(3-(trifluoromethyl)phenyl)-1,2,3,4,5,6,7,8-octahydropyrido[4,3-d]pyrimidin-4-yl)benzonitrile Yield: 34 mg; ESI mass spectrum [M+H]$^+$=427; Retention time: 2.29 min (early eluting enantiomer) (I_IB_20_MeOH_DEA).

Example 4B

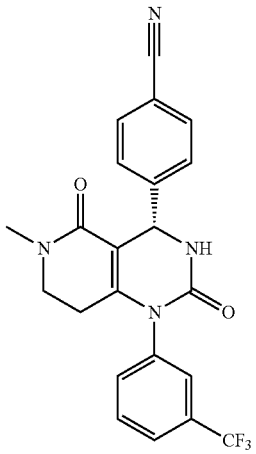 [SMILES: CN1CCC2=C(C1=O)[C@H](c1ccc(C#N)cc1)NC(=O)N2c1cccc(C(F)(F)F)c1]

(S)-4-(6-Methyl-2,5-dioxo-1-(3-(trifluoromethyl)phenyl)-1,2,3,4,5,6,7,8-octahydropyrido[4,3-d]pyrimidin-4-yl)benzonitrile Yield: 34 mg; ESI mass spectrum [M+H]$^+$=427; Retention time: 2.94 min (late eluting enantiomer) (I_IB_20_MeOH_DEA).

Example 5

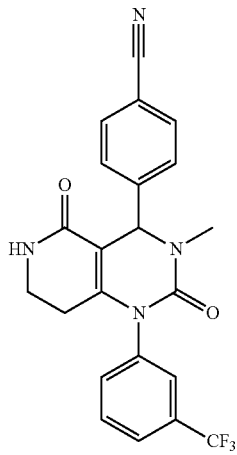 [SMILES: CN1C(=O)N(c2cccc(C(F)(F)F)c2)C2=C(C(=O)NCC2)C1c1ccc(C#N)cc1]

4-(3-Methyl-2,5-dioxo-1-(3-(trifluoromethyl)phenyl)-1,2,3,4,5,6,7,8-octahydropyrido-[4,3-d]pyrimidin-4-yl)benzonitrile A solution of 4-(2,5-dioxo-1-(3-(trifluoromethyl)phenyl)-1,2,3,4,5,6,7,8-octahydropyrido-[4,3-d]pyrimidin-4-yl)benzonitrile (example 1, 30 mg, 73 μmol) in dry N,N-dimethylformamide (500 μL) is cooled at 0° C. in an ice bath and treated with lithium diisopropylamide (2.0 M in tetrahydrofuran, 40 μL, 80 μmol). Iodomethane (6 μL, 0.1 mmol) is added and the mixture is allowed to warm to room temperature. After 1 h water is added and the mixture is extracted twice with dichloromethane. The combined organic layers are concentrated and the residue is purified by preparative reversed-phase HPLC (Waters Xbridge™-$C_{18}$, gradient of acetonitrile in water, 0.1% TFA). Yield: 8 mg; ESI mass spectrum $[M+H]^+=427$; Retention time HPLC: 1.06 min (V012_S01).

Examples 6 and 7

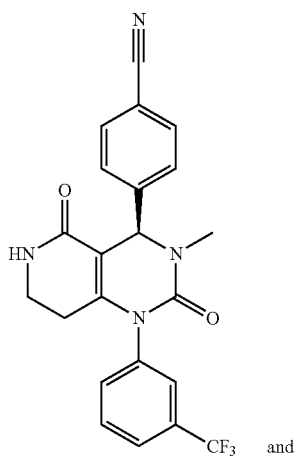

and

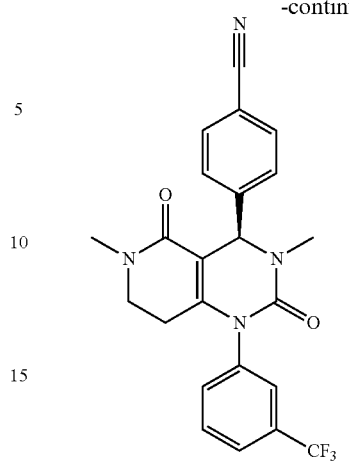

A solution of (R)-4-(2,5-dioxo-1-(3-(trifluoromethyl)phenyl)-1,2,3,4,5,6,7,8-octahydropyrido[4,3-d]pyrimidin-4-yl)benzonitrile (example 1A, 30 mg, 73 μmol) in dry tetrahydrofuran (0.5 mL) is added to a suspension of sodium hydride (60% in mineral oil, 4 mg, 100 μmol) in tetrandrofuran (0.5 mL). After 20 min, iodomethane (6 μL, 100 μmol) is added and the mixture is stirred at room temperature for 1 h. Water is added and the mixture is extracted with dichloromethane. The organic layer is concentrated and the residue is purified by preparative reversed-phase HPLC (Agilent ZORBAX™ SB-$C_{18}$, gradient of acetonitrile in water, 0.1% TFA).

Example 6

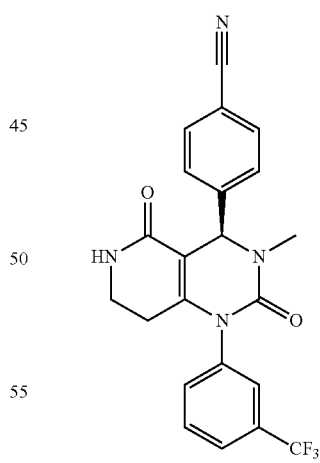

(R)-4-(3-Methyl-2,5-dioxo-1-(3-(trifluoromethyl)phenyl)-1,2,3,4,5,6,7,8-octahydropyrido[4,3-d]pyrimidin-4-yl)benzonitrile Yield 5 mg; ESI mass spectrum $[M+H]^+=427$; Retention time HPLC: 0.95 min (Z017_S04).

Example 7

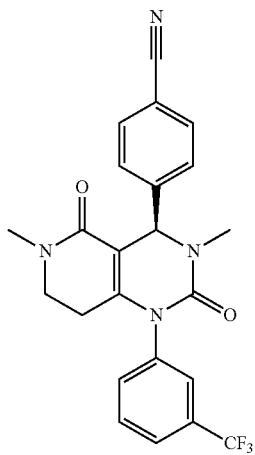 [SMILES: CN1CCC2=C(C1=O)[C@@H](c1ccc(C#N)cc1)N(C)C(=O)N2c1cccc(C(F)(F)F)c1]

(R)-4-(3,6-Dimethyl-2,5-dioxo-1-(3-(trifluoromethyl)phenyl)-1,2,3,4,5,6,7,8-octahydropyrido[4,3-d]pyrimidin-4-yl)benzonitrile Yield 3 mg; ESI mass spectrum [M+H]$^+$=441; Retention time HPLC: 1.00 min (Z017_504). LB 5FAI00691PB1

Examples 8A and 8B

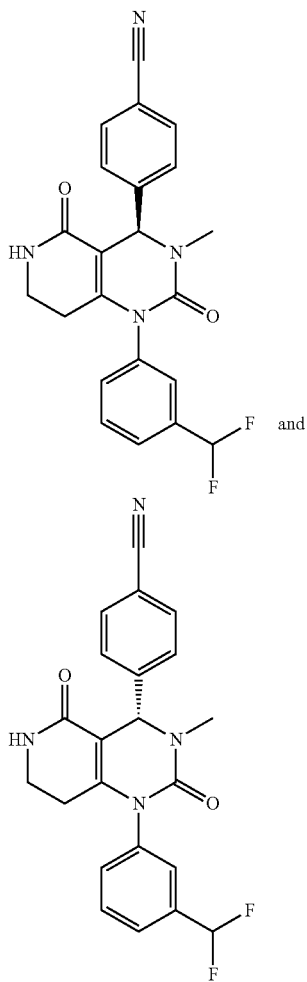

and

Step 1

4-(1-(3-(Difluoromethyl)phenyl)-3-methyl-2,5-dioxo-1,2,3,4,5,6,7,8-octahydropyrido-[4,3-d]pyrimidin-4-yl)benzonitrile Cesium carbonate (853 mg, 2.62 mmol) is added to a solution of 4-(1-(3-(difluoromethyl)-phenyl)-2,5-dioxo-1,2,3,4,5,6,7,8-octahydropyrido[4,3-d]pyrimidin-4-yl)benzonitrile (example 2, 516 mg, 1.31 mmol) in N,N-dimethylformamide (10 mL). Methyl iodide (130 µL, 2.09 mmol) is added, and the mixture is stirred at room temperature for 2 h. Another portion of methyl iodide (50 µL, 0.80 mmol) is added, and the mixture is stirred for 3 days. Water is added, and the mixture is purified by preparative reversed-phase HPLC (Waters Xbridge™-C$_{18}$, gradient of acetonitrile in water, 0.1% NH$_3$). Yield: 458 mg; ESI mass spectrum [M+H]$^+$=409; Retention time HPLC: 0.50 min (X011_503).

Step 2

The enantiomers of racemic 4-(1-(3-(difluoromethyl)phenyl)-3-methyl-2,5-dioxo-1,2,3,4,5,6,7,8-octahydropyrido[4,3-d]pyrimidin-4-yl)benzonitrile (step 1, 458 mg, 1.12 mmol) are separated by preparative supercritical fluid chromatography on a chiral phase (Daicel Chiralpak IB, 20×250 mm, 5 µm, 15% MeOH+0.2% diethylamine in supercritical CO$_2$, 40° C., 120 bar back pressure).

Example 8A

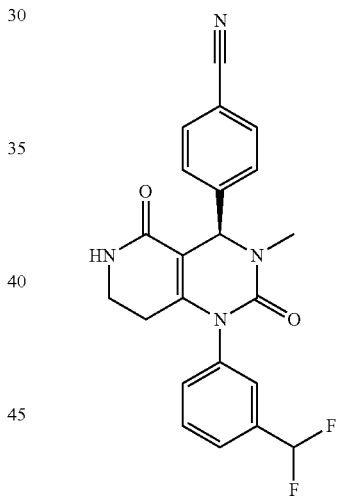

(R)-4-(1-(3-(Difluoromethyl)phenyl)-3-methyl-2,5-dioxo-1,2,3,4,5,6,7,8-octahydropyrido[4,3-d]pyrimidin-4-yl)benzonitrile Yield: 215 mg; ESI mass spectrum [M+H]$^+$=409; Retention time: 2.74 min (early eluting enantiomer) (I_IB_20_MeOH_DEA).

Alternatively, example 8A can be prepared as follows:

Lithium diisopropylamide (2 M in tetrahydrofuran, 14 µL, 28 µmol) is added at 0° C. to a solution of (R)-4-(1-(3-(difluoromethyl)phenyl)-2,5-dioxo-1,2,3,4,5,6,7,8-octahydropyrido-[4,3-d]pyrimidin-4-yl)benzonitrile (example 2A, 10 mg, 25 µmol) in N,N-dimethylformamide (0.5 mL). Methyl iodide (2 µL, 0.03 mmol) is added and the mixture is warmed at room temperature, stirred for 1 h and then purified by preparative reversed-phase HPLC (Waters Xbridge™-C$_{18}$, gradient of acetonitrile in water, 0.1% TFA). Yield: 4 mg, ESI mass spectrum [M+H]$^+$=409; Retention time HPLC: 0.49 min (X012_S01).

Example 8B

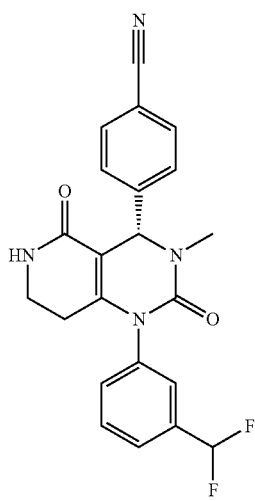 [SMILES: CN1C(=O)N(c2cccc(C(F)F)c2)C2=C(C(=O)NCC2)[C@@H]1c1ccc(C#N)cc1]

(S)-4-(1-(3-(Difluoromethyl)phenyl)-3-methyl-2,5-dioxo-1,2,3,4,5,6,7,8-octahydropyrido[4,3-d]pyrimidin-4-yl)benzonitrile Yield: 225 mg; ESI mass spectrum [M+H]$^+$=409; Retention time: 3.21 min (late eluting enantiomer) (I_IB_20_MeOH_DEA).

Example 9

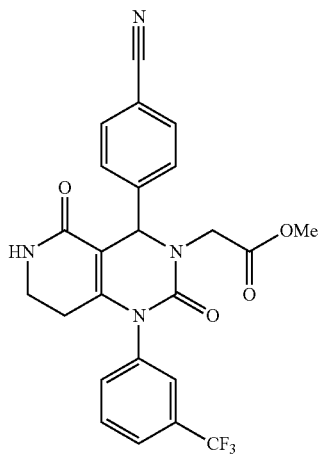 [SMILES: COC(=O)CN1C(=O)N(c2cccc(C(F)(F)F)c2)C2=C(C(=O)NCC2)C1c1ccc(C#N)cc1]

Methyl 2-(4-(4-Cyanophenyl)-2,5-dioxo-1-(3-(trifluoromethyl)phenyl)-1,2,5,6,7,8-hexahydropyrido[4,3-d]pyrimidin-3(4H)-yl)acetate A solution of 4-(2,5-dioxo-1-(3-(trifluoromethyl)phenyl)-1,2,3,4,5,6,7,8-octahydropyrido-[4,3-d]pyrimidin-4-yl)benzonitrile (example 1, 100 mg, 243 mmol) in dry N,N-dimethylformamide (3 mL) is cooled at 0° C. in an ice bath and treated with lithium diisopropylamide (2 M in tetrahydrofuran, 133 μL, 266 μmol). After 5 min ethyl bromoacetate (27 μL, 0.29 mmol) is added and the mixture is stirred at room temperature for 30 min Water is added and the mixture is extracted twice with dichloromethane. The combined organic layers are concentrated and the residue is purified by preparative reversed-phase HPLC (Waters Xbridge™-C$_{18}$, gradient of acetonitrile in water, 0.1% NH$_3$). Yield: 25 mg; ESI mass spectrum [M+H]$^+$=485; Retention time HPLC: 1.07 min (V012_S01).

Example 10

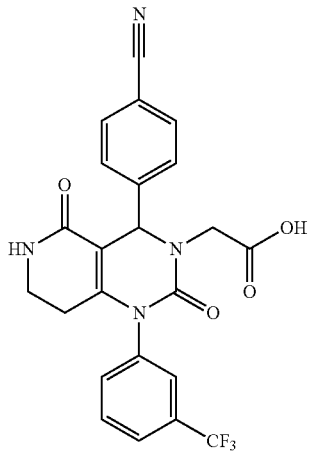 [SMILES: N#Cc1ccc(C2C3=C(CCNC3=O)N(c3cccc(C(F)(F)F)c3)C(=O)N2CC(=O)O)cc1]

2-(4-(4-Cyanophenyl)-2,5-dioxo-1-(3-(trifluoromethyl)phenyl)-1,2,5,6,7,8-hexahydropyrido[4,3-d]pyrimidin-3(4H)-yl)acetic acid Aqueous sodium hydroxide (1 M, 87 μL, 87 μmol) is added to a solution of methyl 2-(4-(4-cyanophenyl)-2,5-dioxo-1-(3-(trifluoromethyl)phenyl)-1,2,5,6,7,8-hexahydropyrido[4,3-d]pyrimidin-3(4H)-yl)acetate (example 9, 22 mg, 45 μmol) in dioxane/water (1:1, 1 mL). After 2 h the mixture is diluted with water and washed with diethyl ether. The aqueous phase is acidified with aqueous hydrogen chloride (1 M) and extracted with diethyl ether. The organic layer is dried (Na$_2$SO$_4$) and concentrated. Yield: 15 mg; ESI mass spectrum [M+H]$^+$=471; Retention time HPLC: 0.69 min (V011_S01).

Example 11

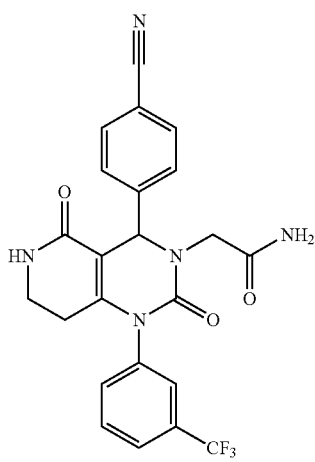 [SMILES: N#Cc1ccc(C2C3=C(CCNC3=O)N(c3cccc(C(F)(F)F)c3)C(=O)N2CC(N)=O)cc1]

2-(4-(4-Cyanophenyl)-2,5-dioxo-1-(3-(trifluoromethyl)phenyl)-1,2,5,6,7,8-hexahydropyrido[4,3-d]pyrimidin-3(4H)-yl)acetamide Triethylamine (30 μL, 0.21 mmol) and O-(7-azabenzotriazol-1-yl)-N,N,N',N'-tetramethyluronium hexafluorophosphate (16 mg, 42 µmol) are added to a solution of 2-(4-(4-cyanophenyl)-2,5-dioxo-1-(3-(trifluoromethyl)phenyl)-1,2,5,6,7,8-hexahydropyrido[4,3-d]pyrimidin-3(4H)-yl)acetic acid (example 10, 20 mg, 43 µmol) in N,N-dimethylformamide (0.5 mL). After 5 min, ammonia (0.5 M in dioxane, 850 µL, 425 µmol) is added and the mixture is stirred at room temperature for 30 min. The mixture is diluted with N,N-dimethylformamide (1 mL) and purified by preparative reversed-phase HPLC (Waters Xbridge™-$C_{18}$, gradient of acetonitrile in water, 0.1% $NH_3$). Yield: 7 mg; ESI mass spectrum $[M+H]^+$=470; Retention time HPLC: 0.91 min (V011_S01).

Example 12

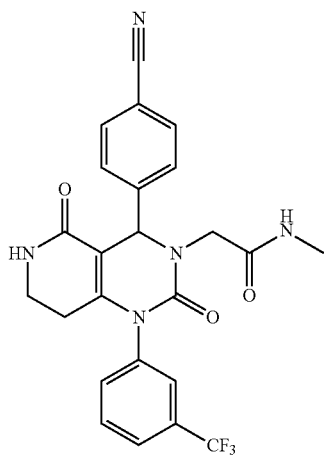 [SMILES: CNC(=O)CN1C(=O)N(c2cccc(C(F)(F)F)c2)C2=C(C(=O)NCC2)C1c1ccc(C#N)cc1]

2-(4-(4-Cyanophenyl)-2,5-dioxo-1-(3-(trifluoromethyl)phenyl)-1,2,5,6,7,8-hexahydropyrido[4,3-d]pyrimidin-3(4H)-yl)-N-methylacetamide Triethylamine (70 µL, 0.50 mmol) and O-(7-azabenzotriazol-1-yl)-N,N,N',N'-tetramethyluronium hexafluorophosphate (32 mg, 100 µmol) are added to a solution of 2-(4-(4-cyanophenyl)-2,5-dioxo-1-(3-(trifluoromethyl)phenyl)-1,2,5,6,7,8-hexahydropyrido[4,3-d]pyrimidin-3(4H)-yl) acetic acid (example 10, 47 mg, 100 µmol) in N,N-dimethylformamide (1.2 mL). After 5 min, methylamine (2 M in tetrahydrofuran, 100 µL, 200 µmol) is added and the mixture is stirred at room temperature over night and purified by preparative reversed-phase HPLC (Waters Xbridge™-$C_{18}$, gradient of acetonitrile in water, 0.1% $NH_3$).

Yield: 32 mg; ESI mass spectrum $[M+H]^+$=484; Retention time HPLC: 0.76 min (Z011_S03).

Examples 12A and 12B: Enantiomers of Example 12

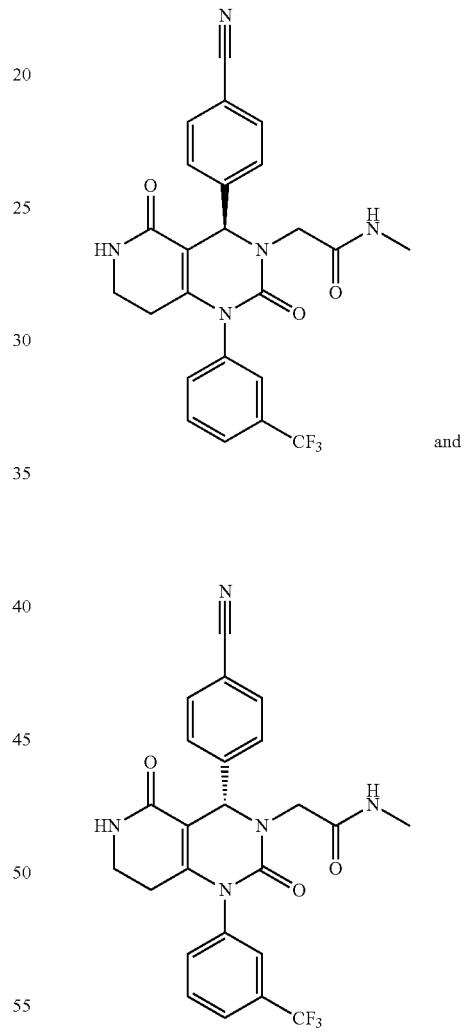

The enantiomers of racemic 2-(4-(4-cyanophenyl)-2,5-dioxo-1-(3-(trifluoromethyl)phenyl)-1,2,5,6,7,8-hexahydropyrido[4,3-d]pyrimidin-3(4H)-yl)-N-methylacetamide (example 12, 211 mg, 0.53 mmol) are separated by preparative supercritical fluid chromatography on a chiral phase (Daicel Chiralpak IA, 20×250 mm, 5 µm, 20% MeOH+0.2% diethylamine in supercritical $CO_2$, 40° C., 150 bar back pressure).

Example 12A

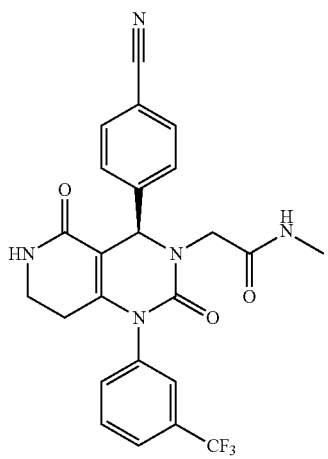 [SMILES: CNC(=O)CN1C(=O)N(c2cccc(C(F)(F)F)c2)C2=C(C(=O)NCC2)[C@H]1c1ccc(C#N)cc1]

(R)-2-(4-(4-Cyanophenyl)-2,5-dioxo-1-(3-(trifluoromethyl)phenyl)-1,2,5,6,7,8-hexahydropyrido[4,3-d]pyrimidin-3(4H)-yl)-N-methylacetamide Yield: 77 mg; ESI mass spectrum [M+H]$^+$=484; Retention time: 2.72 min (early eluting enantiomer) (I_IA_20_MeOH_DEA).

Example 12B

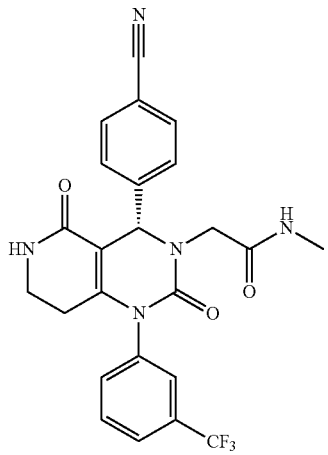 [SMILES: CNC(=O)CN1C(=O)N(c2cccc(C(F)(F)F)c2)C2=C(C(=O)NCC2)[C@@H]1c1ccc(C#N)cc1]

(S)-2-(4-(4-Cyanophenyl)-2,5-dioxo-1-(3-(trifluoromethyl)phenyl)-1,2,5,6,7,8-hexahydropyrido[4,3-d]pyrimidin-3(4H)-yl)-N-methylacetamide Yield: 70 mg; ESI mass spectrum [M+H]$^+$=484; Retention time: 4.00 min (late eluting enantiomer) (I_IA_20_MeOH_DEA).

Examples 12.1-12.9

The following examples of Table 1 are prepared in analogy to example 12, replacing methylamine with the appropriate amine as starting material.

TABLE 1

| Example | R³ | MS [M + H]⁺ | Retention time [min] | HPLC-Method |
|---|---|---|---|---|
| 12.1 | ![dimethylamide] | 498 | 0.78 | Z011_S03 |
| 12.2 | ![ethylamide] | 498 | 0.78 | Z011_S03 |
| 12.3 | ![hydroxyethylamide] | 514 | 0.72 | Z011_S03 |
| 12.4 | ![methoxyethylamide] | 528 | 0.76 | Z011_S03 |
| 12.5 | ![bicyclic pyrrolidine] | 536 | 0.83 | Z011_S03 |
| 12.6 | ![piperidine] | 538 | 0.85 | Z011_S03 |
| 12.7 | ![morpholine] | 540 | 0.78 | Z011_S03 |
| 12.8 | ![fluoropyrrolidine] | 542 | 0.80 | Z011_S03 |

TABLE 1-continued

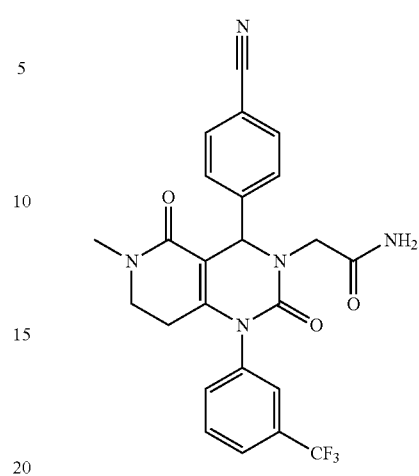

| Example | R³ | MS [M + H]⁺ | Retention time [min] | HPLC-Method |
|---|---|---|---|---|
| 12.9 | (1-methyl-pyrrolo[3,4-c]pyrazol-5-yl)carbonyl group | 576 | 0.78 | Z011_S03 |

Example 13

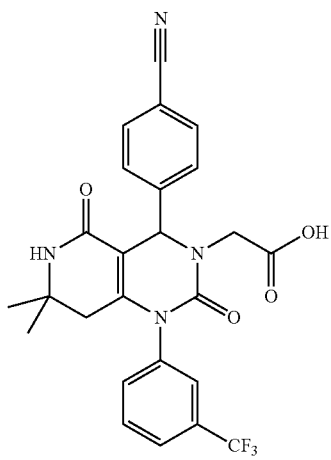 [SMILES: CC1(C)CC2=C(C(=O)N1)C(c1ccc(C#N)cc1)N(CC(=O)O)C(=O)N2c1cccc(C(F)(F)F)c1]

2-(4-(4-cyanophenyl)-7,7-dimethyl-2,5-dioxo-1-(3-(trifluoromethyl)phenyl)-1,2,5,6,7,8-hexahydro-pyrido[4,3-d]pyrimidin-3(4H)-yl)acetic acid The title compound is prepared in analogy to 2-(4-(4-cyanophenyl)-2,5-dioxo-1-(3-(trifluoromethyl)phenyl)-1,2,5,6,7,8-hexahydropyrido[4,3-d]pyrimidin-3(4H)-yl)acetic acid (example 10), using methyl 2-(4-(4-cyanophenyl)-7,7-dimethyl-2,5-dioxo-1-(3-(trifluoromethyl)phenyl)-1,2,5,6,7,8-hexahydropyrido[4,3-d]pyrimidin-3(4H)-yl)acetate (intermediate 13, 25 mg, 49 μmol) as starting material. Yield: 15 mg; ESI mass spectrum [M+H]⁺=499; Retention time HPLC: 0.74 min (V011_S01).

Example 14

2-(4-(4-Cyanophenyl)-6-methyl-2,5-dioxo-1-(3-(trifluoromethyl)phenyl)-1,2,5,6,7,8-hexahydropyrido[4,3-d]pyrimidin-3(4H)-yl)acetamide Triethylamine (38 μL, 0.27 mmol) is added to a solution of 2-(4-(4-cyanophenyl)-6-methyl-2,5-dioxo-1-(3-(trifluoromethyl)phenyl)-1,2,5,6,7,8-hexahydropyrido[4,3-d]pyrimidin-3(4H)-yl)acetic acid (intermediate 12, 44 mg, 91 μmol) in N,N-dimethylformamide (0.5 mL). After 10 min, O-(7-azabenzotriazol-1-yl)-N,N,N',N'-tetramethyluronium hexafluorophosphate (29 mg, 91 μmol) is added. After 15 min, ammonia (0.5 M in 1,4-dioxane, 1.8 mL, 0.91 mmol) is added and the mixture is stirred at room temperature for 2 h. Another portion of ammonia (0.5 M in 1,4-dioxane, 2.0 mL, 1.0 mmol) is added and the mixture is stirred for 3 h. Another portion of triethylamine (40 μL, 0.28 mmol) and ammonium chloride (15 mg, 0.28 mmol) and the mixture is stirred for 2 h, diluted with water (1 mL) and purified by preparative reversed-phase HPLC (Waters Xbridge™-C₁₈, gradient of acetonitrile in water, 0.1% NH₃). Yield: 22 mg; ESI mass spectrum [M+H]⁺=484; Retention time HPLC: 0.79 min (Z011_S03).

Example 15

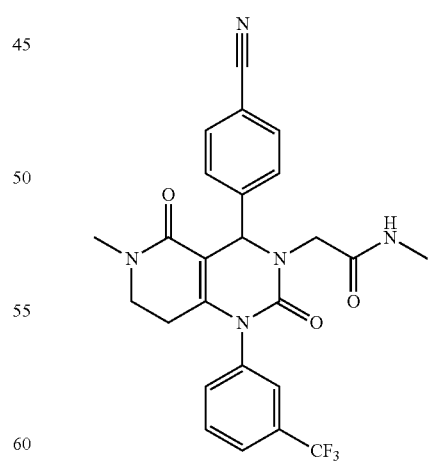

2-(4-(4-Cyanophenyl)-6-methyl-2,5-dioxo-1-(3-(trifluoromethyl)phenyl)-1,2,5,6,7,8-hexahydropyrido[4,3-d]pyrimidin-3(4H)-yl)-N-methylacetamide Triethylamine (38 μL, 0.27 mmol) is added to a solution of 2-(4-(4-cyanophenyl)-6-methyl-2,5-dioxo-1-(3-(trifluoromethyl)phenyl)-1,2,5,6,7,8-hexahydropyrido[4,3-d]pyrimidin-3(4H)-yl)acetic acid (intermediate 12, 44 mg, 91 μmol) in N,N-dimethylformamide (0.5 mL). After 10 min, O-(7-azabenzotriazol-1-yl)-N,N,N',N'-tetramethyluronium hexafluorophosphate (29 mg, 91 μmol) is added. After 15 min, methylamine (2 M in tetrahydrofuran, 450 μL, 0.90 mmol) is added and the mixture is stirred at room temperature for 2 h. The mixture is diluted with water (0.5 mL) and purified by preparative reversed-phase HPLC (Waters Xbridge™-C$_{18}$, gradient of acetonitrile in water, 0.1% NH$_3$). Yield: 33 mg; ESI mass spectrum [M+H]$^+$=498; Retention time HPLC: 0.79 min (Z011_S03).

Examples 15.1-15.6

The following examples of Table 2 are prepared in analogy to example 15, replacing methylamine with the appropriate amine as starting material.

TABLE 2

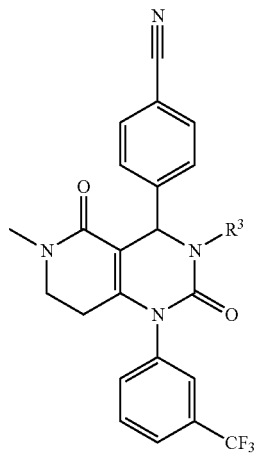

| Example | R$^3$ | MS [M + H]$^+$ | Retention time [min] | HPLC-Method |
|---|---|---|---|---|
| 15.1 | | 512 | 0.83 | Z011_S03 |
| 15.2 | | 528 | 0.77 | Z011_S03 |
| 15.3 | | 566 | 0.92 | Z011_S03 |
| 15.4 | | 574 | 0.76 | Z011_S03 |
| 15.5 | | 582 | 0.86 | Z011_S03 |
| 15.6 | | 602 | 0.81 | Z011_S03 |

Example 16

4-(4-Cyanophenyl)-N-methyl-2,5-dioxo-1-(3-(trifluoromethyl)phenyl)-1,2,5,6,7,8-hexahydropyrido[4,3-d]pyrimidine-3(4H)-carboxamide A mixture of 4-nitrophenyl 4-(4-cyanophenyl)-2,5-dioxo-1-[3-(trifluoromethyl)phenyl]-1H,2H,3H,4H,5H,6H,7H, 8H-pyrido[4,3-d]pyrimidine-3-carboxylate (intermediate 14, 25 mg, 43 μmol) in acetonitrile (2 mL) is treated with methylamine (2 M in tetrahydrofuran, 65 μL, 130 μmol) and stirred at room temperature for 20 min. The mixture is purified by preparative reversed-phase HPLC (Agilent ZORBAX™ SB-C$_{18}$, gradient of acetonitrile in water, 0.15% formic acid). Yield: 5 mg, ESI mass spectrum [M+H]$^+$=470; Retention time HPLC: 0.98 min (Z017_504).

Examples 17 and 18

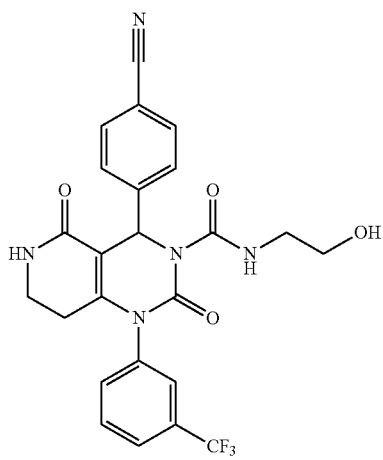 [SMILES: N#Cc1ccc(C2C3=C(CCNC3=O)N(c3cccc(C(F)(F)F)c3)C(=O)N2C(=O)NCCO)cc1]

and

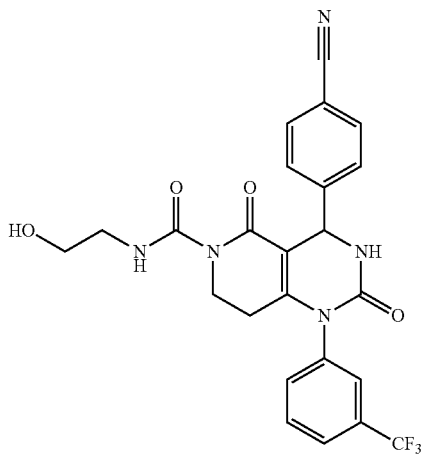 [SMILES: N#Cc1ccc(C2NC(=O)N(c3cccc(C(F)(F)F)c3)C3=C2C(=O)N(C(=O)NCCO)CC3)cc1]

A mixture of 4-nitrophenyl 4-(4-cyanophenyl)-2,5-dioxo-1-[3-(trifluoromethyl)phenyl]-1H,2H,3H,4H,5H,6H,7H,8H-pyrido[4,3-d]pyrimidine-3-carboxylate (intermediate 14, 38 mg, 66 μmol) in acetonitrile (2 mL) is treated with ethanolamine (12 μL, 0.20 mmol) and stirred at room temperature for 20 min. The mixture is purified by preparative reversed-phase HPLC (Agilent ZORBAX™ SB-C$_{18}$, gradient of acetonitrile in water, 0.15% formic acid).

Example 17

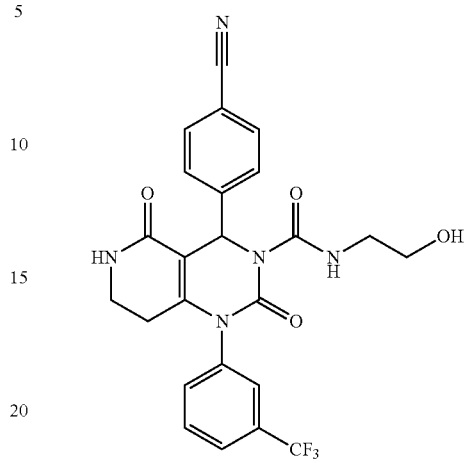

4-(4-Cyanophenyl)-N-(2-hydroxyethyl)-2,5-dioxo-1-[3-(trifluoromethyl)phenyl]-1H,2H,3H,4H,5H,6H,7H,8H-pyrido[4,3-d]pyrimidine-3-carboxamide Yield: 7 mg, ESI mass spectrum [M+H]$^+$=500; Retention time HPLC: 0.79 min (Z011_503).

Example 18

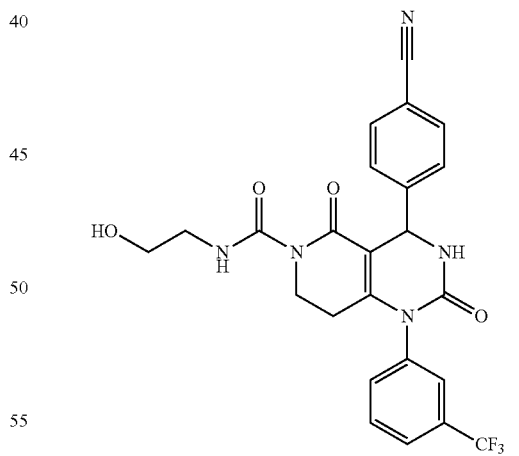

4-(4-Cyanophenyl)-N-(2-hydroxyethyl)-2,5-dioxo-1-[3-(trifluoromethyl)phenyl]-1H,2H,3H,4H,5H,6H,7H,8H-pyrido[4,3-d]pyrimidine-6-carboxamide Yield: 15 mg, ESI mass spectrum [M+H]$^+$=500; Retention time HPLC: 0.78 min (Z011_503).

Example 19

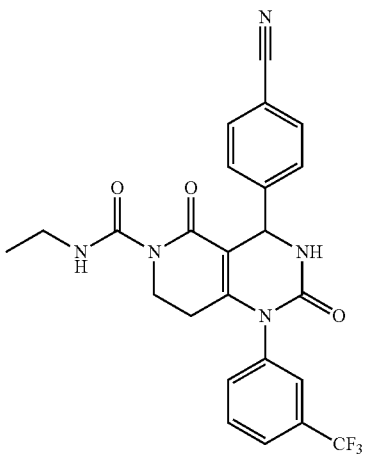 [SMILES: CCNC(=O)N1CCC2=C(C1=O)C(c1ccc(C#N)cc1)NC(=O)N2c1cccc(C(F)(F)F)c1]

4-(4-Cyanophenyl)-N-ethyl-2,5-dioxo-1-[3-(trifluoromethyl)phenyl]-1H,2H,3H,4H,5H,6H,7H,8H-pyrido[4,3-d]pyrimidine-6-carboxamide A mixture of 4-nitrophenyl 4-(4-cyanophenyl)-2,5-dioxo-1-[3-(trifluoromethyl)phenyl]-1H,2H,3H,4H,5H,6H,7H, 8H-pyrido[4,3-d]pyrimidine-3-carboxylate (intermediate 14, 19 mg, 33 μmol) in acetonitrile (2 mL) is treated with ethylamine (2 M in tetrahydrofuran, 50 μL, 0.10 mmol) and stirred at room temperature for 20 min. The mixture is purified by preparative reversed-phase HPLC (Agilent ZORBAX™ SB-C$_{18}$, gradient of acetonitrile in water, 0.15% formic acid). Yield: 4 mg, ESI mass spectrum [M+H]$^+$=484; Retention time HPLC: 0.99 min (Z017_504).

Example 20

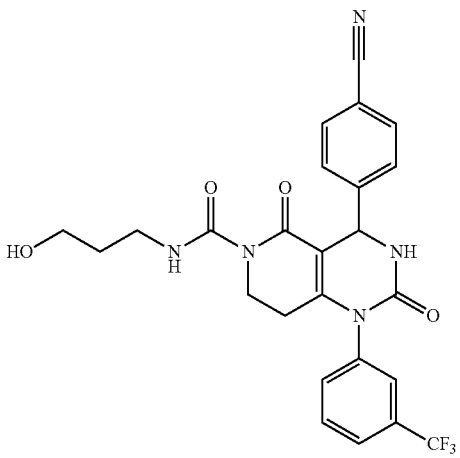 [SMILES: N#Cc1ccc(C2NC(=O)N(c3cccc(C(F)(F)F)c3)C3=C2C(=O)N(C(=O)NCCCO)CC3)cc1]

4-(4-Cyanophenyl)-N-(3-hydroxypropyl)-2,5-dioxo-1-[3-(trifluoromethyl)phenyl]-1H,2H,3H,4H,5H,6H, 7H,8H-pyrido[4,3-d]pyrimidine-6-carboxamide A mixture of 4-nitrophenyl 4-(4-cyanophenyl)-2,5-dioxo-1-[3-(trifluoromethyl)phenyl]-1H,2H,3H,4H,5H,6H,7H, 8H-pyrido[4,3-d]pyrimidine-3-carboxylate (intermediate 14, 38 mg, 66 μmol) in acetonitrile (2 mL) is treated with 3-amino-1-propanol (15 mg, 0.20 mmol) and stirred at room temperature for 20 min. The mixture is purified by preparative reversed-phase HPLC (Agilent ZORBAX™ SB-C$_{18}$, gradient of acetonitrile in water, 0.15% formic acid). Yield: 7 mg, ESI mass spectrum [M+H]$^+$=514; Retention time HPLC: 0.79 min (Z011_S03).

Example 21

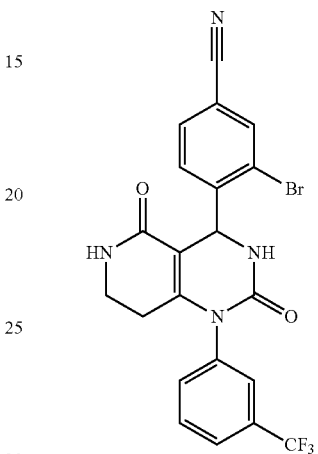

3-Bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile

Step 1

Tert-butyl 5-[(2-Bromo-4-cyanophenyl)({[(tert-butoxy)carbonyl]amino})methyl]-6-oxo-4-{[3-(trifluoromethyl)phenyl]amino}-1,2,3,6-tetrahydropyridine-1-carboxylate Sodium hydride (60% in mineral oil, 212 mg, 5.32 mmol) is added to a mixture of tert-butyl 2-oxo-4-(3-(trifluoromethyl)phenylamino)-5,6-dihydropyridine-1(2H)-carboxylate (intermediate 3, 1.90 g, 5.32 mmol) and methyltetrahydrofuran (5.0 mL), and the mixture is stirred at room temperature for 10 min Tert-butyl N-[(benzenesulfonyl)(2-bromo-4-cyanophenyl)methyl]carbamate (intermediate 15, 2.00 g, 4.43 mmol) is added, and the mixture is stirred at room temperature for 2 h. Ethyl acetate (50 mL) is added, and the mixture is extracted twice with water. The organic layer is concentrated under reduced pressure. Yield: 3.40 g (3.83 mmol based on 75% purity). ESI mass spectrum: [($^{79}$Br)-M+H]$^+$=665, [($^{81}$Br)-M+H]$^+$=667; Retention time HPLC: 1.25 min (Z017_504).

Step 2

4-[Amino(2-oxo-4-{[3-(trifluoromethyl)phenyl]amino}-1,2,5,6-tetrahydropyridin-3-yl)methyl]-3-bromobenzonitrile hydrochloride A solution of hydrogen chloride in 1,4-dioxane (4 M, 4.0 mL, 16.0 mmol) is added to a mixture of tert-butyl 5-[(2-bromo-4-cyanophenyl)({[(tert-butoxy)carbonyl]amino})-methyl]-6-oxo-4-{[3-(trifluoromethyl)phenyl]amino}-1,2,3,6-tetrahydropyridine-1-carboxylate (step 1, 3.40 g, 3.82 mmol based on 75% purity) and acetonitrile (8 mL), and the mixture is stirred at room temperature over night. The precipitate is filtered, washed with acetonitrile and dried. Yield: 1.88 g (3.14 mmol based on 90% purity). ESI mass spectrum: [($^{79}$Br)-M+H]$^+$=465, [($^{81}$Br)-M+H]$^+$=467; Retention time HPLC: 0.90 min (Z017_504).

Step 3

3-Bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile Triethylamine (265 μL, 1.89 mmol) is added to a mixture of 4-[amino(2-oxo-4-{[3-(trifluoromethyl)phenyl]amino}-1,2,5,6-tetrahydropyridin-3-yl)methyl]-3-bromobenzonitrile hydrochloride (step 2, 1.88 g, 3.14 mmol based on 90% purity) and acetonitrile (5.0 mL). 1,1'-Carbonyldiimidazole (612 mg, 3.77 mmol) is added, and the mixture is stirred at room temperature for 2 h. All volatiles are removed under reduced pressure, and the residue is treated with water. The precipitate is filtered and digested with a mixture of N,N-dimethylformamide, methanol and acetic acid. The mixture is filtered, and the precipitate is dried.

Yield: 764 mg. ESI mass spectrum: [($^{79}$Br)-M+H]$^+$=491, [($^{81}$Br)-M+H]$^+$=493; Retention time HPLC: 0.93 min (Z017_504).

Example 22

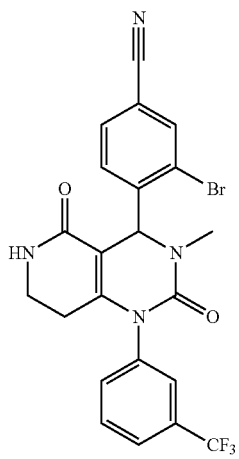 [SMILES: CN1C(=O)N(c2cccc(C(F)(F)F)c2)C2=C(C(=O)NCC2)C1c1ccc(C#N)cc1Br]

3-Bromo-4-{3-methyl-2,5-dioxo-1-[3-(trifluoromethyl)phenyl]-1H,2H,3H,4H,5H,6H,7H,8H-pyrido[4,3-d]pyrimidin-4-yl}benzonitrile Methyl iodide (220 μL, 3.54 mmol) is added to a mixture of 3-bromo-4-{2,5-dioxo-1-[3-(trifluoromethyl)phenyl]-1H,2H,3H,4H,5H,6H,7H,8H-pyrido[4,3-d]pyrimidin-4-yl}-benzonitrile (example 21, 580 mg, 1.18 mmol) and cesium carbonate (769 mg, 2.36 mmol) in N,N-dimethylformamide (6.0 mL), and the mixture is stirred at room temperature for 2 h. Another portion of methyl iodide (220 μL, 3.54 mmol) is added, and the mixture is stirred for 2 h, diluted with methanol and purified by preparative reversed-phase HPLC (Agilent ZORBAX™ SB-C$_{18}$, gradient of acetonitrile in water, 0.1% TFA). Yield: 214 mg; ESI mass spectrum: [($^{79}$Br)-M+H]$^+$=505, [($^{81}$Br)-M+H]$^+$=507; Retention time HPLC: 0.98 min (Z017_S04).

Example 23

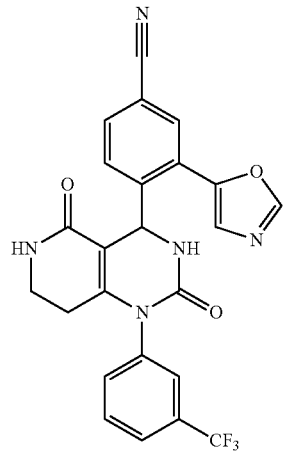 [SMILES: N#Cc1ccc(C2NC(=O)N(c3cccc(C(F)(F)F)c3)C3=C2C(=O)NCC3)c(-c2cnco2)c1]

4-{2,5-Dioxo-1-[3-(trifluoromethyl)phenyl]-1H,2H,3H,4H,5H,6H,7H,8H-pyrido-[4,3-d]pyrimidin-4-yl}-3-(1,3-oxazol-5-yl)benzonitrile Under an atmosphere of nitrogen, cesium carbonate (2 M in water, 142 μL, 284 μmol) is added to a mixture of 3-bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile (example 21, 70 mg, 0.14 mmol), 5-(tetramethyl-1,3,2-dioxaborolan-2-yl)-2-[tris(propan-2-yl)silyl]-1,3-oxazole (151 mg, 0.21 mmol) and [1,1'-bis(diphenylphosphino)ferrocene]dichloropalladium(II) (1:1 complex with dichloromethane, 12 mg, 15 μmol) in dioxane (1.0 mL). The mixture is heated at 80° C. for 2 h, cooled to room temperature, diluted with acetonitrile (1 mL), acidified with trifluoroacetic acid (0.5 mL), and purified by preparative reversed-phase HPLC (Agilent ZORBAX™ Bonus-RP, gradient of acetonitrile in water, 0.15% trifluoroacetic acid). Yield: 30 mg, ESI mass spectrum [M+H]$^+$=480; Retention time HPLC: 0.91 min (Z017_S04).

Example 24

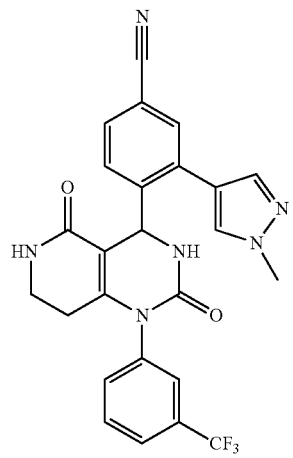 [SMILES: Cn1cc(-c2cc(C#N)ccc2C2NC(=O)N(c3cccc(C(F)(F)F)c3)C3=C2C(=O)NCC3)cn1]

4-{2,5-Dioxo-1-[3-(trifluoromethyl)phenyl]-1H,2H,3H,4H,5H,6H,7H,8H-pyrido-[4,3-d]pyrimidin-4-yl}-3-(1-methyl-1H-pyrazol-4-yl)benzonitrile Under an atmosphere of nitrogen, potassium carbonate (2 M in water, 150 μL, 0.30 mmol) is added to a mixture of 3-bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile (example 21, 70 mg, 0.14 mmol), 1-methyl-4-(tetramethyl-1,3,2-dioxaborolan-2-yl)-1H-pyrazole (44 mg, 0.21 mmol) and [1,1'-bis(diphenylphosphino)ferrocene]dichloropalladium(II) (1:1 complex with dichloromethane, 12 mg, 15 µmol) in N,N-dimethylformamide (1.0 mL). The mixture is heated at 80° C. for 1.5 h, cooled to room temperature, diluted with acetonitrile (1 mL), acidified with acetic acid (0.1 mL), and purified by preparative reversed-phase HPLC (Agilent ZORBAX™ Bonus-RP, gradient of acetonitrile in water, 0.15% trifluoroacetic acid). Yield: 37 mg, ESI mass spectrum [M+H]⁺=493; Retention time HPLC: 0.91 min (Z017_504).

Example 25

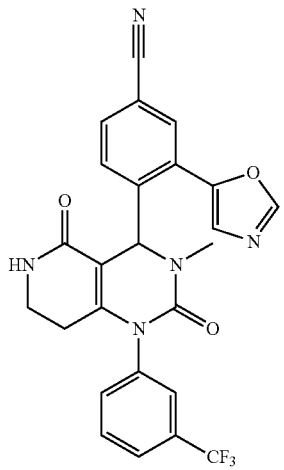 [SMILES: CN1C(=O)N(c2cccc(C(F)(F)F)c2)C2=C(C(=O)NCC2)C1c1ccc(C#N)cc1-c1cnco1]

4-{3-Methyl-2,5-dioxo-1-[3-(trifluoromethyl)phenyl]-1H,2H,3H,4H,5H,6H,7H,8H-pyrido[4,3-d]pyrimidin-4-yl}-3-(1,3-oxazol-5-yl)benzonitrile Under an atmosphere of nitrogen, cesium carbonate (2 M in water, 139 µL, 277 µmol) is added to a mixture of 3-bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile (example 22, 70 mg, 0.14 mmol), 5-(tetramethyl-1,3,2-dioxaborolan-2-yl)-2-[tris(propan-2-yl)silyl]-1,3-oxazole (146 mg, 0.21 mmol) and [1,1'-bis(diphenylphosphino)ferrocene]dichloropalladium(II) (1:1 complex with dichloromethane, 11 mg, 14 µmol) in dioxane (1.0 mL), and the mixture is heated at 80° C. for 4 h. Another portion of 5-(tetramethyl-1,3,2-dioxaborolan-2-yl)-2-[tris(propan-2-yl)silyl]-1,3-oxazole (100 mg, 0.14 mmol) is added, and the mixture is stirred at 80° C. over night. The mixture is cooled at room temperature, diluted with acetonitrile (1.0 mL), acidified with trifluoroacetic acid (0.5 mL), and purified by preparative reversed-phase HPLC (Agilent ZORBAX™ Bonus-RP, gradient of acetonitrile in water, 0.15% trifluoroacetic acid). Yield: 30 mg, ESI mass spectrum [M+H]⁺=494; Retention time HPLC: 0.96 min (Z017_504).

Example 26

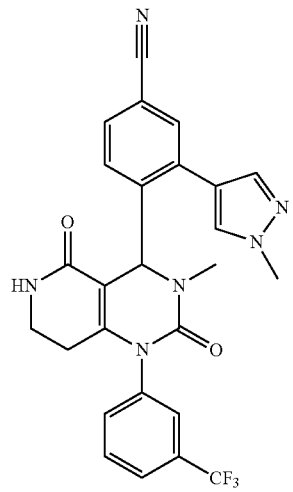 [SMILES: CN1C(=O)N(c2cccc(C(F)(F)F)c2)C2=C(C(=O)NCC2)C1c1ccc(C#N)cc1-c1cnn(C)c1]

3-(1-Methyl-1H-pyrazol-4-yl)-4-{3-methyl-2,5-dioxo-1-[3-(trifluoromethyl)phenyl]-1H,2H,3H,4H,5H,6H,7H,8H-pyrido[4,3-d]pyrimidin-4-yl}benzonitrile Under an atmosphere of nitrogen, potassium carbonate (2 M in water, 145 µL, 0.29 mmol) is added to a mixture of 3-bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile (example 022, 70 mg, 0.14 mmol), 1-methyl-4-(tetramethyl-1,3,2-dioxaborolan-2-yl)-1H-pyrazole (43 mg, 0.21 mmol) and [1,1'-bis(diphenylphosphino)ferrocene]dichloropalladium(II) (1:1 complex with dichloromethane, 11 mg, 14 µmol) in N,N-dimethylformamide (1.0 mL). The mixture is heated at 80° C. for 1.5 h, cooled at room temperature and purified by preparative reversed-phase HPLC (Waters SunFire™-C₁₈, gradient of acetonitrile in water, 0.1% trifluoroacetic acid). Yield: 30 mg, ESI mass spectrum [M+H]⁺=507; Retention time HPLC: 0.73 min (005_CA01).

Example 27

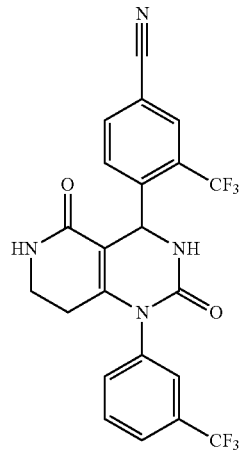 [SMILES: N#Cc1ccc(C2NC(=O)N(c3cccc(C(F)(F)F)c3)C3=C2C(=O)NCC3)c(C(F)(F)F)c1]

4-{2,5-Dioxo-1-[3-(trifluoromethyl)phenyl]-1H,2H,3H,4H,5H,6H,7H,8H-pyrido-[4,3-d]pyrimidin-4-yl}-3-(trifluoromethyl)benzonitrile The title compound is prepared in analogy to 3-bromo-4-{2,5-dioxo-1-[3-(trifluoromethyl)-phenyl]-1H,2H,3H,4H, 5H,6H,7H,8H-pyrido[4,3-d]pyrimidin-4-yl}benzonitrile (example 21), substituting tert-butyl N-[(benzenesulfonyl)(2-bromo-4-cyanophenyl)methyl]-carbamate (intermediate 15) with tert-butyl N-[(benzenesulfonyl)-[4-cyano-2-(trifluoromethyl)phenyl]methyl]carbamate (intermediate 16, 900 mg) as starting material in step 1.

Yield: 33 mg. ESI mass spectrum [M+H]$^+$=481; Retention time HPLC: 0.94 min (Z017_S04).

Example 28

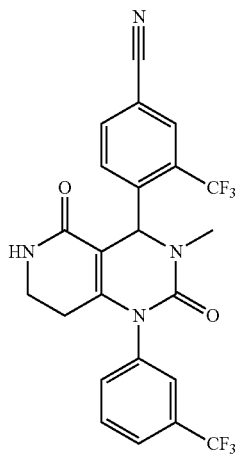 [SMILES: CN1C(=O)N(c2cccc(C(F)(F)F)c2)C2=C(C(=O)NCC2)C1c1ccc(C#N)cc1C(F)(F)F]

4-{3-Methyl-2,5-dioxo-1-[3-(trifluoromethyl)phenyl]-1H,2H,3H,4H,5H,6H,7H,8H-pyrido[4,3-d]pyrimidin-4-yl}-3-(trifluoromethyl)benzonitrile Cesium carbonate (109 mg, 0.33 mmol) is added to a solution of 4-{2,5-Dioxo-1-[3-(trifluoromethyl)phenyl]-1H, 2H,3H,4H,5H,6H,7H,8H-pyrido-[4,3-d]pyrimidin-4-yl}-3-(trifluoromethyl)benzonitrile (example 27, 80 mg, 0.17 mmol) in N,N-dimethylformamide (1 mL). Methyl iodide (31 µL, 0.50 mmol) is added, and the mixture is stirred at room temperature for 2 h, diluted with acetonitrile and purified by preparative reversed-phase HPLC (Waters SunFire™-C$_{18}$, gradient of acetonitrile in water, 0.1% trifluoroacetic acid).

Yield: 31 mg, ESI mass spectrum [M+H]$^+$=495; Retention time HPLC: 0.87 min (005_CA07).

Example 29

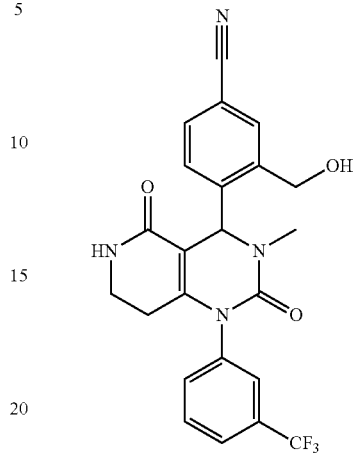

3-(Hydroxymethyl)-4-{3-methyl-2,5-dioxo-1-[3-(trifluoromethyl)phenyl]-1H,2H,3H,4H,5H,6H,7H,8H-pyrido[4,3-d]pyrimidin-4-yl}benzonitrile 1,1'-Carbonyldiimidazole (8.3 mg, 51 µmol) is added to a mixture of 5-cyano-2-{3-methyl-2,5-dioxo-1-[3-(trifluoromethyl)phenyl]-1H,2H,3H,4H,5H,6H,7H,8H-pyrido[4,3-d]-pyrimidin-4-yl}benzoic acid (intermediate 18) 22 mg, 47 µmol) in tetrahydrofuran (1.0 mL). The mixture is stirred at room temperature for 1.5 h and cooled in an ice bath at 5° C. A solution of sodium borohydride (2.6 mg, 70 µmol) in water (0.5 mL) is added dropwise while the temperature is kept below 8° C. The mixture is stirred for 1 h while the temperature is kept below 5° C. Aqueous hydrogen chloride (1 M) is added while the temperature is kept between 5-10° C. The mixture is warmed at room temperature, diluted with water and purified by preparative reversed-phase HPLC (Agilent ZORBAX™ SB-C$_{18}$, gradient of acetonitrile in water, 0.15% trifluoroacetic acid). Yield: 6 mg, ESI mass spectrum [M+H]$^+$=457; Retention time HPLC: 0.93 min (Z017_504).

Examples 30A and 30B

Enantiomers of Example 25

The enantiomers of racemic 4-{3-methyl-2,5-dioxo-1-[3-(trifluoromethyl)phenyl]-1H,2H,3H,4H,5H,6H,7H,8H-pyrido[4,3-d]pyrimidin-4-yl}-3-(1,3-oxazol-5-yl)benzonitrile (example 25, 212 mg, 0.43 mmol) are separated by preparative supercritical fluid chromatography on a chiral phase (Daicel Chiralpak IA, 2×20×250 mm, 5 µm, 20% i-PrOH+20 mM NH$_3$ in supercritical CO$_2$, 40° C., 150 bar back pressure).

Example 30A

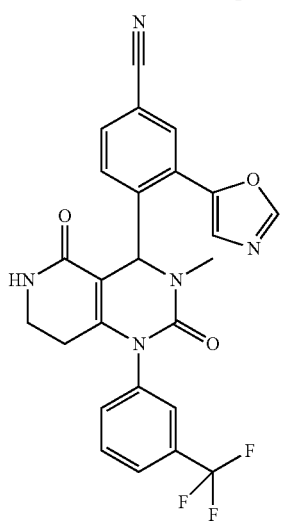

4-[(4R)-3-Methyl-2,5-dioxo-1-[3-(trifluoromethyl)phenyl]-1H,2H,3H,4H,5H,6H,7H,8H-pyrido[4,3-d]pyrimidin-4-yl]-3-(1,3-oxazol-5-yl)-benzonitrile Yield: 64 mg; ESI mass spectrum [M+H]$^+$=494; Retention time: 2.70 min (early eluting enantiomer) (I_IA_20_IPA_NH3).

Example 30B

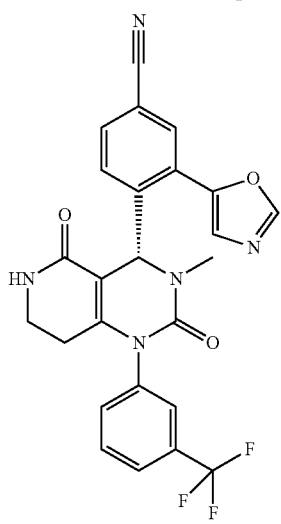 [SMILES: CN1C(=O)N(c2cccc(C(F)(F)F)c2)C2=C(C(=O)NCC2)[C@@H]1c1ccc(C#N)cc1-c1cnco1]

4-[(4S)-3-Methyl-2,5-dioxo-1-[3-(trifluoromethyl)phenyl]-1H,2H,3H,4H,5H,6H,7H,8H-pyrido[4,3-d]pyrimidin-4-yl]-3-(1,3-oxazol-5-yl)benzonitrile Yield: 50 mg; ESI mass spectrum [M+H]$^+$=494; Retention time: 3.56 min (late eluting enantiomer) (I_IA_20_IPA_NH3).

Examples 31A and 31B

Enantiomers of Example 26

The enantiomers of racemic 3-(1-methyl-1H-pyrazol-4-yl)-4-{3-methyl-2,5-dioxo-1-[3-(trifluoromethyl)phenyl]-1H,2H,3H,4H,5H,6H,7H,8H-pyrido[4,3-d]pyrimidin-4-yl}-benzonitrile (example 26, 1.18 g, 2.33 mmol) are separated by preparative supercritical fluid chromatography on a chiral phase (Daicel Chiralpak IA, 20×250 mm, 5 µm, 20% i-PrOH in supercritical CO$_2$, 40° C., 150 bar back pressure).

Example 31A

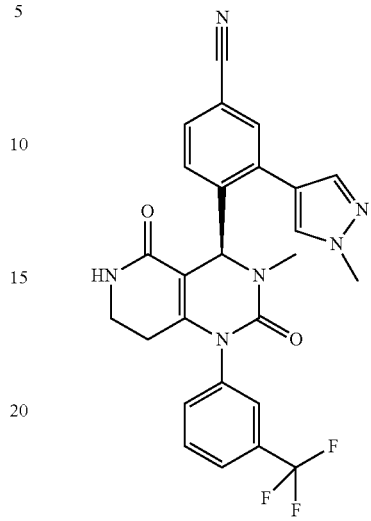

3-(1-Methyl-1H-pyrazol-4-yl)-4-[(4R)-3-methyl-2,5-dioxo-1-[3-(trifluoromethyl)-phenyl]-1H,2H,3H,4H,5H,6H,7H,8H-pyrido[4,3-d]pyrimidin-4-yl]benzonitrile Yield: 409 mg; ESI mass spectrum [M+H]$^+$=507; Retention time: 2.79 min (early eluting enantiomer) (I_IA_20_IPA_NH3).

Example 31B

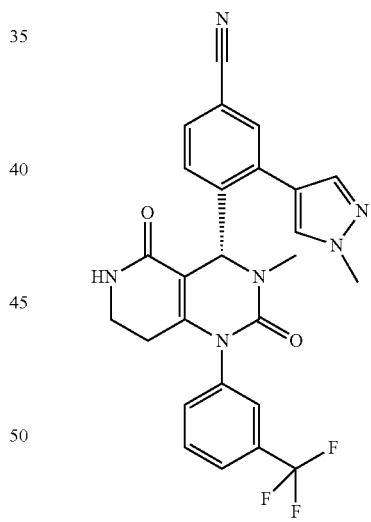

3-(1-Methyl-1H-pyrazol-4-yl)-4-[(4S)-3-methyl-2,5-dioxo-1-[3-(trifluoromethyl)-phenyl]-1H,2H,3H,4H,5H,6H,7H,8H-pyrido[4,3-d]pyrimidin-4-yl]benzonitrile Yield: 391 mg; ESI mass spectrum [M+H]$^+$=507; Retention time: 3.77 min (late eluting enantiomer) (I_IA_20_IPA_NH3).

Examples 32A and 32B: Enantiomers of Example 29

The enantiomers of racemic 3-(hydroxymethyl)-4-{3-methyl-2,5-dioxo-1-[3-(trifluoromethyl)phenyl]-1H,2H,3H, 4H,5H,6H,7H,8H-pyrido[4,3-d]pyrimidin-4-yl}benzonitrile (example 29, 163 mg, 0.36 mmol) are separated by preparative supercritical fluid chromatography on a chiral phase (Daicel Chiralpak IC, 2×10×250 mm, 5 μm, 20% EtOH in supercritical $CO_2$, 40° C., 120 bar back pressure).

Example 32A

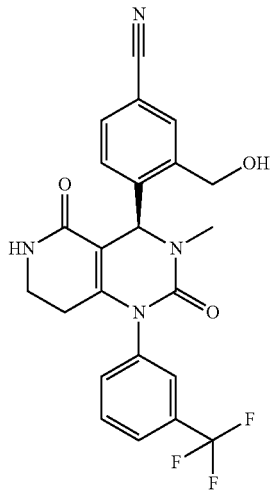 [SMILES: CN1C(=O)N(c2cccc(C(F)(F)F)c2)C2=C(C(=O)NCC2)[C@H]1c1ccc(C#N)cc1CO]

3-(Hydroxymethyl)-4-[(4R)-3-methyl-2,5-dioxo-1-[3-(trifluoromethyl)phenyl]-1H,2H,3H,4H,5H,6H,7H,8H-pyrido[4,3-d]pyrimidin-4-yl]benzonitrile Yield: 54 mg; ESI mass spectrum [M+H]$^+$=457; Retention time: 4.13 min (early eluting enantiomer) (I_IC_30_ETOH_NH3).

Example 32B

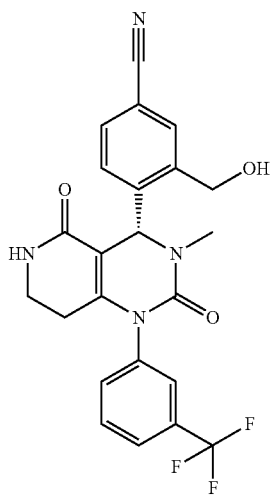 [SMILES: CN1C(=O)N(c2cccc(C(F)(F)F)c2)C2=C(C(=O)NCC2)[C@@H]1c1ccc(C#N)cc1CO]

3-(Hydroxymethyl)-4-[(4S)-3-methyl-2,5-dioxo-1-[3-(trifluoromethyl)phenyl]-1H,2H,3H,4H,5H,6H,7H,8H-pyrido[4,3-d]pyrimidin-4-yl]benzonitrile Yield: 52 mg; ESI mass spectrum [M+H]$^+$=457; Retention time: 4.80 min (late eluting enantiomer) (I_IC_30_ETOH_NH3).

Example 33

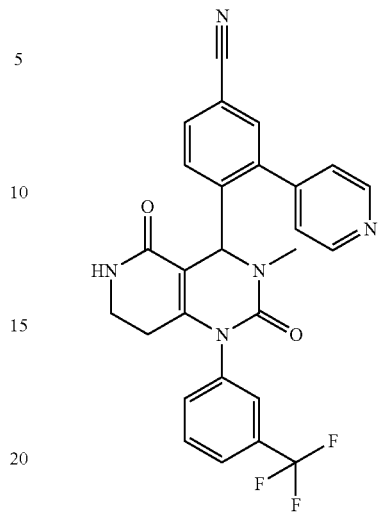

4-{3-Methyl-2,5-dioxo-1-[3-(trifluoromethyl)phenyl]-1H,2H,3H,4H,5H,6H,7H,8H-pyrido[4,3-d]pyrimidin-4-yl}-3-(pyridin-4-yl)benzonitrile Under an atmosphere of nitrogen, potassium carbonate (2 M in water, 104 μL, 0.21 mmol) is added to a mixture of 3-bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile (example 22, 50 mg, 0.10 mmol), 4-pyridylboronic acid (13 mg, 0.11 mmol) and [1,1'-bis(diphenylphosphino)ferrocene]dichloropalladium(II) (1:1 complex with dichloromethane, 8 mg, 10 μmol) in acetonitrile (1.0 mL). The mixture is heated at 80° C. for 3 h, cooled at room temperature, filtered through a thiol cartridge (Agilent PL-Thiol MP SPE) and purified by preparative reversed-phase HPLC (Waters Xbridge™-$C_{18}$, gradient of acetonitrile in water, 0.1% $NH_3$). Yield: 8 mg; ESI mass spectrum [M+H]$^+$=504; Retention time HPLC: 0.82 min (Z018_504).

Example 34

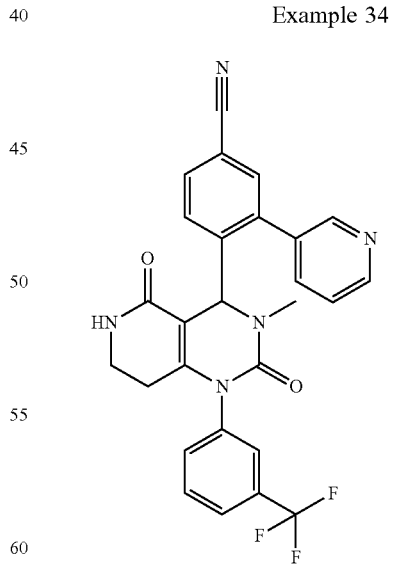

4-{3-Methyl-2,5-dioxo-1-[3-(trifluoromethyl)phenyl]-1H,2H,3H,4H,5H,6H,7H,8H-pyrido[4,3-d]pyrimidin-4-yl}-3-(pyridin-3-yl)benzonitrile Under an atmosphere of nitrogen, potassium carbonate (2 M in water, 415 μL, 0.83 mmol) is added to a mixture of 3-bromo-4-{2,5-dioxo-1-[3-(trifluoromethyl)phenyl]-1H,2H,3H,4H,5H,6H,7H,8H-pyrido[4,3-d]pyrimidin-4-yl}benzonitrile (example 22, 200 mg, 0.40 mmol), 3-pyridylboronic acid (54 mg, 0.44 mmol) and [1,1'-bis(diphenylphosphino)ferrocene]dichloropalladium(II) (1:1 complex with dichloromethane, 32 mg, 40 µmol) in acetonitrile (2.0 mL). The mixture is heated at 80° C. for 3 h, cooled at room temperature, filtered through a thiol cartridge (Agilent PL-Thiol MP SPE) and purified by preparative reversed-phase HPLC (Agilent ZORBAX™ SB-$C_{18}$, gradient of acetonitrile in water, 0.15% trifluoroacetic acid). Yield: 111 mg; ESI mass spectrum [M+H]$^+$=504; Retention time HPLC: 0.85 min (Z017_504).

Example 35

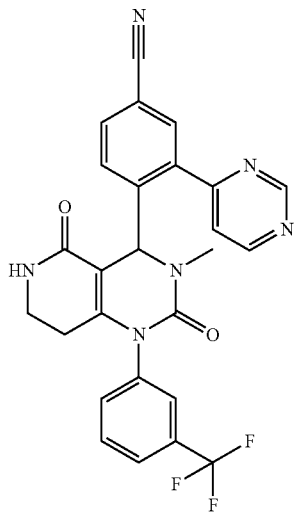 [SMILES: CN1C(=O)N(c2cccc(C(F)(F)F)c2)C2=C(C(=O)NCC2)C1c1ccc(C#N)cc1-c1ccncn1]

4-{3-Methyl-2,5-dioxo-1-[3-(trifluoromethyl)phenyl]-1H,2H,3H,4H,5H,6H,7H,8H-pyrido[4,3-d]pyrimidin-4-yl}-3-(pyrimidin-4-yl)benzonitrile Step 1

(5-Cyano-2-{3-methyl-2,5-dioxo-1-[3-(trifluoromethyl)phenyl]-1H,2H,3H,4H,5H,6H,7H,8H-pyrido[4,3-d]pyrimidin-4-yl}phenyl)boronic acid Under an atmosphere of nitrogen, potassium acetate (194 mg, 1.98 mmol) and 1,1'-bis-(diphenylphosphino)ferrocene]dichloropalladium(II) (1:1 complex with dichloromethane, 81 mg, 100 µmol) is added to a mixture of 3-bromo-4-{2,5-dioxo-1-[3-(trifluoromethyl)-phenyl]-1H,2H,3H,4H,5H,6H,7H,8H-pyrido[4,3-d]pyrimidin-4-yl}benzonitrile (example 22, 500 mg, 0.99 mmol) and bis(pinacolato)diboron (277 mg, 1.10 mmol) in dry dimethylsulfoxide (5.0 mL). The mixture is heated at 70° C. for 3 h, cooled at room temperature, diluted with dichloromethane and filtered through a thiol cartridge (Agilent PL-Thiol MP SPE). The filtrate is extracted with water and the filtrate is concentrated under reduced pressure. Yield 622 mg (70% purity); ESI mass spectrum [M+H]$^+$=471; Retention time HPLC: 0.90 min (Z017_504).

Step 2

4-{3-Methyl-2,5-dioxo-1-[3-(trifluoromethyl)phenyl]-1H,2H,3H,4H,5H,6H,7H,8H-pyrido[4,3-d]pyrimidin-4-yl}-3-(pyrimidin-4-yl)benzonitrile Under an atmosphere of nitrogen, potassium carbonate (2 M in water, 510 µL, 1.01 mmol) is added to a mixture of (5-cyano-2-{3-methyl-2,5-dioxo-1-[3-(trifluoromethyl)phenyl]-1H,2H,3H,4H,5H,6H,7H,8H-pyrido[4,3-d]pyrimidin-4-yl}phenyl)boronic acid (step 1, 238 mg, 0.36 mmol based on 70% purity) and 4-bromopyridine hydrochloride (108 mg, 0.56 mmol) in acetonitrile (2.0 mL). The mixture is heated at 80° C. over night, cooled at room temperature and purified by preparative reversed-phase HPLC (Agilent ZORBAX™ SB-$C_{18}$, gradient of acetonitrile in water, 0.1% formic acid). Yield: 7 mg; ESI mass spectrum [M+H]$^+$=505; Retention time HPLC: 0.94 min (Z017_S04).

Example 36

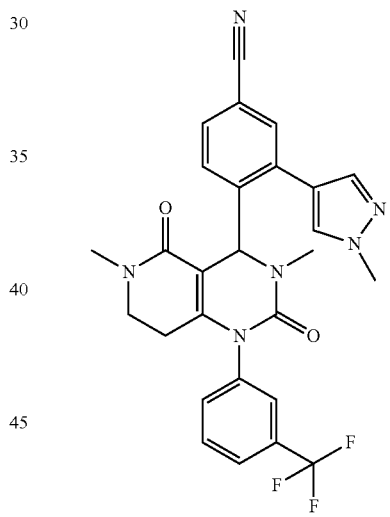

4-{3,6-Dimethyl-2,5-dioxo-1-[3-(trifluoromethyl) phenyl]4H,2H,3H,4H,5H,6H,7H,8H-pyrido[4,3-d]pyrimidin-4-yl}-3-(1-methyl-1H-pyrazol-4-yl)benzonitrile A mixture of 3-bromo-4-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzonitrile (intermediate 21, 35 mg, 67 µmol), 1-methyl-4-(tetramethyl-1,3,2-dioxaborolan-2-yl)-1H-pyrazole (15.9 mg, 74 µmol), aqueous potassium carbonate (2 M, 71 µL, 142 µmol) and [1,1'-bis(diphenylphosphino)ferrocene]dichloropalladium(II) (1:1 complex with dichloromethane, 5.5 mg, 7 µmol) in acetonitrile (1 mL) is stirred at 80° C. over night. The mixture is diluted with acetonitrile and filtered, and the filtrate is purified by preparative reversed-phase HPLC (Agilent ZORBAX™ SB-C$_{18}$, gradient of acetonitrile in water, 0.15% trifluoroacetic acid).

Yield: 12 mg, ESI mass spectrum [M+H]$^+$=521; Retention time HPLC: 1.00 min (Z017_S04).

The following examples of Table 3 were prepared in analogy to example 36, replacing 1-methyl-4-(tetramethyl-1,3,2-dioxaborolan-2-yl)-1H-pyrazole with the appropriate boronic acid or boronic ester as starting material.

TABLE 3

| Example | R3 | MS [M + H]$^+$ | Retention time [min] | HPLC-Method |
|---|---|---|---|---|
| 36.1 | (3-cyanophenyl-pyridin-3-yl) | 518 | 0.88 | Z018_S04 |
| 36.2 | (3-cyanophenyl-pyridin-4-yl) | 518 | 0.86 | Z018_S04 |
| 36.3 | (3-cyanophenyl-pyrimidin-5-yl) | 519 | 0.99 | Z018_S04 |

Example 37

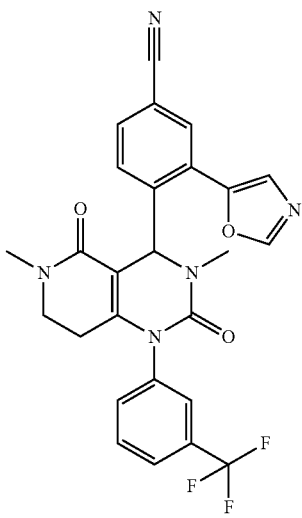 [SMILES: CN1CCC2=C(C1=O)C(c1ccc(C#N)cc1-c1cnco1)N(C)C(=O)N2c1cccc(C(F)(F)F)c1]

4-{3,6-Dimethyl-2,5-dioxo-1-[3-(trifluoromethyl)phenyl]-1H,2H,3H,4H,5H,6H,7H,8H-pyrido[4,3-d]pyrimidin-4-yl}-3-(1,3-oxazol-5-yl)benzonitrile A mixture of 3-bromo-4-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzonitrile (intermediate 21, 55 mg, 106 µmol), 5-(tetramethyl-1,3,2-dioxaborolan-2-yl)-2-(tri-tert-butylsilyl)-1,3-oxazole (111 mg, 0.32 mmol), aqueous potassium carbonate (2 M, 110 µL, 220 µmol) and [1,1′-bis(diphenylphosphino)ferrocene]dichloropalladium (II) (1:1 complex with dichloromethane, 8.7 mg, 11 µmol) in acetonitrile (1 mL) is stirred at 80° C. over night. The mixture is cooled at room temperature, diluted with acetonitrile (3 mL), acidified with trifluoroacetic acid (2 mL) and filtered, and the filtrate is purified by preparative reversed-phase HPLC (Agilent ZORBAX™ SB-C$_{18}$, gradient of acetonitrile in water, 0.15% trifluoroacetic acid). Yield: 20 mg, ESI mass spectrum [M+H]$^+$=508; Retention time HPLC: 1.33 min (Z017_S04).

Example 38

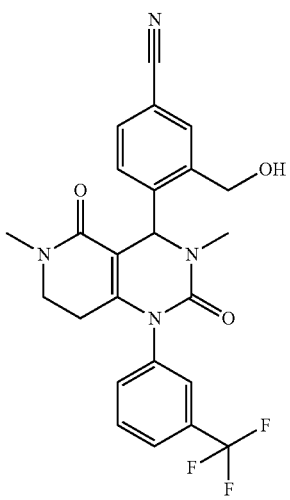 [SMILES: CN1CCC2=C(C1=O)C(c1ccc(C#N)cc1CO)N(C)C(=O)N2c1cccc(C(F)(F)F)c1]

4-{3,6-Dimethyl-2,5-dioxo-1-[3-(trifluoromethyl)phenyl]-1H,2H,3H,4H,5H,6H,7H,8H-pyrido[4,3-d]pyrimidin-4-yl}-3-(hydroxymethyl)benzonitrile A solution of methyl 5-cyano-2-{3,6-dimethyl-2,5-dioxo-1-[3-(trifluoromethyl)phenyl]-1H,2H,3H,4H,5H,6H,7H, 8H-pyrido[4,3-d]pyrimidin-4-yl}benzoate (step 1 of intermediate 24, 100 mg, 0.66 mmol) in tetrahydrofuran (3 mL) is cooled in an ice bath at 4° C. and treated with sodium borohydride (25 mg, 0.66 mmol). A mixture of methanol (136 µL) and tetrahydrofuran (1 mL) is added dropwise, and the mixture is stirred at room temperature for 3 h. Another portion of sodium borohydride (25 mg, 0.66 mmol) is added, and the mixture is stirred at room temperature over night. Another portion of sodium borohydride (25 mg, 0.66 mmol) is added, and the mixture is stirred at room temperature for 3 h. Water is added, and the mixture is cooled in an ice bath at 0° C. The mixture is acidified with glacial acetic acid and extracted with ethyl acetate. The organic layer is washed twice with water, dried over $Na_2SO_4$ and concentrated under reduced pressure. The residue is purified by preparative reversed-phase HPLC (Agilent ZORBAX™ SB-$C_{18}$, gradient of acetonitrile in water, 0.15% formic acid). Yield: 19 mg, ESI mass spectrum [M+H]$^+$=471; Retention time HPLC: 0.96 min (Z017_504).

Example 39

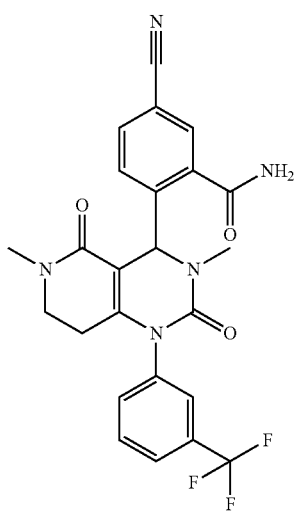 [SMILES: CN1CCC2=C(C1=O)C(c1ccc(C#N)cc1C(N)=O)N(C)C(=O)N2c1cccc(C(F)(F)F)c1]

5-Cyano-2-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzamide Triethylamine (43 µL, 0.31 mmol) is added to a solution of 5-cyano-2-{3,6-dimethyl-2,5-dioxo-1-[3-(trifluoromethyl)phenyl]-1H,2H,3H,4H,5H,6H,7H,8H-pyrido[4,3-d]-pyrimidin-4-yl}benzoic acid (intermediate 24, 50 mg, 0.10 mmol) in N,N-dimethylformamide (1 mL), and the mixture is stirred at room temperature for 5 min. O-(7-Azabenzotriazol-1-yl)-N,N,N',N'-tetramethyluronium hexafluorophosphate (41 mg, 0.11 mmol) is added, and the mixture is stirred for 15 min Ammonium chloride (11 mg, 0.21 mmol) is added, and the mixture is stirred for 1.5 h. The mixture is diluted with acetonitrile and purified by preparative reversed-phase HPLC (Sunfire-$C_{18}$, gradient of acetonitrile in water, 0.1% trifluoroacetic acid). Yield: 16 mg, ESI mass spectrum [M+H]$^+$=484; Retention time HPLC: 0.95 min (Z018_S04).

The following examples of Table 4 were prepared in analogy to example 39, replacing ammonium chloride with the appropriate amine as starting material.

TABLE 4

| Example | R³ | MS [M + H]$^+$ | Retention time [min] | HPLC-Method |
|---------|-----|----------------|---------------------|-------------|
| 39.1 | (5-cyano-2-(N-methylcarbamoyl)phenyl) | 498 | 0.99 | Z018_S04 |
| 39.2 | (5-cyano-2-(N,N-dimethylcarbamoyl)phenyl) | 512 | 1.00 | Z018_S04 |

Example 40

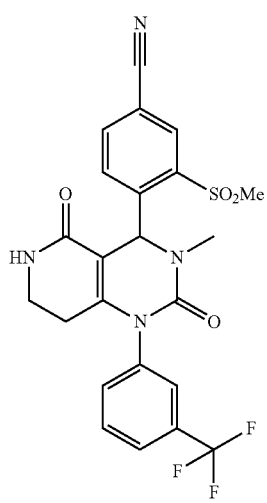 [SMILES: CN1C(=O)N(c2cccc(C(F)(F)F)c2)C2=C(C(=O)NCC2)C1c1ccc(C#N)cc1S(C)(=O)=O]

3-Methanesulfonyl-4-{3-methyl-2,5-dioxo-1-[3-(trifluoromethyl)phenyl]-1H,2H,3H,4H,5H,6H,7H,8H-pyrido[4,3-d]pyrimidin-4-yl}benzonitrile Cesium carbonate (79 mg, 0.25 mmol) is added to a mixture of 4-{2,5-dioxo-1-[3-(trifluoromethyl)phenyl]-1H, 2H,3H,4H,5H,6H,7H,8H-pyrido[4,3-d]pyrimidin-4-yl}-3-methanesulfonylbenzonitrile (intermediate 27, 60 mg, 0.12 mmol) and N,N-dimethylformamide (1 mL). Methyl iodide (23 µL, 0.37 mmol) is added, and the mixture is stirred at room temperature for 2 h. Another portion of methyl iodide (23 µL, 0.37 mmol) is added, and the mixture is stirred for 2 h, diluted with methanol and purified by preparative reversed-phase HPLC (Sunfire-$C_{18}$, gradient of acetonitrile in water, 0.1% trifluoroacetic acid). Yield: 20 mg, ESI mass spectrum [M+H]$^+$=505; Retention time HPLC: 0.96 min (Z017_S04).

Example 41

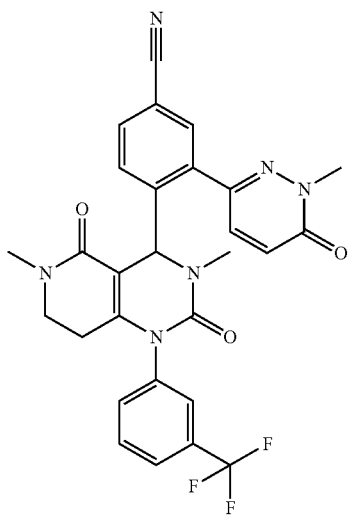 [SMILES: CN1CCC2=C(C1=O)C(c1ccc(C#N)cc1-c1ccc(=O)n(C)n1)N(C)C(=O)N2c1cccc(C(F)(F)F)c1]

4-{3,6-Dimethyl-2,5-dioxo-1-[3-(trifluoromethyl)phenyl]-1H,2H,3H,4H,5H,6H,7H,8H-pyrido[4,3-d]pyrimidin-4-yl}-3-(1-methyl-6-oxo-1,6-dihydro-pyridazin-3-yl)-benzonitrile A mixture of 3-bromo-4-{3,6-dimethyl-2,5-dioxo-1-[3-(trifluoromethyl)phenyl]-1H,2H,3H,4H,5H,6H,7H,8H-pyrido[4,3-d]pyrimidin-4-yl}benzonitrile (intermediate 21, 60 mg, 104 µmol), (1-methyl-6-oxo-1,6-dihydropyridazin-3-yl)boronic acid (50 mg, 162 µmol), aqueous potassium carbonate (2 M, 0.16 mL, 0.32 mmol) and [1,1'-bis-(diphenylphosphino)ferrocene]dichloropalladium(II) (1:1 complex with dichloromethane, 4 mg, 5 µmol) in acetonitrile (1.5 mL) is stirred at 80° C. over night. The mixture is diluted with acetonitrile and filtered, and the filtrate is purified by preparative reversed-phase HPLC (Waters SunFire™-$C_{18}$, gradient of acetonitrile in water, 0.1% TFA). Yield: 7.8 mg, ESI mass spectrum [M+H]$^+$=548; Retention time HPLC: 1.00 min (Z018_S04).

Pharmacological Data

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: I-1270). All other materials were of the highest grade commercially available. The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 µL of these compound dilutions were mixed with 10 µl Neutrophil elastase (9 ng/ml in assay buffer) in a black 384 well OptiPlate (Perkin Elmer, Cat No.: 6007270) and incubated for 15 min at room temperature. Subsequently 10 µL substrate solution in assay buffer were added (250 µM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). $IC_{50}$ values were estimated using a sigmoidal concentration response curve with variable slope. Means of low values were taken as 0%, means of high values as 100%. The $IC_{50}$ values of selected compound in the Neutrophil Elastase assay are listed in Table 5.

TABLE 5

| Example | $IC_{50}$ [nM] |
| --- | --- |
| 1 | 5.7 |
| 1A | 3.1 |
| 1B | 940 |
| 2 | 6.9 |
| 2A | 3.2 |
| 2B | >10,000 |
| 3 | 9.8 |
| 4 | 5.8 |
| 4A | 1.3 |
| 4B | 1,900 |
| 5 | 1.9 |
| 6 | <1 |
| 7 | 1.2 |
| 8A | <1 |
| 8B | 36 |
| 9 | 2.3 |
| 10 | 2.7 |
| 11 | 3.0 |
| 12 | 2.0 |
| 12A | 1.3 |
| 12B | 1,200 |
| 12.1 | 1.1 |
| 12.2 | 2.4 |
| 12.3 | 2.1 |
| 12.4 | 2.0 |
| 12.5 | <1 |
| 12.6 | <1 |
| 12.7 | <1 |
| 12.8 | <1 |
| 12.9 | <1 |
| 13 | 4.3 |
| 14 | 3.0 |
| 15 | 3.2 |
| 15.1 | <1 |
| 15.2 | 2.7 |
| 15.3 | <1 |
| 15.4 | 2.7 |
| 15.5 | <1 |
| 15.6 | <1 |
| 16 | <1 |
| 17 | <1 |
| 18 | 3.8 |
| 19 | 4.9 |
| 20 | 3.7 |
| 21 | 1.9 |

TABLE 5-continued

| Example | IC$_{50}$ [nM] |
|---|---|
| 22 | <1 |
| 23 | <1 |
| 24 | <1 |
| 25 | <1 |
| 26 | <1 |
| 27 | <1 |
| 28 | <1 |
| 29 | <1 |
| 30A | <1 |
| 30B | 12 |
| 31A | <1 |
| 31B | 17 |
| 32A | <1 |
| 32B | 39 |
| 33 | <1 |
| 34 | <1 |
| 35 | <1 |
| 36 | <1 |
| 36.1 | 1.4 |
| 36.2 | 1.3 |
| 36.3 | 1.1 |
| 37 | <1 |
| 38 | 2.7 |
| 38 | <1 |
| 39 | <1 |
| 39.1 | <1 |
| 39.2 | 2.0 |
| 40 | <1 |
| 41 | <1 |

Assay for the Determination of Neutrophil Elastase Inhibitory Activity in Human Plasma Citrated blood from human healthy donors is mixed with zymosan suspension and incubated at room temperature. This leads to the stimulation of neutrophils and the release of neutrophil elastase into the plasma. The stimulated blood is centrifuged to generate the neutrophil elastase enriched plasma.

Preparation of Zymosan Working Solution:

Zymosan (100 mg) is mixed with saline (0.9%, 10 mL) and stored at 4° C. for up to one week (note: zymosan does not dissolve in the saline and is used as a suspension).

Whole Blood Stimulation:

A single 45 ml blood sample is taken into a 50 ml tube containing citrate (3.13%, 5 mL) and the tube is gently inverted 4 times.

Immediately after blood sampling, zymosan working solution (5 mL) is added.

After the addition of zymosan working solution, the tubes are capped, mixed gently and incubated at 22° C. for 15 min on a shaker at 20 rpm.

Make 10 ml aliquots after the incubation time.

Centrifuge the 15 ml tubes at 800 g for 15 min at 4° C. in a Jouan centrifuge.

Harvest the plasma and make 1-5 ml aliquots.

Store the plasma at −80° C.

Various concentrations of the neutrophil elastase inhibitor are incubated with plasma. Subsequently, the enzyme activity is measured using the fluorogenic substrate MeOSuc-Ala-Ala-Pro-Val-AMC (Bachem Cat. No. I-1270, substrate concentration: 250 μM, pH 7.5, 25 mM TRIS buffer, 250 mM NaCl) in analogous fashion as described for the human neutrophil assay. A dose response curve is generated to calculate the EC$_{50}$ of the inhibitor. The analysis of the data is performed by the calculation of the percentage of fluorescence in the presence of the test compound compared to the fluorescence of the vehicle control after subtracting the background fluorescence: An inhibitor of the neutrophil elastase enzyme will give values between 100% control (no inhibition) and 0% control (complete inhibition). The human plasma shift of selected compounds can be calculated using the following equation:

$$\text{Human plasma shift} = (IC_{50} \text{ in human plasma assay}) / (IC_{50} \text{ in human neutrophil elastase assay})$$

The IC$_{50}$ values of selected compounds in the human plasma assay described above are listed in Table 6.

TABLE 6

| Example | IC$_{50}$ [nM] |
|---|---|
| 1 | 11 |
| 1A | 3.4 |
| 2 | 8.2 |
| 2A | 5.4 |
| 3 | 13 |
| 4 | 2.9 |
| 4A | 2.7 |
| 5 | 1.1 |
| 6 | 1 |
| 7 | 2 |
| 8A | <1 |
| 9 | 3.1 |
| 10 | 2.4 |
| 11 | 2.9 |
| 12 | 2.8 |
| 12A | <1 |
| 12.1 | <1 |
| 12.2 | 2.5 |
| 12.3 | 3.6 |
| 12.4 | 5.1 |
| 12.5 | <1 |
| 12.6 | <1 |
| 12.7 | <1 |
| 12.8 | 1.1 |
| 12.9 | 1 |
| 13 | 2.2 |
| 14 | 14 |
| 15 | 7.8 |
| 15.1 | 2.6 |
| 15.2 | 6.7 |
| 15.3 | 4.3 |
| 15.4 | 3.9 |
| 15.5 | <1 |
| 15.6 | 1.6 |
| 16 | 2.4 |
| 17 | <1 |
| 18 | 6.7 |
| 19 | 18 |
| 20 | 6.9 |
| 21 | 1.9 |
| 22 | 2.5 |
| 23 | 1.1 |
| 24 | 1.4 |
| 25 | 1.5 |
| 26 | 1.4 |
| 27 | <1 |
| 28 | 1.1 |
| 29 | <1 |
| 30A | <1 |
| 31A | <1 |
| 32A | <1 |
| 33 | 5.3 |
| 34 | 1.6 |
| 35 | <1 |
| 36 | 2.3 |
| 36.1 | 1.8 |
| 36.2 | 1.8 |
| 36.3 | 1.4 |
| 37 | 1.1 |
| 38 | 1.4 |
| 39 | <1 |
| 39.1 | <1 |
| 39.2 | 8.1 |
| 40 | <1 |
| 41 | 1.0 |

Assay for the Determination of Metabolic Stability with Human Liver Microsomes

The metabolic degradation of the test compound is assayed at 37° C. with pooled human liver microsomes. The final incubation volume of 100 μl per time point contains TRIS buffer pH 7.6 (0.1 M), magnesium chloride (5 mM), microsomal protein (1 mg/ml) and the test compound at a final concentration of 1 μM. Following a short preincubation period at 37° C., the reactions are initiated by addition of beta-nicotinamide adenine dinucleotide phosphate, reduced form (NADPH, 1 mM) and terminated by transferring an aliquot into acetonitrile after different time points. Additionally, the NADPH-independent degradation is monitored in incubations without NADPH, terminated at the last time point. The [%] remaining test compound after NADPH independent incubation is reflected by the parameter c(control) (metabolic stability). The quenched incubations are pelleted by centrifugation (10'000 g, 5 min) An aliquot of the supernatant is assayed by LC-MS/MS for the amount of parent compound.

The half-life ($t_{1/2}$ INVITRO) is determined by the slope of the semilogarithmic plot of the concentration-time profile. The intrinsic clearance (CL_INTRINSIC) is calculated by considering the amount of protein in the incubation:

CL_INTRINSIC [μl/min/mg protein]=(ln 2/(half-life [min]* protein content [mg/ml]))*1'000.

The half-life ($t_{1/2}$ INVITRO) values of selected compounds in the metabolic stability assay described above are listed in Table 7.

TABLE 7

| Example | $t_{1/2}$ INVITRO [min] |
|---|---|
| 6 | >130 |
| 9 | >130 |
| 35 | >130 |
| 1A | >130 |
| 2A | >130 |
| 30A | >130 |
| 31A | >130 |
| 4A | >130 |
| 8A | >130 |
| 36 | >130 |
| 37 | >130 |
| 39 | >130 |
| 39.1 | >130 |
| 40 | >130 |
| 41 | >130 |

Assay for the Determination of Metabolic Stability with Human Hepatocytes

The metabolic degradation of the test compound is assayed in a human hepatocyte suspension. Human hepatocytes (typically cryopreserved) are incubated in an appropriate buffer system (e.g. Dulbecco's modified eagle medium plus 3.5 μg glucagon/500 mL, 2.5 mg insulin/500 mL and 3.75 mg/500 mL hydrocortison) containing 5% species serum. Following a (typically) 30 min preincubation in an incubator (37° C., 10% $CO_2$), 5 μl of test compound solution (80 μM; from 2 mM stock solution in DMSO diluted 1:25 with medium) are added into 395 μl hepatocyte suspension (cell density in the range 0.25-5*10$^6$ cells/mL, typically 1*10$^6$ cells/mL; final concentration of test compound 1 μM, final DMSO concentration 0.05%). The cells are incubated for six hours (incubator, orbital shaker) and samples (25 μl) are taken at 0, 0.5, 1, 2, 4 and 6 hours. Samples are transferred into acetonitrile and pelleted by centrifugation (5 min) The supernatant is transferred to a new 96-deepwell plate, evaporated under nitrogen and resuspended. The decline of parent compound is analyzed by LC-MS/MS.

The intrinsic clearance CL_INTRINSIC is calculated as follows:

CL_INTRINSIC=Dose/AUC=($C_0$/CD)/(AUD+$c_{last}$/k)* 1'000/60

($C_0$: initial concentration in the incubation [μM], CD: cell density of vital cells [10$^6$ cells/mL], AUD: area under the data [μM*h], $c_{last}$: concentration of last data point [μM], k: slope of the regression line for parent decline [h$^{-1}$])

The calculated in vitro hepatic intrinsic clearance can be scaled up to the intrinsic in vivo hepatic clearance and used to predict hepatic in vivo blood clearance (CL) by the use of a liver model (well stirred model):

CL_INTRINSIC_INVIVO [ml/min/kg]=(CL_INTRINSIC [μL/min/10$^6$ cells]*hepatocellularity [10$^6$ cells/g liver]*liver factor [g/kg bodyweight])/1'000

CL [ml/min/kg]=CL_INTRINSIC_INVIVO [ml/min/kg]*hepatic blood flow [ml/min/kg]/(CL_INTRINSIC_INVIVO [ml/min/kg]+hepatic blood flow [ml/min/kg])

$Q_h$ [%]=CL [ml/min/kg]/hepatic blood flow [ml/min/kg])

(Hepatocellularity, human: 120*10$^6$ cells/g liver; liver factor, human: 25.7 g/kg bodyweight; blood flow, human: 21 ml/(min*kg))

The in vitro hepatic intrinsic clearance values of selected compounds in the metabolic stability assay described above are listed in Table 8.

TABLE 8

| Example | CL [ml/min/kg] |
|---|---|
| 34 | 4 |
| 35 | 1 |
| 1A | 0 |
| 30A | 3 |
| 31A | 3 |
| 32A | 3 |
| 8A | 2 |
| 40 | 1 |

Assay for Determination of Drug Transport Across Human Caco-2 Cells

The assay provides information on the potential of a compound to pass the cell membrane, on the extent of oral absorption as well as on whether the compound is actively transported by uptake and/or efflux transporters. For the measurement of permeability across polarized, confluent human cancer colon carcinoma cells 2 (Caco-2) cell monolayers grown on permeable filter supports are used as the in vitro absorption model.

Apparent permeability coefficients (PE) of the compounds across the Caco-2 monolayers are measured (pH 7.2, 37° C.) in apical-to-basal (AB) (absorptive) and basal-to-apical (BA) (secretory) transport direction. AB permeability (PEAB) represents drug absorption from the intestine into the blood and BA permeability (PEBA) drug secretion from the blood back into the intestine via both passive permeability as well as active transport mechanisms mediated by efflux and uptake transporters that are expressed on the Caco-2 cells. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB suggests the involvement of an apical efflux transporter (like P-gp) and/or basolateral uptake transporter; higher PEAB than PEBA permeability suggests involvement of an apical uptake transporter (like PepT1) and/or basolateral efflux transporter (like MRP3). Active transport is concentration-dependently saturable.

Caco-2 cells ($1-2*10^5$ cells/$cm^2$ area) are seeded on filter inserts (Costar transwell polycarbonate or PET filters, 0.4 µm pore size) and cultured (DMEM) for 10 to 25 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H_2O$, 15 mM HEPES, 20 mM glucose, pH 7.2) to prepare the transport solutions (typically 10 µM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by LC-MS/MS or scintillation counting. Sampled receiver volumes are replaced with fresh receiver solution.

The apparent permeability coefficients (PEAB and PEBA) of selected compounds in the Caco-2 drug transport assay described above are listed in Table 9.

TABLE 9

| Example | PEAB [cm/s] | PEBA [cm/s] |
| --- | --- | --- |
| 6 | 0.000037 | 0.000080 |
| 9 | 0.0000061 | 0.000063 |
| 34 | 0.000011 | 0.000079 |
| 35 | 0.0000057 | 0.000100 |
| 1A | 0.0000066 | 0.000044 |
| 2A | 0.0000047 | 0.000031 |
| 30A | 0.000011 | 0.000085 |
| 31A | 0.000012 | 0.000100 |
| 32A | 0.0000069 | 0.000061 |
| 4A | 0.000017 | 0.000034 |
| 8A | 0.000020 | 0.000097 |
| 36 | 0.000030 | 0.000083 |
| 36.1 | 0.000026 | 0.000110 |
| 36.2 | 0.000025 | 0.000150 |
| 36.3 | 0.000012 | 0.000110 |
| 37 | 0.000032 | 0.000090 |
| 38 | 0.000024 | 0.000091 |
| 39 | 0.0000042 | 0.000059 |
| 39.1 | 0.0000067 | 0.000081 |
| 39.2 | 0.000011 | 0.000110 |
| 40 | 0.000017 | 0.000087 |
| 41 | 0.000006 | 0.000091 |

Assay for Determination of Aqueous Solubility ("High Throughput Method")

The aqueous solubility of a compound is determined by comparing the amount dissolved in aqueous buffer (containing 2.5% DMSO) to the amount dissolved in an acetonitrile/water (1/1) solution. Starting from a 10 mM DMSO stock solution, aliquots are diluted with acetonitrile/water (1/1) and McIlvaine buffer pH 6.8, respectively. After 24 h of shaking, the solutions or suspensions are filtered and analyzed by LC-UV. The amount dissolved in buffer is compared to the amount dissolved in the acetonitrile/water (1/1) solution. Solubility is measured from 0.001 to 0.125 mg/ml at a DMSO concentration of 2.5%. If more than 90% of the compound is dissolved in buffer, the value is marked with ">".

The aqueous solubility of selected compounds in the solubility assay described above is listed in Table 10.

TABLE 10

| Example | Aqueous solubility [mg/mL] |
| --- | --- |
| 6 | >0.088 |
| 9 | 0.088 |
| 35 | 0.084 |
| 1A | >0.100 |
| 2A | >0.092 |
| 30A | 0.060 |
| 31A | 0.011 |
| 32A | 0.019 |
| 4A | >0.089 |
| 8A | 0.061 |
| 36 | 0.042 |
| 36.1 | 0.070 |
| 36.2 | 0.070 |
| 36.3 | 0.076 |
| 37 | 0.060 |
| 38 | 0.089 |
| 39 | 0.078 |
| 39.1 | 0.080 |
| 39.2 | 0.086 |
| 41 | 0.093 |

Assay for Determination of Aqueous Solubility ("Shaked Flask Method")

Saturated solutions are prepared in well plates by adding an appropriate volume of selected aqueous media (typically in the range of 0.25-1.5 ml) into each well which contains a known quantity of solid drug substance (typically in the range 0.5-5.0 mg). The wells are shaken or stirred for a predefined time period (typically in a range of 2-24 h) and then filtered using appropriate filter membranes (typically PTFE-filters with 0.45 µm pore size). Filter absorption is avoided by discarding the first few drops of filtrate. The amount of dissolved drug substance is determined by UV spectroscopy or by HPLC with UV-detection. In addition, the pH of the aqueous saturated solution is measured using a glass-electrode pH meter. Example 1A, example 30A, example 31A, example 32A, example 36 and example 37 exhibit a solubility of ≥0.01 mg/mL at pH 6.8 (McIlvaine buffer) in this solubility assay.

Assay for Determination of Cytochrome P450 2C9 Inhibition

The inhibition of cytochrome P450 2C9-isoenzyme catalysed hydroxylation of Diclofenac by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.1 mg/ml), Diclofenac (10 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound.

Within each of the assay runs, the $IC_{50}$ of a positive control inhibitor (sulfaphenazole) is determined Experimental $IC_{50}$ values are calculated by least square regression according to the following equation:

% control activity=(100% control activity/(1+$(I/IC_{50})$*S))-B (I=inhibitor concentration, S=slope factor, B=background activity)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned ">highest concentration tested" (usually >50 µM). Example 1A, Example 31A and Example 34 exhibit $IC_{50}$ values >50 µM in this assay.

Assay for Determination of Cytochrome P450 2C19 Inhibition

The inhibition of cytochrome P450 2C19-isoenzyme catalysed hydroxylation of Mephenytoin by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.5 mg/ml), (S)-Mephenytoin (70 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (tranylcypromine) is determined Experimental $IC_{50}$ values are calculated by least square regression according to the following equation:

% control activity=(100% control activity/(1+$(I/IC_{50})$*S))-B (I=inhibitor concentration, S=slope factor, B=background activity)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned ">highest concentration tested" (usually >50 µM). Example 1A, Example 31A and Example 34 exhibit $IC_{50}$ values >50 µM in this assay.

Assay for Determination of Cytochrome P450 2C8 Inhibition

The inhibition of cytochrome P450 2C8-isoenzyme catalysed deethylation of Amodiaquine by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.05 mg/ml), Amodiaquine (1 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (Montelukast) is determined Experimental $IC_{50}$ values are calculated by least square regression according to the following equation:

% control activity=(100% control activity/(1+$(I/IC_{50})$*S))-B (I=inhibitor concentration, S=slope factor, B=background activity)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned ">highest concentration tested" (usually >50 µM). Example 1A, Example 31A and Example 34 exhibit $IC_{50}$ values >50 µM in this assay.

Assay for Determination of Cytochrome P450 Induction

Cytochrome P450 (CYP) induction can affect the pharmacokinetics of a drug molecule upon multiple dosing, which can result in pharmacokinetic drug-drug interactions with coadministered drugs. CYP induction can lead to decreased exposure of the inducing compound (e.g. autoinduction) or decreased exposure of a coadministered compound metabolized by the induced enzyme. CYP induction can also lead to an increase in the metabolism of a drug causing changes in pharmacological (active metabolite) and toxicological (toxic metabolite) outcomes. The primary mechanism by which drugs cause enzyme induction is by the activation of gene transcription. The nuclear receptor that are most commonly involved in the activation of transcription of drug-metabolizing enzyme CYP3A4 and transporters is the pregnane X receptor (PXR). To assess induction of metabolizing enzyme CYP3A4, cryopreserved HepaRG® cells are seeded at a density of 1.0×105 per 96 well. Cells are allowed to equilibrate for 72 hours prior to exposure of 10 µM test article for 48 hours with renewal of test article every 24 hours. Known prototypical CYP3A4 inducers Rifampicin is used as a positive control at a concentration of 25 µM. After 48 hours of exposure, medium containing the test article is removed and cells were washed with phosphate buffered saline (PBS) prior to mRNA isolation.

Calculations:

Fold induction=(Enzyme mRNA Compound)/(Enzyme mRNA Solvent Control)

Inducer Potency=(Fold Compound)/(Fold Rifampicin)*100

Assay for Determination of hERG Inhibition

The inhibition of the hERG (human ether-a-go-go-related gene) potassium channel can be determined as described in Rast, G., & Guth, B. D., Journal of Pharmacological and ToxicologicalMethods (2014), http://dx.doi.org/10.1016/j.vascn.2014.08.001.

Combinations

The compounds of general formula 1 may be used on their own or combined with other active substances of formula 1 according to the invention. The compounds of general formula 1 may optionally also be combined with other pharmacologically active substances. These include, β2-adrenoceptor-agonists (short and long-acting), anticholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors, non-steroidale anti-inflammatory agents (NSAIDs), Cathepsin C (or DPPI/Dipeptidylaminopeptidase I) inhibitors, CRTH2 antagonists, DP1-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergicreceptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immuno-therapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, that is:
  Betamimetics with corticosteroids, PDE4-inhibitors, CRTH2-inhibitors or LTD4-antagonists,
  Anticholinergics with betamimetics, corticosteroids, PDE4-inhibitors, CRTH2-inhibitors or LTD4-antagonists,
  Corticosteroids with PDE4-inhibitors, CRTH2-inhibitors or LTD4-antagonists
  PDE4-inhibitors with CRTH2-inhibitors or LTD4-antagonists
  CRTH2-inhibitors with LTD4-antagonists Pharmaceutical Compositions Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; acute respiratory distress syndrome;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; a) drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, *chlamydia, Candida, aspergillus*, cryptococcal meningitis, *Pneumocystis carnii*, cryptosporidiosis, histoplasmosis, toxoplasmosis, trypanosome infection and leishmaniasis and, 9. other diseases: traumatic brain injury, abdominal aortic aneurism The present invention is directed to compounds of general formula 1 which are useful in the prevention and/or treatment of a disease and/or condition wherein the activity of inhibitors of neutrophil elastase is of therapeutic benefit, including but not limited to the treatment and/or prevention of asthma and allergic diseases, gastrointestinal inflammatory diseases, glomerulonephritis, eosinophilic diseases, chronic obstructive pulmonary disease, infection by pathogenic microbes, rheumatoid arthritis, neutrophilic diseases, cystic fibrosis (CF), non-cystic fibrosis, idiopathic pulmonary fibrosis, bronchiectasis, ANCA-associated vasculitis, lung cancer, non-cyctic fibrosis bronchiectasis, emphysema, chronic bronchitis, acute lung injury (ALI), acute respiratory distress syndrome (ARDS), pulmonary hypertension, pulmonary arterial hypertension (PAH), Alpha-1-antitrypsin deficiency (AATD), obesity and related inflammation, e.g. chronic adipose tissue inflammation, adipose inflammation and high-fat diet induced inflammation, insulin resistance, diabetes, fatty liver and liver steatosis.

In a further aspect of the present invention the present invention relates to methods for the treatment or prevention of above mentioned diseases and conditions, which method comprises the administration of an effective amount of a compound of general formula 1 to a human being.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

LIST OF ABBREVIATIONS

TABLE 5

| ACN | acetonitrile |
|---|---|
| aq. | aqueous |
| Boc | tert-butyloxycarbonyle |
| d | day |
| DCM | dichloromethane |
| DEA | diethylamine |
| DIPEA | N,N-diisopropylethylamine |
| DMAP | 4-dimethylaminopyridine |
| DMF | N,N-dimethylformamide |
| DMSO | dimethyl sulfoxide |
| h | hour |
| HATU | O-(7-azabenzotriazol-1-yl)-N,N,N',N'-tetramethyluronium hexafluoro-phosphate |
| MeTHF | methyl tetrahydrofuran |
| RT, r.t. | room temperature |
| rt | retention time |
| TBME | tert-butyl methyl ether |
| TBTU | O-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | para-toluene sulfonic acid |

What we claim:
1. A compound of formula 1

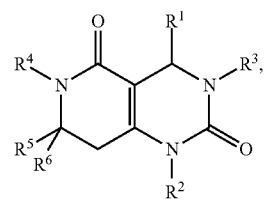

wherein
$R^1$ is phenyl or pyridinyl; each ring optionally substituted with one or two substituents independently selected from the group consisting of halogen, NC—, $H_2N$—, $R^{1.1}$, $R^{1.1}O$—, $R^{1.2}$, $R^{1.3}$, $R^{1.4}(O)S$—, $R^{1.4}(O)_2S$— and $R^{1.5}R^{1.5}N(O)C$—;
$R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl;
$R^{1.2}$ is HO—$C_{1-6}$-alkyl- or $R^{1.1}$—O—$C_{1-6}$-alkyl-;
$R^{1.3}$ is phenyl or a five- or six-membered heterocyclic or heteroaryl ring, wherein one, two or three elements are replaced by an element independently selected from the group consisting of N, O, S, S(O) and $S(O)_2$; each ring optionally substituted with one, two or three substituents independently selected from the group consisting of halogen, NC—, H$_2$N—, HO—, O=, R$^{1.3.1}$, R$^{1.3.1}$O—, R$^{1.3.1}$—(O)C—, R$^{1.3.2}$, R$^{1.3.1}$(O)$_2$S— and R$^{1.3.3}$;

R$^{1.3.1}$ is independently selected from R$^{1.1}$;

R$^{1.3.2}$ is independently selected from R$^{1.2}$;

R$^{1.3.3}$ is independently selected from the group consisting of HO(O)C—, H$_2$N(O)C—, R$^{1.1}$—O—(O)C—, R$^{1.1}$—NH—(O)C— and (R$^{1.1}$)$_2$N—(O)C—;

R$^{1.4}$ is independently selected from the group consisting of H, HO—, R$^{1.1}$ and R$^{1.2}$;

R$^{1.5}$ is independently selected from the group consisting of H, R$^{1.1}$, R$^{1.2}$, C$_{1-6}$-alkyl-C$_{3-6}$-cycloalkyl- and C$_{3-6}$-cycloalkyl-C$_{1-6}$-alkyl-, each optionally substituted with one or two substituents independently selected from R$^{1.5.1}$, R$^{1.5.2}$ and R$^{1.5.3}$;

R$^{1.5.1}$ is selected from the group consisting of HO—, halogen, NC—, R$^{1.1}$O—, R$^{1.5.4}$, R$^{1.5.5}$ and R$^{1.5.6}$; or R$^{1.5.2}$ denotes a four-membered heterocyclic ring containing one element independently selected from among N, O, S, S(O) and S(O)$_2$; or R$^{1.5.3}$ denotes a five- or six-membered heterocyclic or heteroaryl ring containing one, two or three elements independently selected from among N, O, S, S(O) and S(O)$_2$; each of the rings optionally substituted with one or two substituents independently selected from among HO—, O=, halogen, NC—, R$^{1.1}$, R$^{1.1}$O—, R$^{1.1}$—(O)C—, HO—C$_{1-6}$-alkyl-, R$^{1.1}$—O—C$_{1-6}$-alkyl-, R$^{1.5.4}$, R$^{1.5.5}$ and R$^{1.5.6}$; or two substituents are together R$^{1.5.7}$;

R$^{1.5.4}$ is independently selected from the group consisting of H$_2$N—, R$^{1.1}$—HN—, (R$^{1.1}$)$_2$N—, R$^{1.1}$—(O)C—HN— and R$^{1.1}$—(O)C—(R$^{1.1}$)N—;

R$^{1.5.5}$ is independently selected from the group consisting of R$^{1.1}$—(O)S—, R$^{1.1}$—(O)$_2$S—, R$^{1.1}$(HN)S—, R$^{1.1}$(HN)(O)S—, R$^{1.1}$(R$^{1.1}$N)S—, R$^{1.1}$(R$^{1.2}$N)S—, R$^{1.1}$(R$^{1.1}$N)(O)S—, R$^{1.1}$(R$^{1.2}$N)(O)S—, R$^{1.1}$(NC—N)S— and R$^{1.1}$(NC—N)(O)S—;

R$^{1.5.6}$ is independently selected from the group consisting of HO(O)C—, H$_2$N(O)C—, R$^{1.1}$—O—(O)C—, R$^{1.1}$—NH—(O)C— and (R$^{1.1}$)$_2$N—(O)C—;

R$^{1.5.7}$ is independently selected from the group consisting of C$_{1-6}$-alkylene and C$_{1-6}$-haloalkylene, wherein optionally one or two CH$_2$-groups are replaced by —HN—, —(R$^{1.1}$)N—, —(R$^{1.1}$(O)C—)N—, —O—, —S—, —S(O)— or —S(O)$_2$—;

or R$^{1.5}$ is phenyl or a five- or six-membered heterocyclic or heteroaryl ring containing one, two or three elements independently selected from N, O, S, S(O) and S(O)$_2$; each ring optionally substituted with one or two substituents independently selected from HO—, O=, NC—, halogen, R$^{1.1}$, R$^{1.1}$O—, R$^{1.1}$—(O)C—, R$^{1.2}$, R$^{1.5.4}$, R$^{1.5.5}$ and R$^{1.5.6}$; or two substituents are together R$^{1.5.7}$;

or two R$^{1.5}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and S(O)$_2$; optionally substituted with one or two substituents, independently selected from among HO—, F, O=, NC—, R$^{1.1}$, R$^{1.1}$O—, R$^{1.1}$—(O)C—, R$^{1.2}$, R$^{1.5.4}$, R$^{1.5.5}$, R$^{1.5.6}$, phenyl and a five- or six-membered heterocyclic or heteroaryl ring containing one, two or three elements independently selected from among N, O, S, S(O) and S(O)$_2$; or two substituents are together R$^{1.5.7}$;

R$^2$ is phenyl or pyridinyl; each ring optionally substituted with one or two substituents independently selected from halogen, C$_{1-4}$-alkyl- and C$_{1-4}$-haloalkyl-;

R$^3$ is a residue independently selected from the group consisting of

R$^{3.1}$—;

R$^{3.2}$(O)C—;

R$^{3.2}$O(O)C—;

R$^{3.2}$O(O)C-A-;

R$^{3.2}$(O)$_2$S—;

(R$^{3.2}$)$_2$N(O)C and (R$^{3.2}$)$_2$N(O)C-A-;

R$^{3.1}$ is independently selected from the group consisting of H, R$^{3.3}$, R$^{3.4}$, C$_{1-6}$-alkyl-C$_{3-6}$-cycloalkyl- and C$_{3-6}$-cycloalkyl-C$_{1-6}$-alkyl-, each optionally substituted with one or two substituents independently selected from R$^{3.11}$—;

R$^{3.1.1}$ is selected from the group consisting of HO—, halogen, NC—, R$^{3.3}$O—, R$^{3.5}$, R$^{3.6}$ and R$^{3.7}$ or R$^{3.1.1}$ denotes a ring independently selected from phenyl and a four-membered heterocyclic ring containing one element independently selected from among N, O, S, S(O) and S(O)$_2$ or R$^{3.1.1}$ denotes a five- or six-membered heterocyclic or heteroaryl ring containing one, two or three elements independently selected from among N, O, S, S(O) and S(O)$_2$;

each of the rings optionally substituted with one or two substituents independently selected from among HO—, O=, halogen, NC—, R$^{3.3}$, R$^{3.3}$O—, R$^{3.3}$—(O)C—, R$^{3.4}$, R$^{3.5}$, R$^{3.6}$ and R$^{3.7}$ or two substituents are together R$^{3.8}$;

R$^{3.2}$ is independently selected from R$^{3.1}$, phenyl and a five- or six-membered heterocyclic or heteroaryl ring containing one, two or three elements independently selected from N, O, S, S(O) and S(O)$_2$; each ring optionally substituted with one or two substituents independently selected from HO—, O=, NC—, halogen, R$^{3.3}$, R$^{3.3}$O—, R$^{3.3}$—(O)C—, R$^{3.4}$, R$^{3.5}$, R$^{3.6}$ and R$^{3.7}$ or two substituents are together R$^{3.8}$;

or two R$^{3.2}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and S(O)$_2$; optionally substituted with one or two substituents, independently selected from among HO—, F, O=, NC—, R$^{3.3}$, R$^{3.3}$O—, R$^{3.3}$—(O)C—, R$^{3.4}$, R$^{3.5}$, R$^{3.6}$, R$^{3.7}$, phenyl and a five- or six-membered heterocyclic or heteroaryl ring containing one, two or three elements independently selected from among N, O, S, S(O) and S(O)$_2$; or two substituents are together R$^{3.8}$;

R$^{3.3}$ is independently selected from the group consisting of C$_{1-6}$-alkyl-, C$_{3-6}$-cycloalkyl-, C$_{1-6}$-haloalkyl- and C$_{3-6}$-halocycloalkyl;

R$^{3.4}$ is HO—C$_{1-6}$-alkyl- or R$^{3.3}$—O—C$_{1-6}$-alkyl-;

R$^{3.5}$ is independently selected from the group consisting of H$_2$N—, R$^{3.3}$—HN—, (R$^{3.3}$)$_2$N—, R$^{3.3}$—(O)C—HN— and R$^{3.3}$—(O)C—(R$^{3.3}$)N—;

R$^{3.6}$ is independently selected from the group consisting of R$^{3.3}$—(O)S—, R$^{3.3}$—(O)$_2$S—, R$^{3.3}$(HN)S—, R$^{3.3}$(HN)(O)S—, R$^{3.3}$(R$^{3.3}$N)S—, R$^{3.3}$(R$^{3.3}$N)(O)

S—, $R^{3.3}(R^{3.4}N)S$—, $R^{3.3}(R^{3.4}N)(O)S$—; $R^{3.3}(NC=N)S$— and $R^{3.3}(NC=N)(O)S$—;

$R^{3.7}$ is independently selected from the group consisting of HO(O)C—, $H_2N(O)C$—, $R^{3.3}$—O—(O)C—, $R^{3.3}$—NH—(O)C— and $(R^{3.3})_2N$—(O)C—;

$R^{3.8}$ is independently selected from the group consisting of $C_{1-6}$-alkylene and $C_{1-6}$-haloalkylene, wherein optionally one or two $CH_2$-groups are replaced by —HN—, —$(R^{3.3})N$—, —$(R^{3.4})N$—, —$(R^{3.3}(O)C$—)N—, —$(R^{3.4}(O)C$—)N—, —O—, —S—, —S(O)— or —S(O)$_2$—;

A is —$CH_2$—, —$CH_2$—$CH_2$— or —$CH_2$—$CH_2$—$CH_2$—; optionally substituted with one or two substituents independently selected from the group consisting of halogen, $R^{3.3}$, $R^{3.3}O$— and $R^{3.4}$ or two substituents together are $R^{3.8}$;

$R^4$ is $R^3$;

$R^5$, $R^6$ is independently selected from H, $C_{1-6}$-alkyl-, $C_{3-6}$-cycloalkyl-, $C_{1-6}$-haloalkyl-, $C_{3-6}$-halocycloalkyl-, HO—$C_{1-6}$-alkyl- and $C_{1-6}$-alkyl-O—$C_{1-6}$-alkyl;

or $R^5$ and $R^6$ are together $C_{1-6}$-alkylene or $C_{1-6}$-haloalkylene, wherein optionally one $CH_2$-group can be replaced by —O—, —S—, —S(O)— or —S(O)$_2$—;

or a pharmaceutically acceptable salt thereof.

2. A compound of formula 1 according to claim 1, wherein $R^1$ denotes -phenyl-CN or a pharmaceutically acceptable salt thereof.

3. A compound of formula 1 according to claim 1, wherein $R^2$ is selected from the group consisting of -phenyl-CF$_3$, -phenyl-CHF$_2$, -pyridyl-CF$_3$, and -pyridyl-CHF$_2$ or a pharmaceutically acceptable salt thereof.

4. A compound of formula 1 according to claim 1, wherein $R^3$ is selected from the group consisting of H, $C_{1-3}$-alkyl, —CONH—$C_{1-3}$-alkyl, —CONH—$C_{1-3}$-alkyl-OH, —$CH_2$—$CO_2$—$C_{1-3}$-alkyl, —$CH_2$—CO—N($C_{1-3}$-alkyl)$_2$ and —$CH_2$—CO—NH—$C_{1-3}$-alkyl;

or a pharmaceutically acceptable salt thereof.

5. A compound of formula 1 according to claim 1, wherein $R^4$ is selected from the group consisting of H, $C_{1-3}$-alkyl and —CONH—$C_{1-4}$-alkyl-OH;

or a pharmaceutically acceptable salt thereof.

6. A compound of formula 1 according to claim 1, wherein $R^5$ and $R^6$ independently from each other denote H or $C_{1-3}$-alkyl;

or a pharmaceutically acceptable salt thereof.

7. A compound of formula 1 according to claim 1, wherein $R^1$ denotes a group of formula a.1

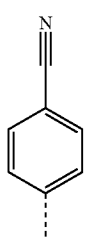

a.1

$R^2$ is selected from the group consisting of a group of formula a.2 or a.3

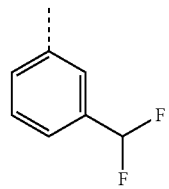

a.2

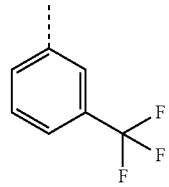

a.3

$R^3$ is selected from the group consisting of H, $CH_3$, —CONH—$CH_3$, —CONH—$CH_2CH_2OH$—$CH_2$—COO—$CH_3$, —$CH_2$—CO—N($CH_3$)$_2$ and —$CH_2$—CO—NHCH$_3$, $R^4$ is selected from the group consisting of H, $CH_3$ and —CONH—$CH_2CH_2CH_2$—OH; and $R^5$ and $R^6$ independently from each other denote H or $CH_3$;

or a pharmaceutically acceptable salt thereof.

8. A compound of formula 1 according to claim 1 selected from the group consisting of compounds 1.a to 1.o

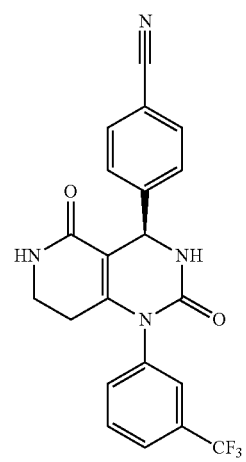

1.a

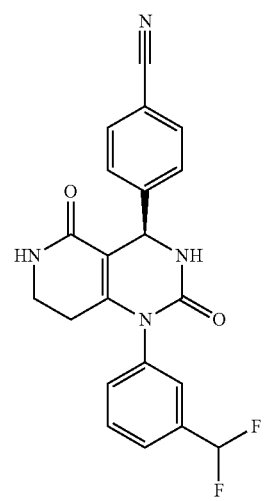

1.b 1.c
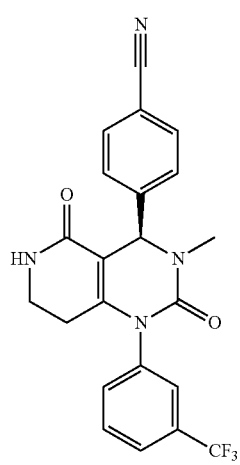
1.d
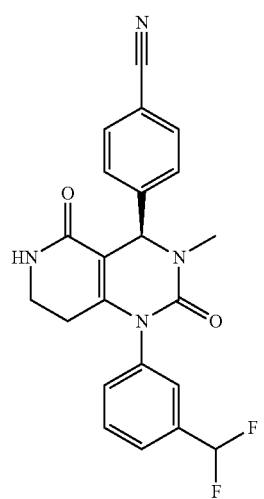
1.e
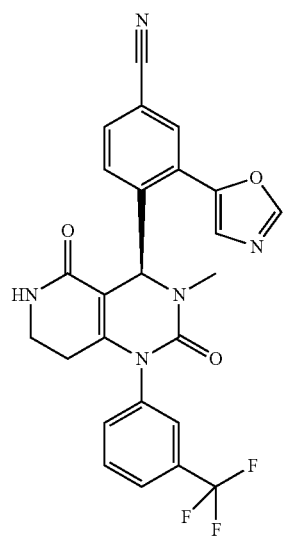
1.f
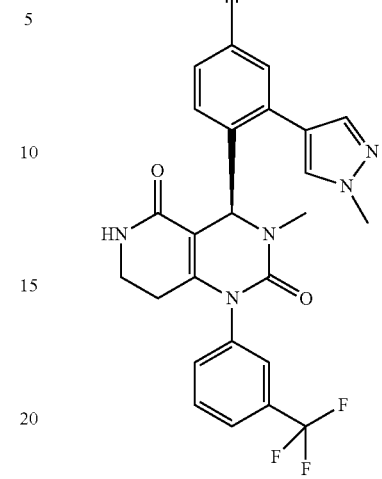
1.g
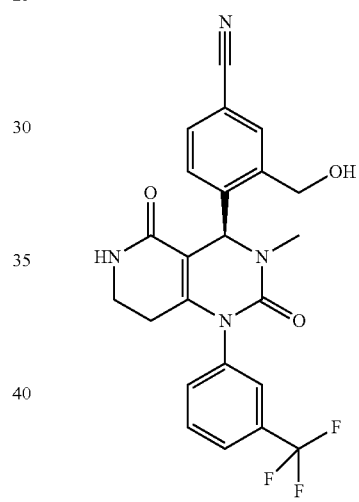
1.h
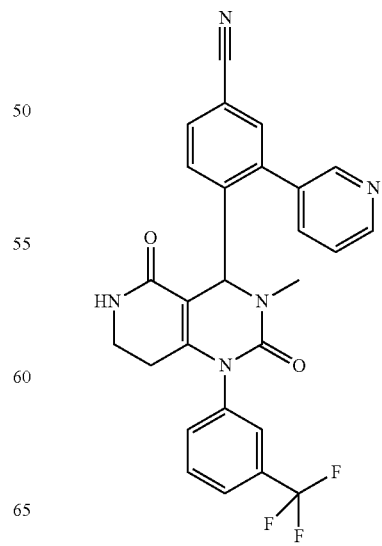

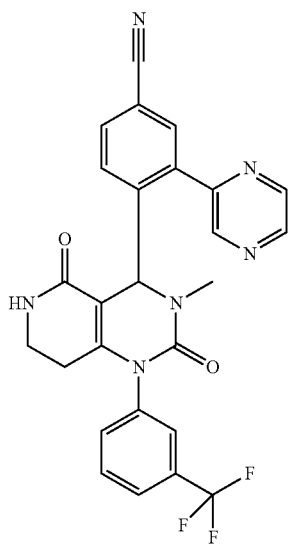
1.i
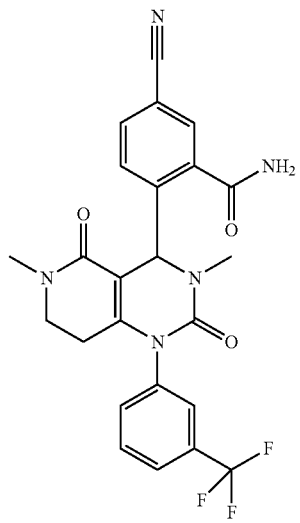
1.l
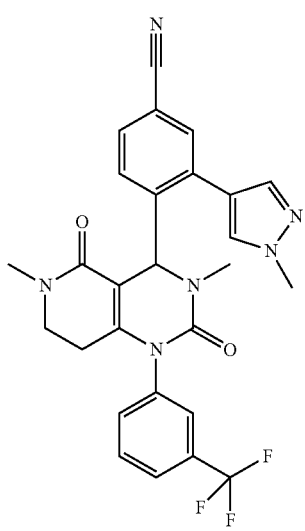
1.j
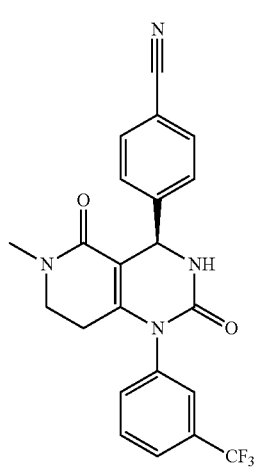
1.m
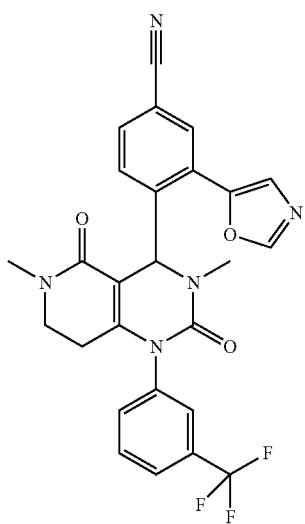
1.k
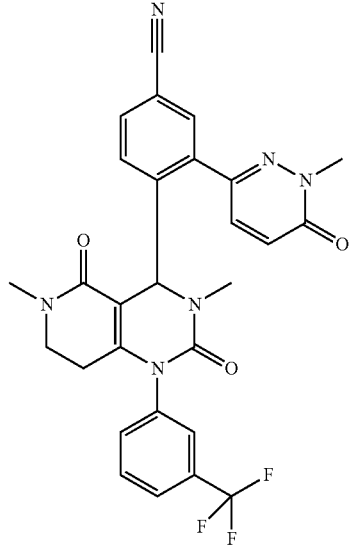
1.n -continued

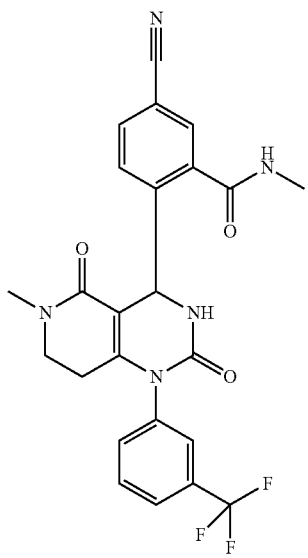

or a pharmaceutically acceptable salt thereof.

9. A compound of formula 1.A according to claim 1,

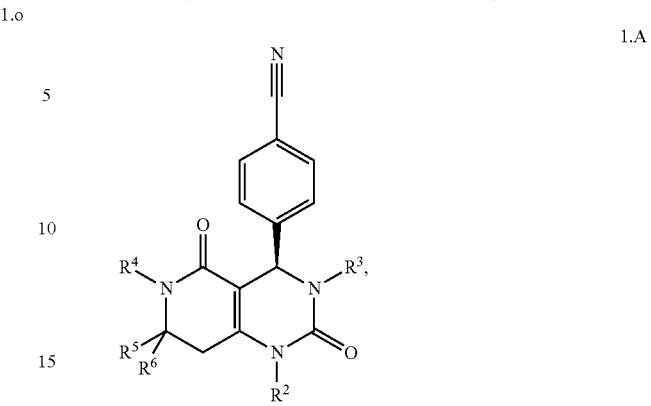

or a pharmaceutically acceptable salt thereof.

10. A pharmaceutical composition comprising a compound according to claim 1 and a pharmaceutically acceptable carrier.

11. A method for the treatment of COPD which comprises administering to a host suffering from COPD a therapeutically effective amount of a compound according to claim 1.

* * * * *